United States Patent
Smith et al.

(10) Patent No.: US 8,999,317 B2
(45) Date of Patent: Apr. 7, 2015

(54) METHODS AND COMPOSITIONS RELATED TO THE STRUCTURE AND FUNCTION OF APOBEC3G

(75) Inventors: Harold C. Smith, Rochester, NY (US); Joseph E. Wedekind, Rochester, NY (US); Ryan Patrick Bennett, Canandaigua, NY (US)

(73) Assignee: University of Rochester, Rochester, NY (US)

( * ) Notice: Subject to any disclaimer, the term of this patent is extended or adjusted under 35 U.S.C. 154(b) by 1228 days.

(21) Appl. No.: 12/513,134

(22) PCT Filed: Nov. 1, 2007

(86) PCT No.: PCT/US2007/083348
§ 371 (c)(1),
(2), (4) Date: Apr. 12, 2010

(87) PCT Pub. No.: WO2008/136852
PCT Pub. Date: Nov. 13, 2008

(65) Prior Publication Data
US 2010/0197768 A1    Aug. 5, 2010

Related U.S. Application Data

(60) Provisional application No. 60/855,863, filed on Nov. 1, 2006.

(51) Int. Cl.
| | |
|---|---|
| *A01N 63/00* | (2006.01) |
| *C12Q 1/70* | (2006.01) |
| *C12N 9/78* | (2006.01) |
| *G01N 33/50* | (2006.01) |
| *A61L 2/16* | (2006.01) |
| *A61L 2/00* | (2006.01) |
| *G01N 33/569* | (2006.01) |
| *C12Q 1/10* | (2006.01) |

(52) U.S. Cl.
CPC *C12N 9/78* (2013.01); *G01N 33/50* (2013.01); *A61L 2/16* (2013.01); *A61L 2/0082* (2013.01); *G01N 33/56983* (2013.01); *C07K 2299/00* (2013.01); *C12N 2740/16011* (2013.01); *C12Q 1/10* (2013.01); *C12Y 305/04005* (2013.01); *G01N 2333/16* (2013.01); *G01N 2333/978* (2013.01); *G01N 2500/02* (2013.01)

(58) Field of Classification Search
None
See application file for complete search history.

(56) References Cited

U.S. PATENT DOCUMENTS

2005/0053977 A1 *  3/2005  Greene et al. .............. 435/6
2005/0287648 A1    12/2005  Smith et al.

FOREIGN PATENT DOCUMENTS

WO    WO2005/023985    3/2005

OTHER PUBLICATIONS

Chelico et al., "APOBEC3G DNA deaminase acts processively 3'→5' on single-stranded DNA." 2006, Nat Struct Mol Biol 13:392-399.
Chen et al., "Alpha interferon potently enhances the anti-human immunodeficiency virus type 1 activity of APOBEC3G in resting primary CD4 T cells." 2006, J Virol 80:7645-7657.
Chiu et al., "High-molecular-mass APOBEC3G complexes restrict Alu retrotransposition." :2006, PNAS 103(42):15588-15593.
Chiu, et al., "Cellular APOBEC3G restricts HIV-1 infection in resting CD4+ T cells." 2005, Nature, 435:108-14.
Kreisberg et al. "Endogenous factors enhance HIV infection of tissue naive CD4 T cells by stimulating high molecular mass APOBEC3G complex formation.", 2006, J Exp Med 203:865-870.
Wedekind et al., "Nanostructures of APOBEC3G Support a Hierarchical Assembly Model of High Molecular Mass Ribonucleoprotein Particles from Dimeric Subunits." 2006 Journal of Biological Chemistry 281(50)38122-38126.

* cited by examiner

*Primary Examiner* — Suzanne M Noakes
*Assistant Examiner* — Jae W Lee
(74) *Attorney, Agent, or Firm* — Riverside Law LLP

(57) ABSTRACT

Disclosed are methods and compositions related to the structure and function of APOBEC3G.

6 Claims, 44 Drawing Sheets

Figure 9A:
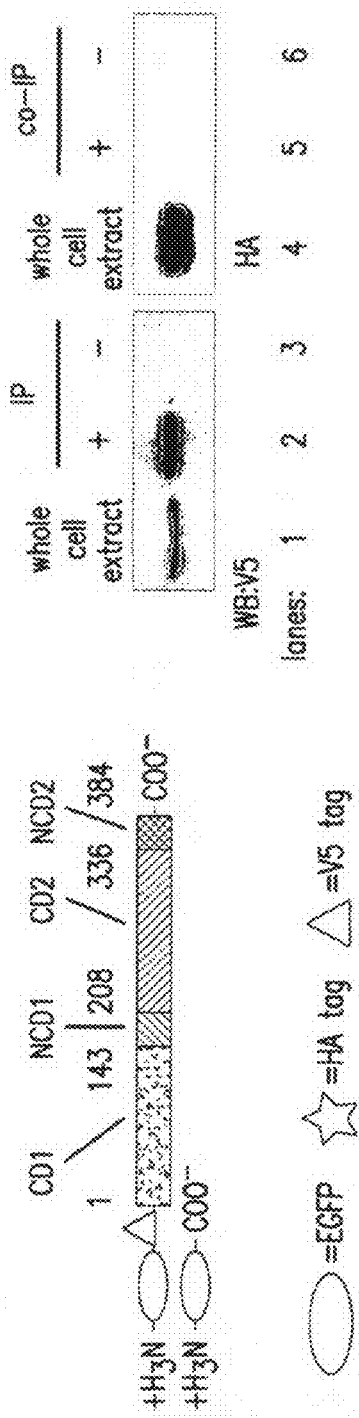

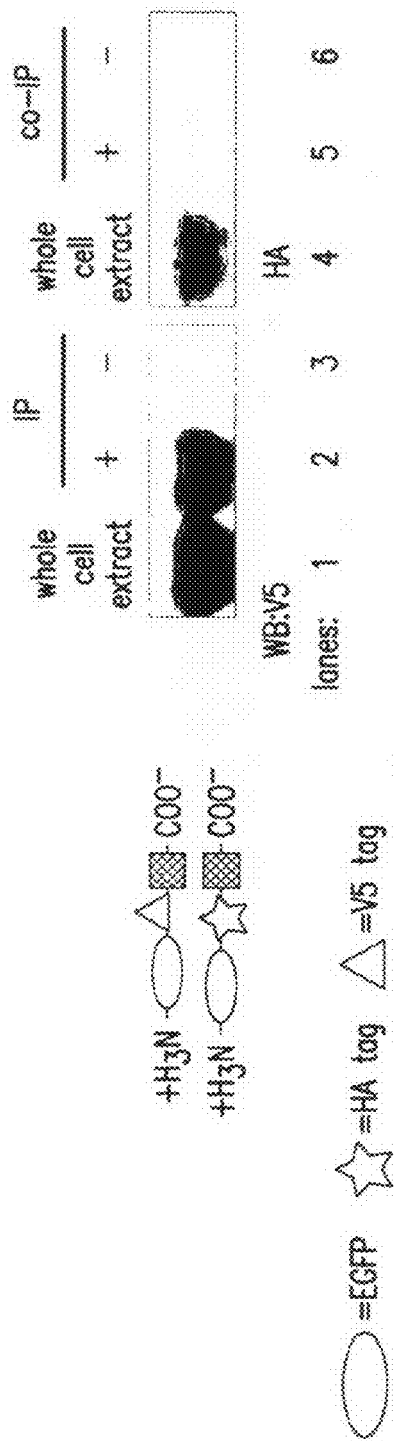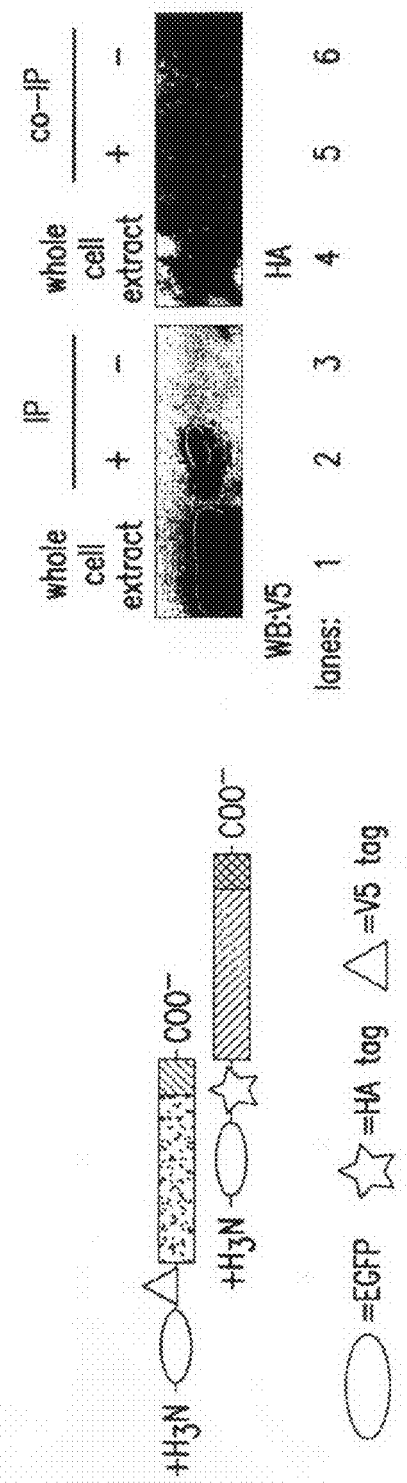
FIG. 9K
FIG. 9L

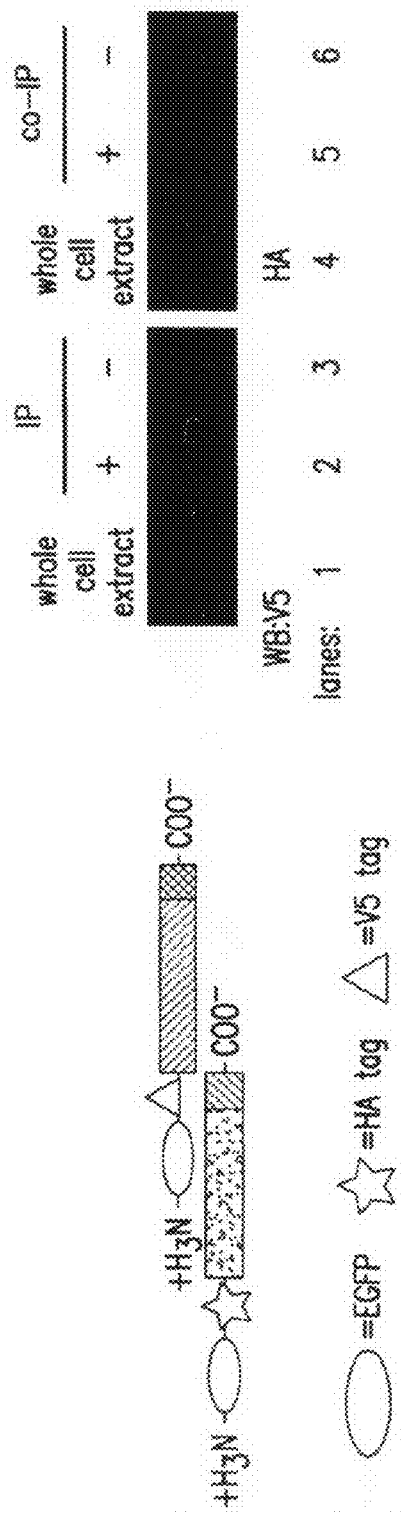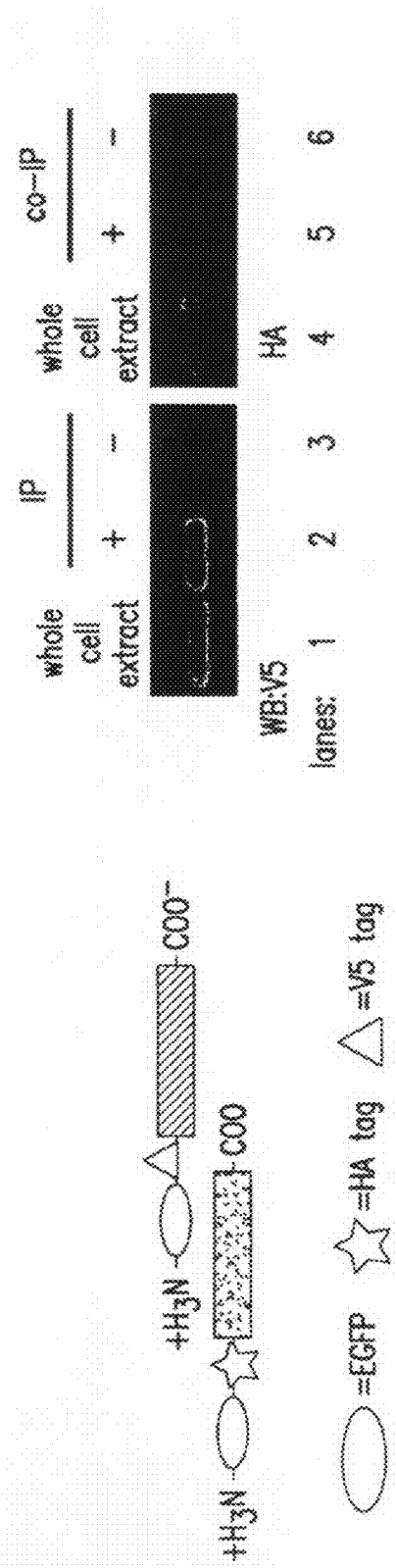
FIG. 9M
FIG. 9N

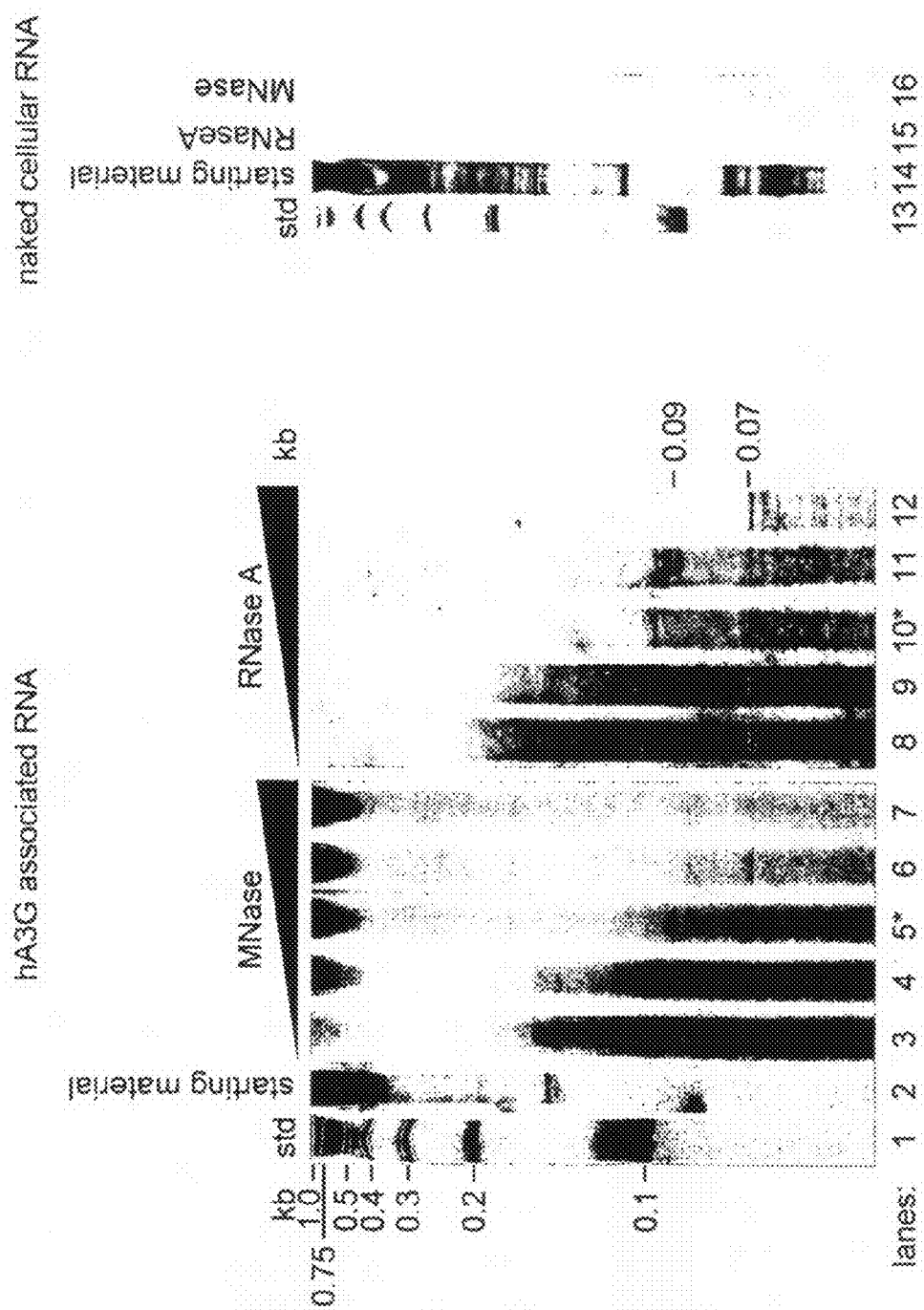

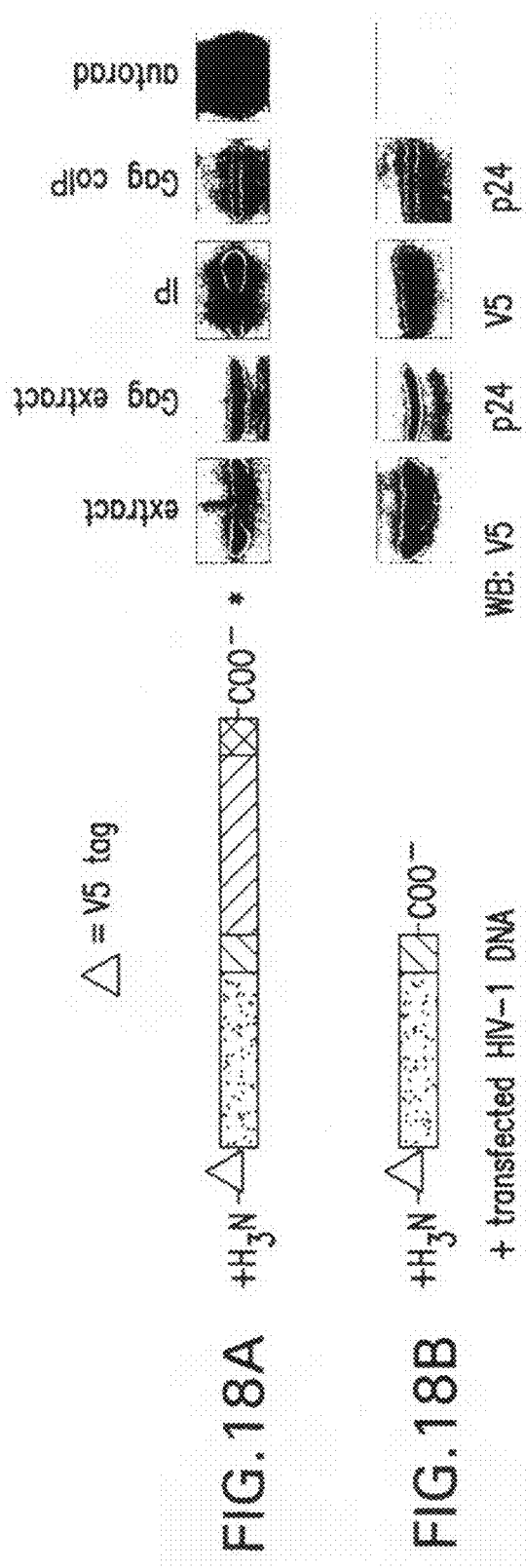

◯ =EGFP

◯ =NLS-EGFP

◯ =EGFP
◯ =NLS-EGFP
△ =HA tag

◯ =EGFP
◯ =NLS-EGFP
△ =HA tag

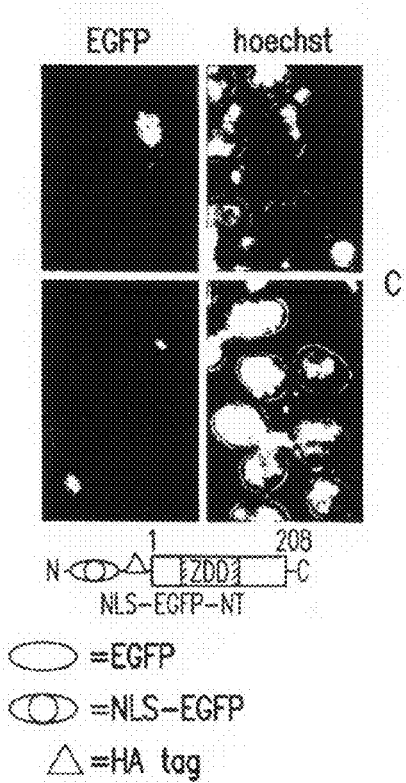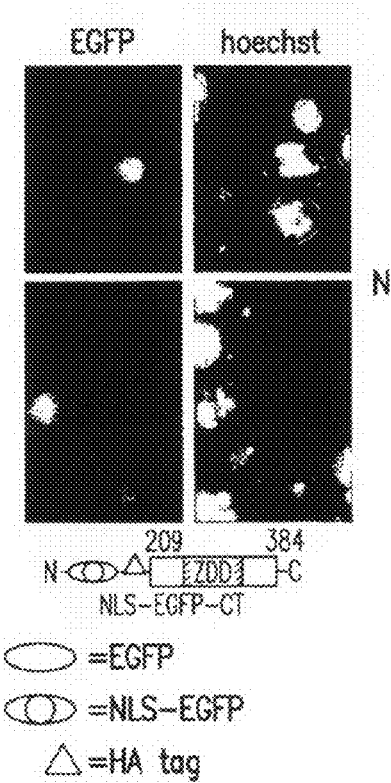
FIG. 19E    FIG. 19F
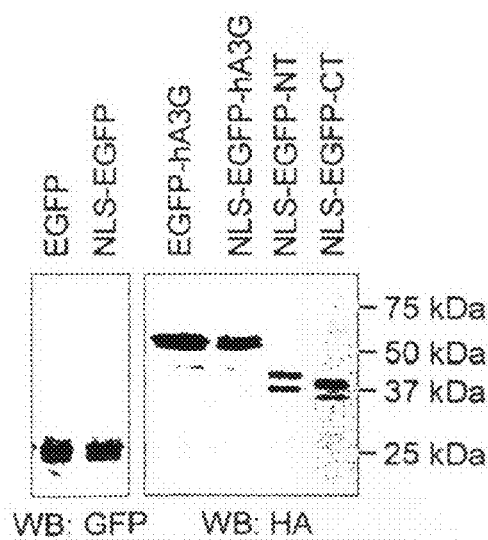
FIG. 19G

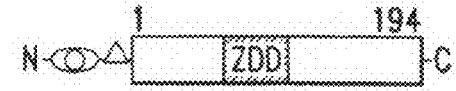 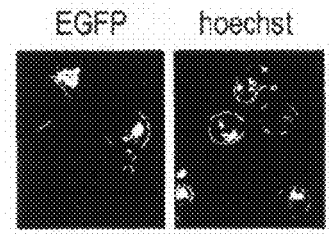
FIG.21A
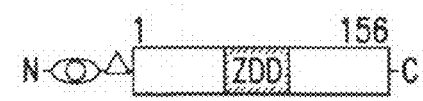 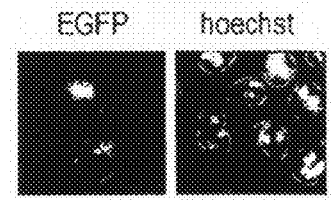
FIG.21B
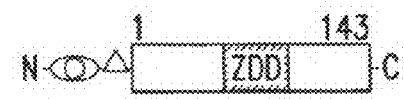 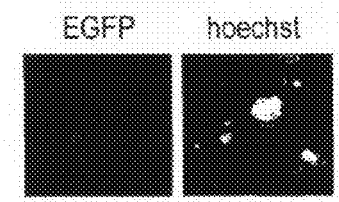
FIG.21C
 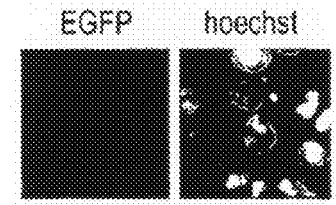
FIG.21D
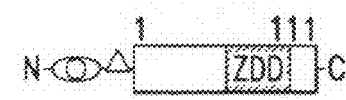 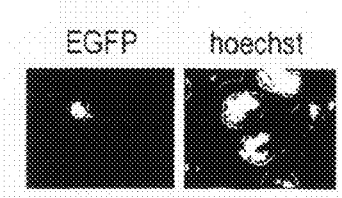
FIG.21E

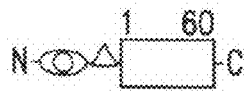 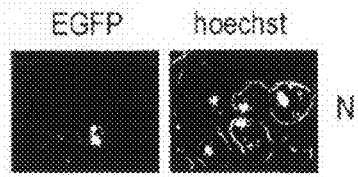
FIG.21F
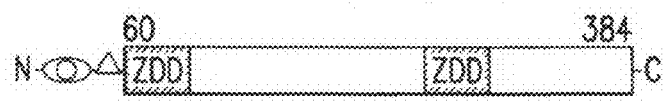 
FIG.21G
 
FIG.21H
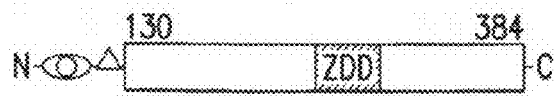 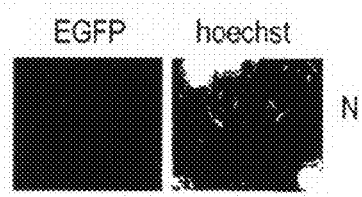
FIG.21I
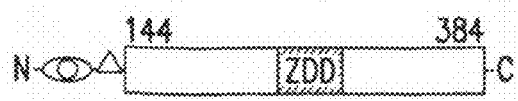 
FIG.21J

US 8,999,317 B2

METHODS AND COMPOSITIONS RELATED TO THE STRUCTURE AND FUNCTION OF APOBEC3G

This application claims the benefit of U.S. Provisional Application No. 60/855,863, filed Nov. 1, 2006.

This invention was made with government support under NIH Grant AI058789-02 and NIH grant T32 AI49815. The government has certain rights in the invention.

I. BACKGROUND OF THE INVENTION

There are several examples of cellular and viral mRNA editing in mammalian cells. (Grosjean and Benne (1998); Smith (1997) RNA 3: 1105-23). Two examples of such editing mechanisms are the adenosine to inosine and cytidine to uridine conversions. (Grosjean and Benne (1998); Smith (1996) Trends in Genetics 12:418-24; Krough (1994) J. Mol. Biol. 235:1501-31). Editing can also occur on DNA.

A to I editing involves a family of adenosine deaminases active on RNA (ADARs). ADARs typically have two or more double stranded RNA binding motifs (DRBM) in addition to a catalytic domain whose tertiary structure positions a histidine and two cysteines for zinc ion coordination and a glutamic acid residue as a proton donor. The catalytic domain is conserved at the level of secondary and tertiary structure among ADARs, cytidine nucleoside/nucleotide deaminases and CDARs but differs markedly from that found in adenosine nucleoside/nucleotide deaminases (Higuchi (1993) Cell 75:1361-70). ADAR editing sites are found predominantly in exons and are characterized by RNA secondary structure encompassing the adenosine(s) to be edited. In human exon A to I editing, RNA secondary structure is formed between the exon and a 3' proximal sequence with the downstream intron (Grosjean and Benne (1998); Smith (1997) RNA 3: 1105-23; Smith (1996) Trends in Genetics 12:418-24; Maas (1996) J. Biol. Chem. 271:12221-26; Reuter (1999) Nature 399:75-80; O'Connell (1997) Current Biol. 7:R437-38). Consequently, A to I editing occurs prior to pre-mRNA splicing in the nucleus. The resultant inosine base pairs with cytosine and codons that have been edited, effectively have an A to G change. ADAR mRNA substrates frequently contain multiple A to I editing sites and each site is selectively edited by an ADAR, such as ADAR1 or ADAR2. ADARs typically function autonomously in editing mRNAs. ADARs bind secondary structure at the editing site through their double stranded RNA binding motifs or DRBMs and perform hydrolytic deamination of adenosine through their catalytic domain.

APOBEC3G (alternatively referred to as CEM15) is a cytidine deaminase and APOBEC-1 homolog. APOBEC3G has been shown to possess antiviral activity. Current therapies for HIV infected patients target the production of new virus by antiviral agents that prevent replication of the viral RNA genomes into DNA prior to integration of the HIV DNA into chromosomal DNA or the disruption of the production or function of viral encoded proteins that are necessary for production of infectious viral particles. Antiviral agents that target viral replication have blunted the course of disease in patients already infected with HIV but these drugs have side effects due to toxicity and, while extending life for many patients, ultimately fail due to the high mutation frequency of HIV-1. Disruption of viral encoded protein production has not been as effective due largely to the high mutation rate of HIV and its consequence of changing the viral protein to one that retains function but no longer is a target for the therapy. A combination of therapies together with better screening of blood supplies and blood products, improved public education and safe-sex practices have curbed the spread of disease only in developed countries but, even in these countries, exhibit incomplete control over the spread of the virus. Needed in the art is a means of editing RNA or DNA involved in disease processes, like HIV, hyper-IgM syndrome, and other cytidine deaminase related diseases, thus preventing or ameliorating the symptoms, and in the case of retroviral-based diseases, eventually eradicating these diseases.

II. SUMMARY OF THE INVENTION

In accordance with the purposes of this invention, as embodied and broadly described herein, this invention, in one aspect, relates to methods and compositions related to treating or preventing viral infection by increasing or sustaining levels of the enzymatically active LMM (low molecular mass) form of APOBEC3G, as compared to the relatively inactive HMM (high molecular mass variant). The disclosed methods and compositions are important improvements over the prior art because of the advantages of increasing anti-viral activity using APOBEC3G.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows small angle X-ray scattering (SAXS) curves and distance distribution functions for hA3G variants. (A) Experimental hA3G-D SAXS curve (circles) and a scattering profile calculated from a representative ab initio model (line). The sample was 1.8 mg mL$^{-1}$ in 1×hA3G buffer plus 0.250 M imidazole. (B) Experimental hA3G-DR SAXS curve (circles) and a scattering profile calculated from a representative ab initio model (line); the sample was 1.1 mg mL$^{-1}$. (C) Distance distribution function, p(r), plot for hA3G-D calculated from I(q) data in (A). The data were fit to a smooth curve and correspond to a maximum particle dimension ($D_{Max}$) of 210 Å. The peak maximum of the curve corresponds to a radius of gyration ($R_G$) of 72.4 Å. (D) Paired-distance distribution function, p(r), for hA3G-DR. $D_{max}$=140 Å with an $R_G$=45.8 Å.

FIG. 2 shows average envelope shapes of hA3G derived from ten ab initio models (A) The hA3G-D model (not treated with RNase). (B) The dimeric model of hA3G-DR (RNase treated). A dashed arrow indicates a two-fold axis relating subunits. FIGS. 2 and 3 were generated by use of Pymol (Delano et al. 2002).

FIG. 3 shows spatial relationships between hA3G-D, hA3G-DR and the rudimentary cytidine deaminase domain. (A) Global fit of two hA3G-DR dimers (left) into the hA3G-D envelope. Regions outside the hA3G-D envelope appear as well. (Inset) The relationship of hA3G-DR dimers packed at left; a black oval indicates a dyad axis. (B) Transparent surface and ribbon depiction of the CDD1 cytidine deaminase structure (PDB entry 1R5T); each ZDD motif is shaded differently. (Inset) a single ZDD domain (residues 1-132) representing the fundamental α/β fold; $Zn^{2+}$ is depicted as a gray sphere. (Right) The hA3G-DR envelope with two independent ZDD domains docked inside. (C) Tail-to-Tail and (D) Head-to-Head schematics of subunit arrangements. NTZDD domain, N-terminal ZDD domain; NTNCD, N-terminal non-catalytic domain; CTZDD domain, C-terminal ZDD domain; and CTNCD, C-terminal non-catalytic domain.

Figure 4:
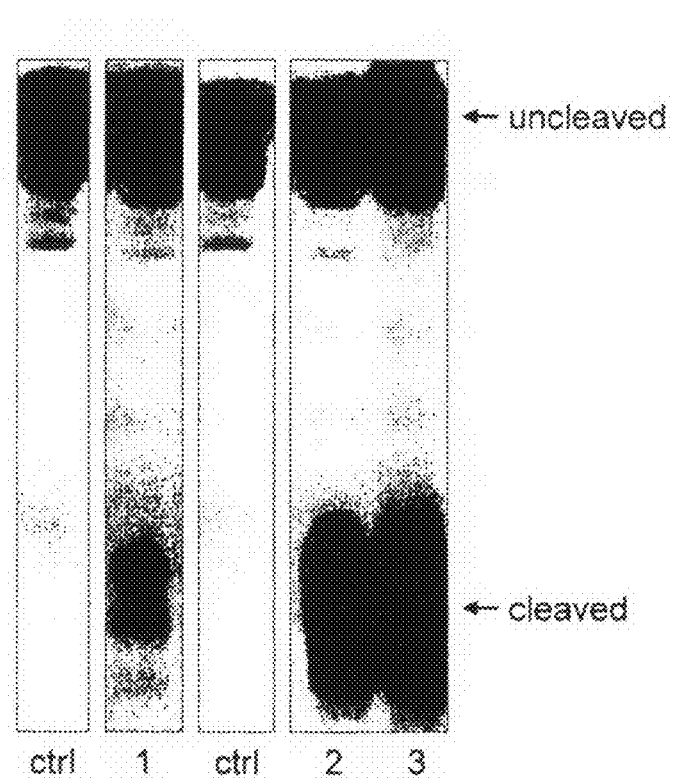

FIG. 4 shows in vitro DNA deamination assays for recombinant hA3G. In control (ctrl) lanes, a DNA strand devoid of the requisite dC target was used as a negative control for both hA3G-D (far left) and hA3G-DR samples (middle). (Lane 1) nominal deaminase activity for hA3G-D showing cleaved products (4% of input substrate edited). (Lanes 2 and 3) deamination products resulting from treatment with hA3G-DR (33% and 52% of input substrate edited, respectively). In these assays, 3 μg of purified protein was used for ctrl, as well as lanes 1 and 3; 1.5 μg was used for lane 2. Reactions were not conducted under multiple turnover conditions. The results are comparable to those shown previously for recombinant hA3G (Iwatani 2006, Opi 2006).

Figure 5:
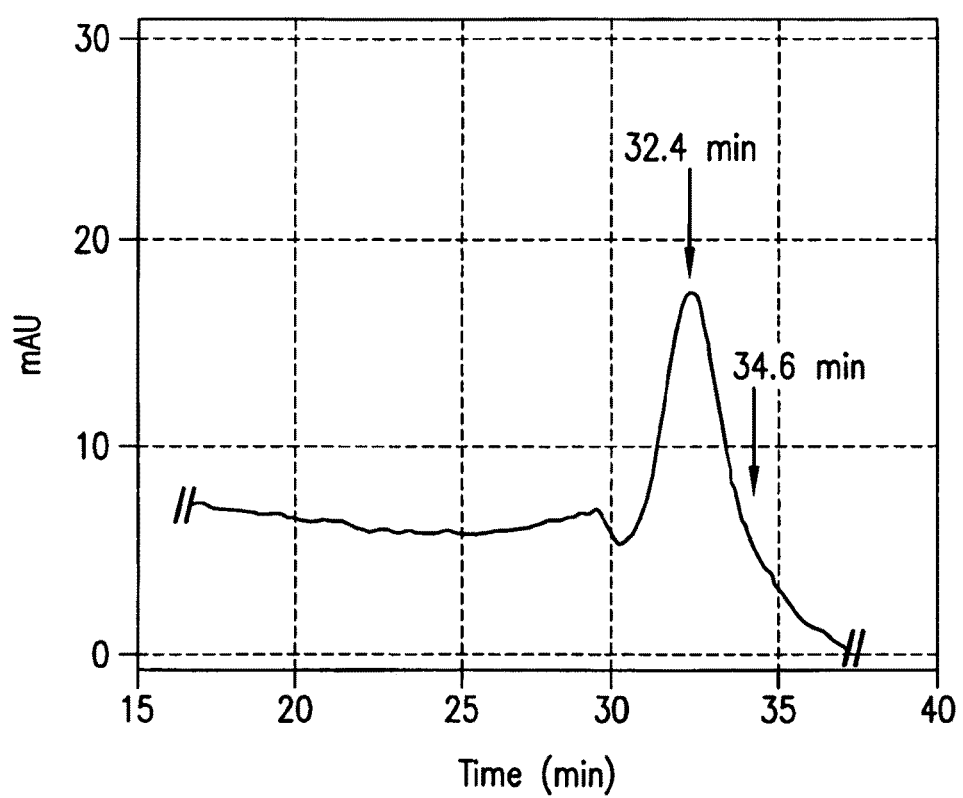

FIG. 5 shows analytical gel filtration chromatography elution profile for hA3G-DR. The major peak eluted at 32.4 min corresponding to a MW of 95.2 kDa. The calculated MW of hA3G-4×His based on its amino acid sequence is 46.96 kDa per subunit. The calculated elution time for monomeric hA3G was 34.6 min. The solid line represents the absorption at 280 nm. The sample concentration was 0.9 mg mL$^{-1}$.

Figure 6A:
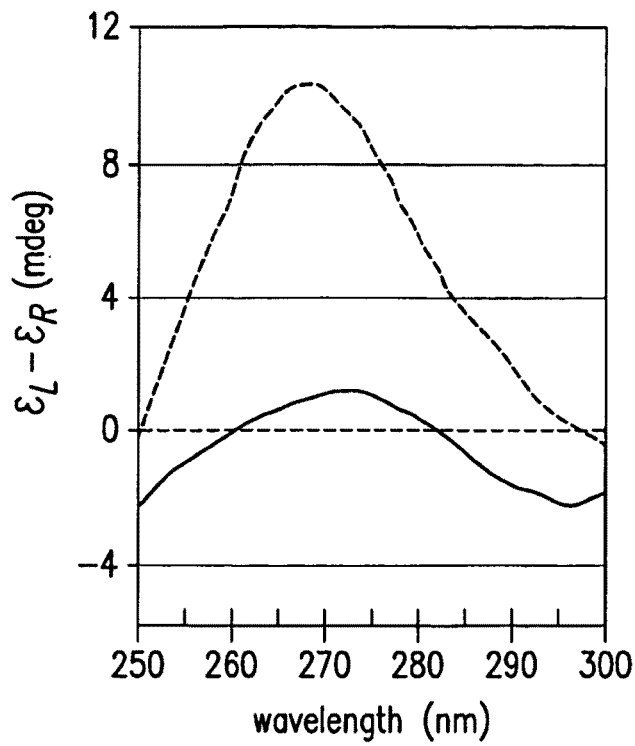
Figure 6B:
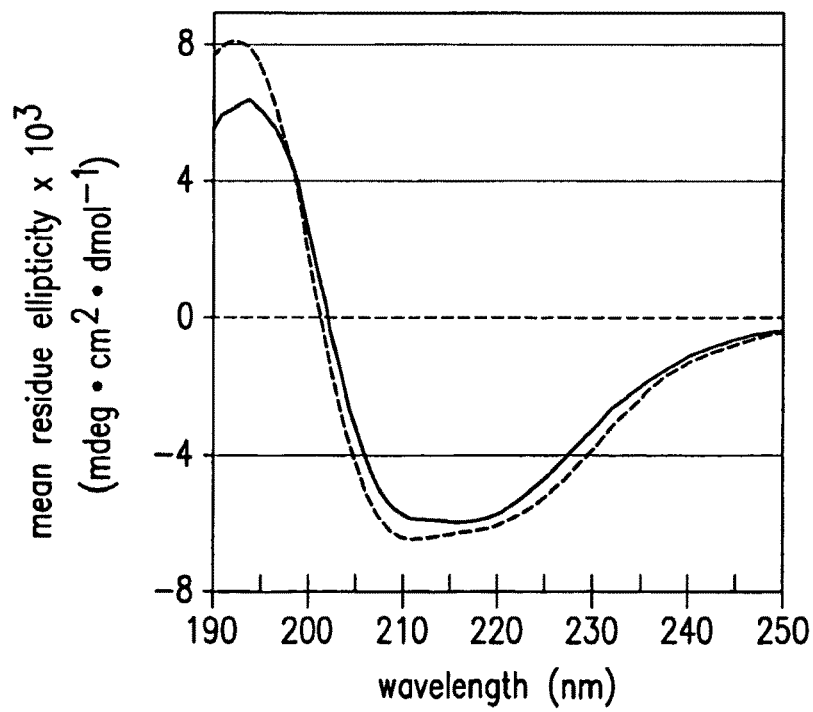

FIG. 6 shows circular dichroism spectra of recombinant hA3G. (A) Near UV spectra for hA3G-D (dashed line) and hA3G-DR (solid line). Samples concentrations were 23 μM and 26 μM, respectively. Spectra were buffer corrected and reported in machine units (i.e. the difference between left and right handed circularly polarized light). (B) Far-UV spectra of hA3G-D (dashed line, no RNase) and hA3G-DR (solid line, RNase treated); protein concentrations were 5.7 μM and 4.3 μM, respectively.

Figure 7:
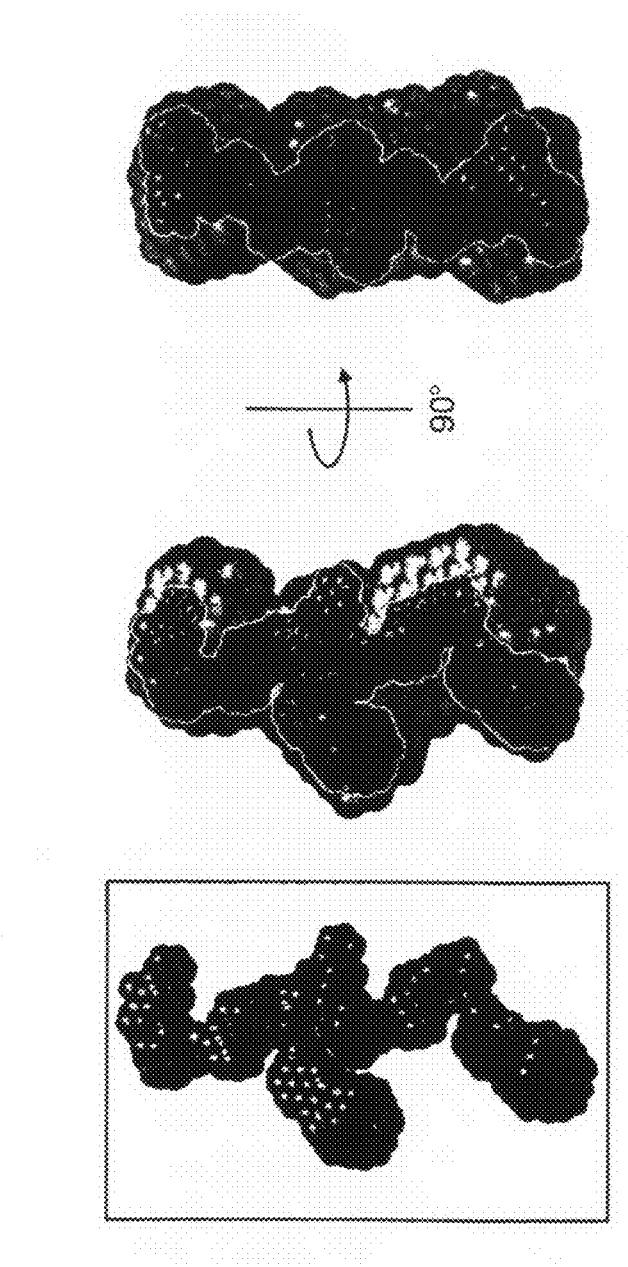

FIG. 7 shows alternative "translational" spatial relationship between hA3G-D and hA3G-DR. The results were obtained by manual rigid body docking and are consistent with the available structural information, although the enantiomorphic structures were used here compared to FIG. 3A. Global fit of the hA3G-DR dimer (left box) into the hA3G-D envelope (middle). hA3G-D is a semi-transparent surface (blue). In this arrangement, two hA3G-DR dimers (dark gray and gray) fit into the hA3G-D molecular envelope by a pure translation. Regions outside the hA3G-D envelope appear as patches. (Right) Rotation of center model.

FIG. 8 shows domain boundaries of hA3G. (a) The polypeptide chain of hA3G delineating the amino acid boundaries of CD1, NCD1, CD2, and NCD2 with the consensus ZDD motif represented within CD1 and CD2. (b) The molecular envelope of the tail-to-tail dimer of hA3G based on SAXS analysis with domains indicated within the model. (c) Dotted boxes show volumes within the hA3G molecular envelope (b) and the Cdd1 tetramer (c, bottom) that accommodate a ribbon model of a single cytidine deaminase subunit with a zinc ($Zn^{2+}$) molecule displayed as a cyan sphere (c, top).

FIG. 9 shows co-immunoprecipitations of alternatively tagged hA3G domains. The hA3G domains co-transfected into 293T cells are represented in the left column as bars for CD1, NCD1, CD2, and NCD2 and symbols for EGFP, HA, and V5 tags. Lanes 1 and 4 are westerns showing the expression of each transfected protein in whole cell extracts. Lanes 2 and 5 are westerns showing Wed and co-Wed proteins, all IPs were performed with V5 antibody. Lanes 3 and 6 are negative controls for non-specific binding to Protein A beads. The antibody used for western blotting (WB) is indicated on the bottom right for IP and co-IP westerns, V5 and HA, respectively. (a) A negative control with EGFP alone. (b) A positive control showing hA3G co-IPs it's alternatively tagged version. (c-o) Co-IPs of alternatively tagged hA3G domains with conditions in which co-IP was successful indicated by (*).

Figure 10:
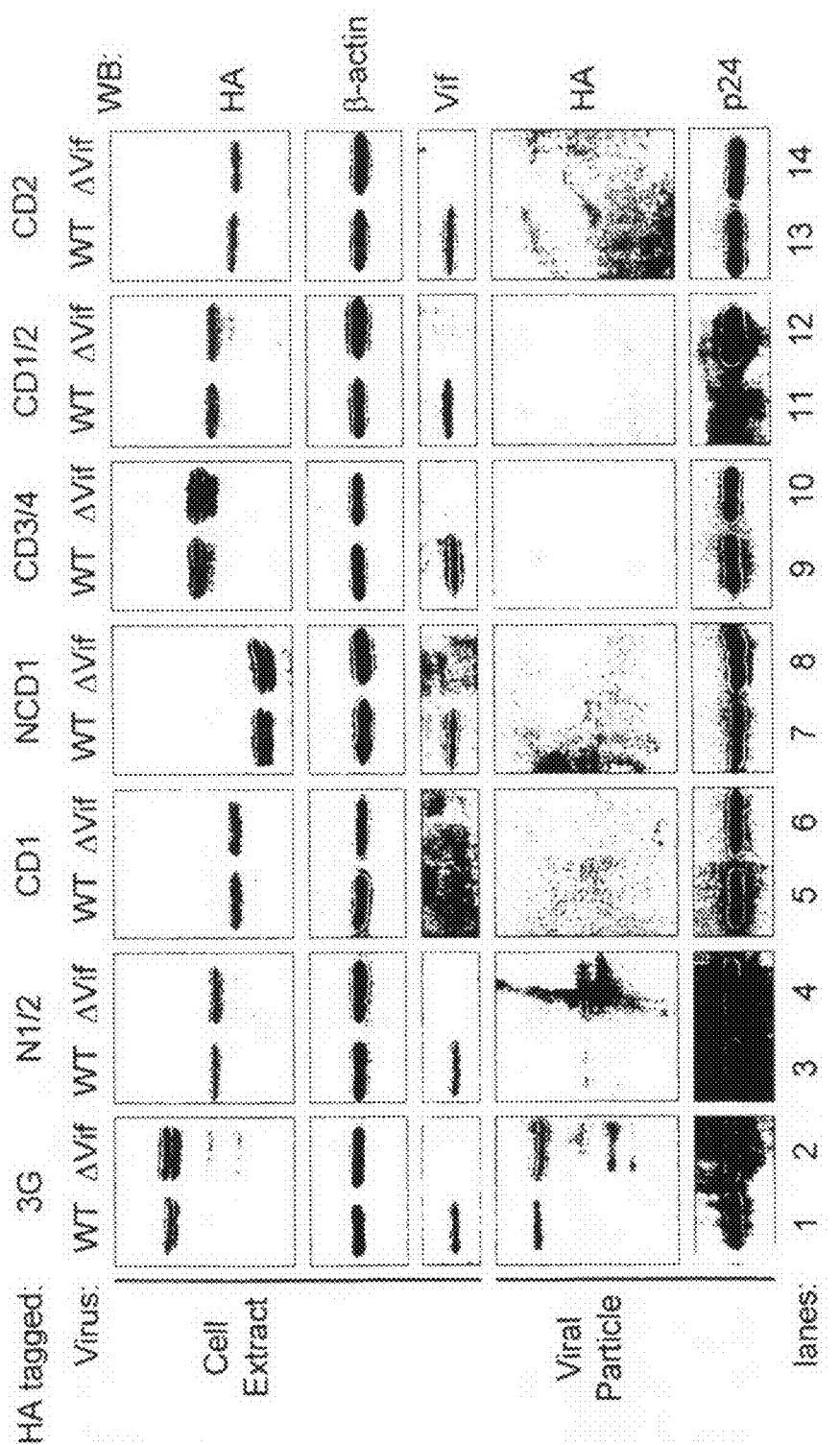

FIG. 10 shows viral encapsidation of hA3G domains. Western blots of cell extracts and viral particles isolated from 293T cells were transfected with EGFP-HA tagged hA3G domains (indicated across top) and co-transfected with HIV-1 DNA (WT) or ΔVif HIV-1 DNA (ΔVif). Antibodies used for westerns are shown on the right. Western blotting with antibody reactive with β-actin and p24 demonstrate equivalent protein loading of cell extracts and viral particles, respectively. Vif westerns show that WT virus expressed Vif and ΔVif virus did not. HA westerns show domains of different sizes expressed in cell extracts (top) and whether they were packaged into viral particles (bottom).

FIG. 11 shows hA3G domains that interact with Gag and Vif. hA3G domains and their V5 or EGFP-V5 tags are keyed as in FIG. 9 and are shown in the left column. (Gag Binding) Lanes 1-5 are westerns of hA3G and Gag from 293T cells co-transfected with hA3G domains (a-e) and HIV-1 DNA into 293T cells. Lanes 1 and 2 are westerns of whole cell extracts and V5 IPs, respectively, of the adjacent hA3G domains detected with V5 antibody. Lanes 3 and 4 are westerns of whole cell extract and co-IPs, respectively, of Gag detected with a p24 antibody. Lane 5 is negative control for non-specific Gag binding to Protein A. (Vif binding) lanes 6-10 are westerns of hA3G and Vif from 293T cell co-transfected with hA3G domains (a-d) and EGFP-HA tagged Vif. In (a, b, and d) GFP antibody was used to IP and western blot (WB) Vif. In (c) both Vif and CD1 had EGFP tags therefore CD1 was IPed with its unique V5 tag and Vif was western blotted for its unique HA tag. Lanes 6 and 7 represent whole cell extracts and IPs, respectively, of Vif. Lane 8 is the negative control for non-specific Vif binding to Protein A. Lanes 9 and 10 represent whole cell extracts and co-IPs, respectively, of the adjacent hA3G domains. It must also be noted that negative 1P and co-IPs for non-specific binding of hA3G domains to Protein A were shown in FIG. 9, thus they were not repeated here. Conditions in which co-IP was successful are indicated by (*).

FIG. 12 shows RNase protection of specific sizes of RNA by hA3G. All images are of silver stained denaturing RNA PAGE with RNA markers (lanes 1, 13, 17 and 23) and kb indicated on the left. The kb on the right indicates sizes of bands estimated by a semi-log plot of the standards and by the distances run by the dye fronts that disappeared in the staining process. (a) RNA co-purified with 4his-hA3G over a nickel column (lane 2) and RNAs protected from increasing amounts of MNase (lanes 3-7) and RNase A (lanes 8-12) at 37° C. (b) Total naked cellular RNA (lane 14) and the lack of protected RNA fragments when the naked cellular RNA was digested with RNase A and MNase at concentrations indicated by (*) in (a) (lanes 15 and 16). (c) MNase digestions as in (a) done at 4° C. (d) RNA associated with hA3G that was treated with a high concentration RNase A during cell lysis 1, 2 and 3 days after purification.

FIG. 13 shows RNA UV crosslinking of full-length hA3G and domains. hA3G domains and their V5 or EGFP-V5 tags are keyed as in FIG. 9 and are shown in the left column. Lanes 1 and 2 are westerns of whole cell extracts and IPs, respectively, from 293T cells transfected with adjacent full-length hA3G (a) or domains (b-f) detected with V5 antibody. Lane 3 represents the autorad showing the presence or absence of RNA UV crosslinking due to 32P radiolabeled nucleotides that remained covalently crosslinked to the adjacent full-length hA3G or domain after exposure to short wave UV light, RNase digestion, and IP.

Figure 14:
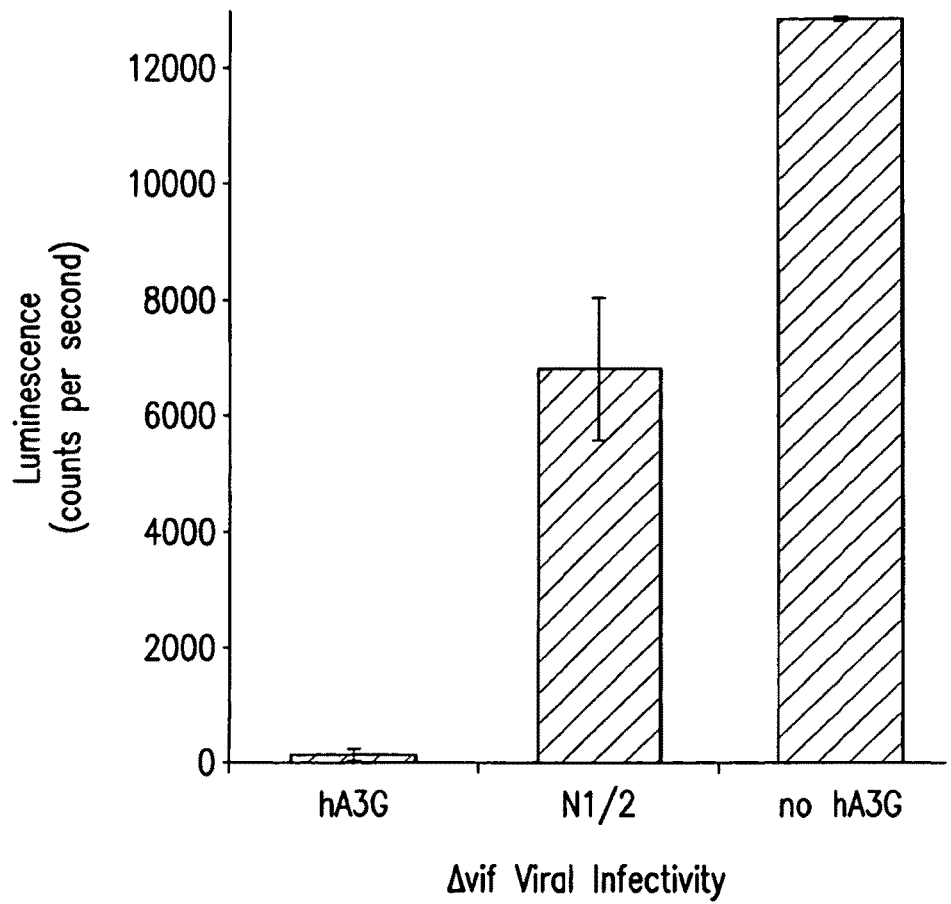

FIG. 14 shows single round infectivity assay with Δvif virus. 293T cells were co-transfected with Δvif HIV-1 DNA and VSV-G envelope, along with hA3G, N1/2 or vector control (no hA3G). The viral particles collected from the cell culture media were normalized for their p24 content and added to TZM-bl cell cultures for analysis of infectivity corresponding to luminescence as described in Example 2. Bars represent standard deviations with an n=3.

Figure 15:
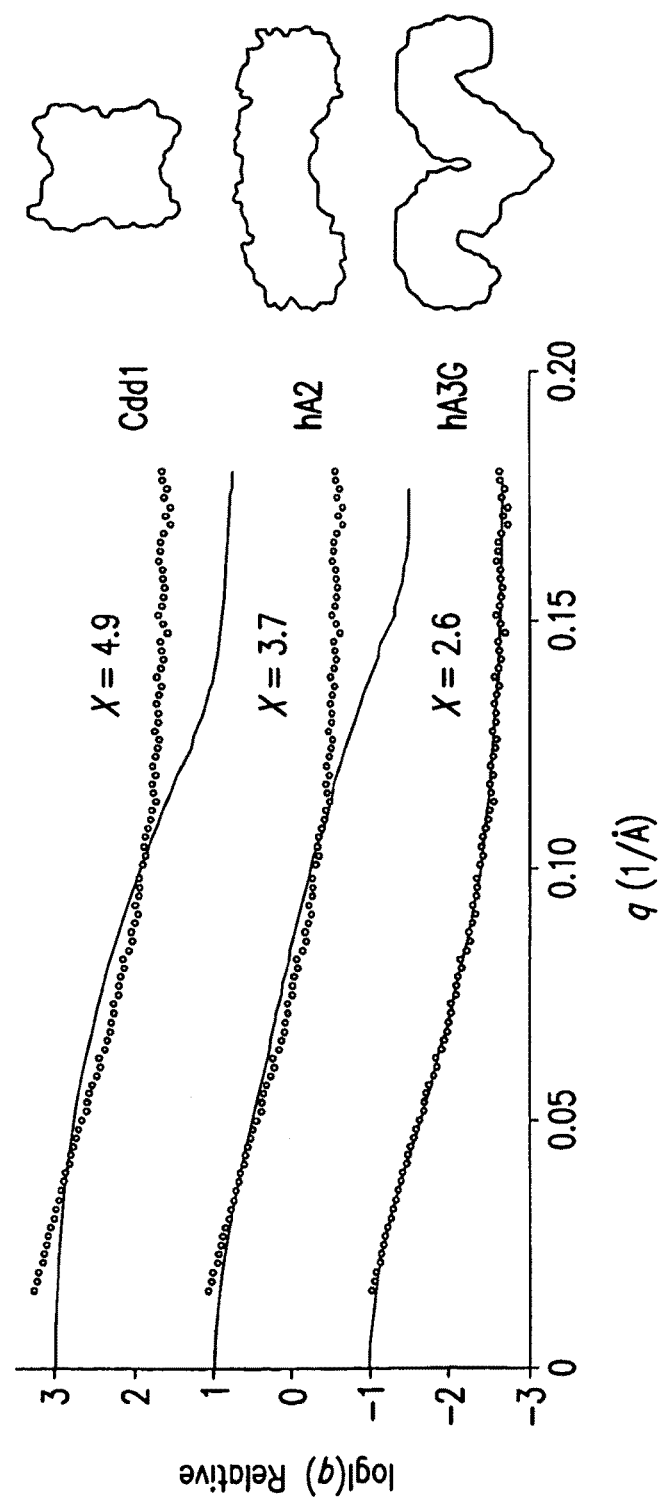

FIG. 15 shows a comparison of the observed scattering profile of hA3G in solution relative to those derived from various three-dimensional models. The scattering profile (curve) was generated from the crystal structure of the 'square' cytidine deaminase Cdd1, shown as a ribbon model with a transparent surface (right). Each Cdd1 subunit is identical, but colored differently to emphasize the tetrameric oligomer arrangement. The shape agreement between the observed scattering data for hA3G (open circles) versus the scattering profile calculated from the Cdd1 crystallographic coordinates is indicated by the value of $\chi$. Values of $\chi$ close to unity indicate good agreement. Similar comparisons are shown for APOBEC-2 (hA2, PDB entry 2nyt), which comprises four identical subunits, and a restored dummy atom model corresponding to hA3G as described herein.

Figure 16:
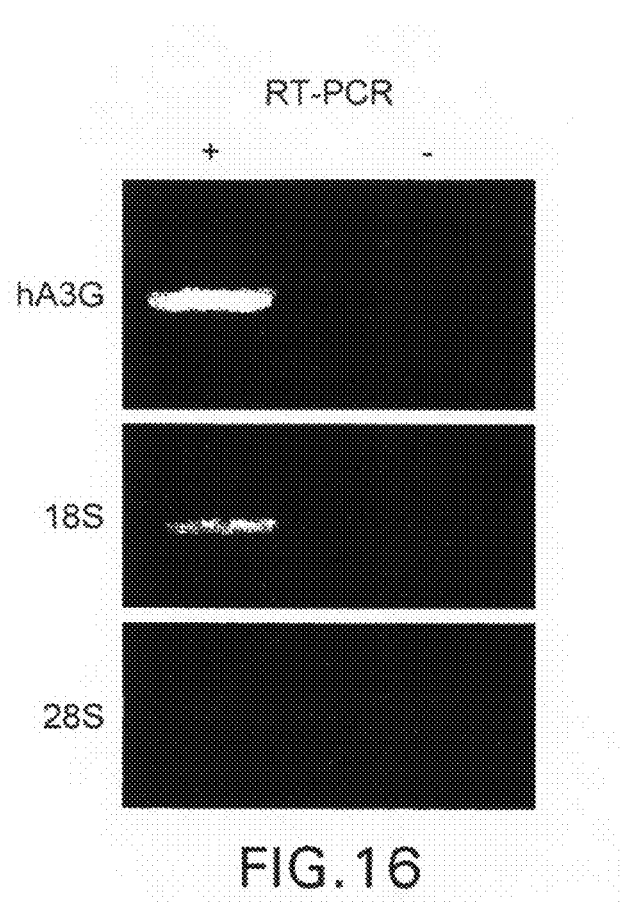

FIG. 16 shows RT-PCR of RNA co-purified with hA3G. Isolated RNA that co-purified with hA3G was RT-PCRed with primers for hA3G mRNA, 18S rRNA or 28S rRNA as described in Example 2. The (+) lane shows ethidium bromide stained DNA bands corresponding to the adjacent RNA. The (−) lane shows that RNA and not DNA was amplified due to lack of DNA bands when RT-PCR was done in the absence of reverse transcriptase.

Figure 17:
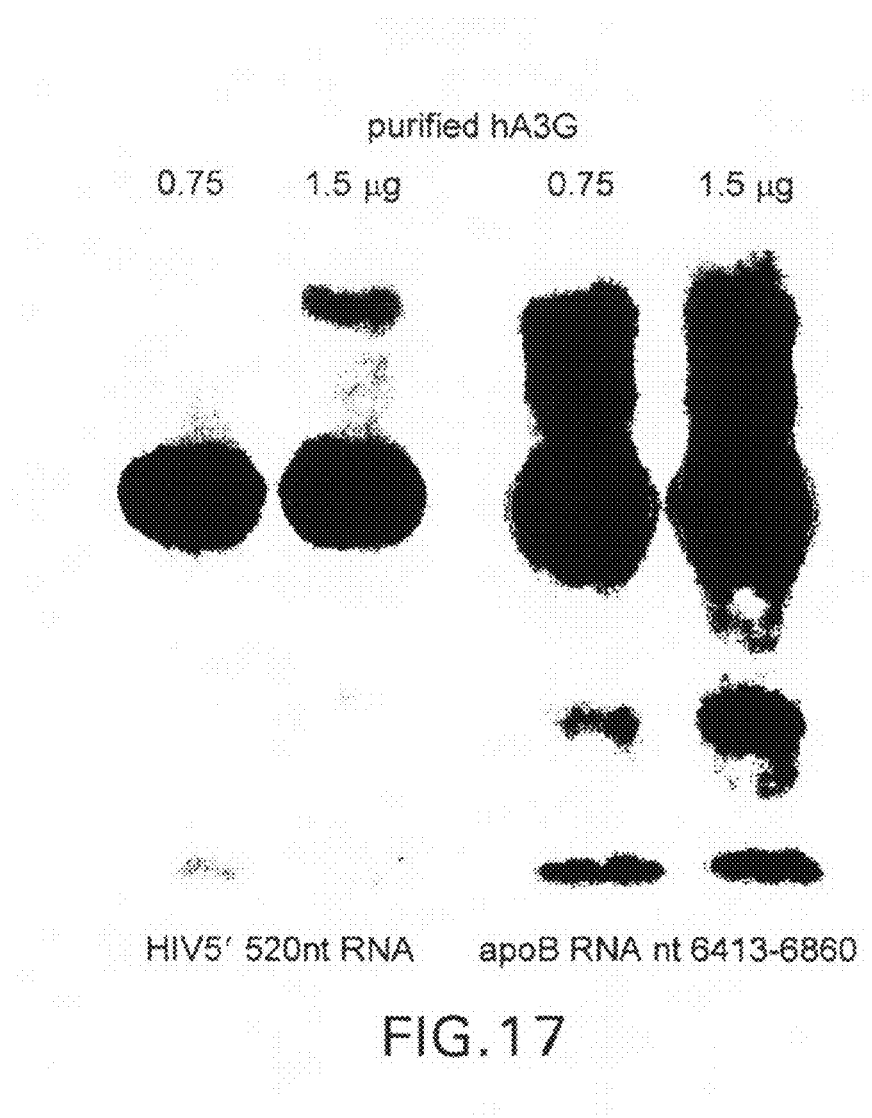

FIG. 17 shows RNA UV crosslinking to purified hA3G. 0.75 and 1.5 µg of purified hA3G was incubated with $^{32}$P radiolabeled RNAs of HIV 5' 520 nt (left) or apoB RNA nt 6413-6860 (right) and UV crosslinked as described in Example 2. Shown is the autorad of SDS-PAGE revealing crosslinked protein bands at ~40 kDa corresponding to purified hA3G.

FIG. 18 shows RNA UV crosslinking of full-length hA3G and N1/2 in complex with Gag. V5 tagged hA3G (a) and N1/2 (b) are keyed as in FIG. 9 and are shown in the left column. The antibody used for westerns of whole cell extracts and IPs, respectively, from 293T cells transfected with HIV-1 DNA and hA3G (a) or N1/2 (b) are indicated below each lane. The autorad lane represents the presence or absence of RNA UV crosslinking due to $^{32}$P radiolabeled nucleotides that remained covalently crosslinked to the adjacent full-length hA3G or domain after exposure to short wave UV light, RNase digestion, and IP.

FIG. 19 shows visualization of the affect of the cytoplasmic retention signal from hA3G in living cells. (A-F) The EGFP fluorescence (EGFP, left) and the live cell nuclear staining with hoechst (right) of two separate fields are shown for 293T cells transfected with the reporter construct that is listed below each set of images. The observed localization is given on the right as cytoplasmic (C), nuclear (N), or cytoplasmic and nuclear (C/N). A key for symbols used for NLS-EGFP, EGFP and the HA tag is shown at the bottom of the panels. Full-length hA3G (a.a. 1-384) and either the N- or C-terminal halves are shown as bar diagrams below their respective images showing. The relative location of the ZDD motif (black) is shown within each protein construct. (G) Western blots (WB) reacted with anti-GFP or anti-HA (indicated below) were used to evaluate expression and size of each protein construct. The migration of molecular mass standards is indicated to the right.

Figure 20:
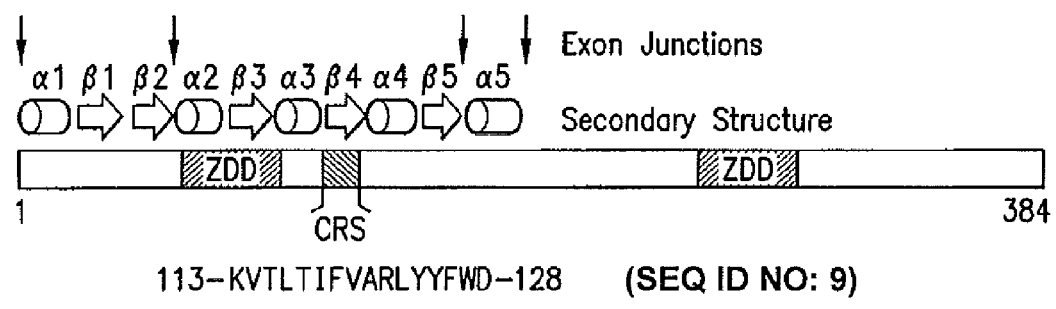

FIG. 20 shows the predicted secondary structure, exon junctions, ZDD motifs and CRS of hA3G. A bar diagram of hA3G with structurally predicted alpha helices (a) and beta strands (b) is graphically depicted as cartoon barrels and arrows, respectively, with (↓) indicating where exon junctions occur. The regions containing the ZDD motifs (black) and the CRS (gray) are indicated within the bar diagram with the 16 amino acids in the CRS listed (bottom).

FIG. 21 shows deletion mapping of the hA3G CRS with NLS-EGFP. (A-J) The EGFP fluorescence (EGFP, left) and the live cell nuclear staining with hoechst (right) are shown for 293T cells transfected with the reporter construct listed to the left of each set of images. The observed localization is given on the right as cytoplasmic (C), nuclear (N), or cytoplasmic and nuclear (C/N). The first and last amino acid of each deletion construct was designed based on predicted loop regions and/or exon junctions shown in FIG. 20 and are shown above each bar diagram. The key for symbols used for NLS-EGFP and the HA tag are also shown (bottom). (K) Western blots (WB) with anti-GFP detecting the protein constructs indicated above each lane by their boundary amino acid positions. The migration of molecular mass standards is indicated to the right.

FIG. 22 shows confirmation of the location of the CRS within hA3G with EGFP. (A-E) The EGFP fluorescence (EGFP, left) and the live cell nuclear staining with hoechst (right) are shown for 293T cells transfected with the reporter construct listed to the left of each set of images. The observed localization is given on the right as cytoplasmic (C), or cytoplasmic and nuclear (C/N). The key for symbols used for EGFP and the HA tag are also shown (bottom).

Figure 23A:
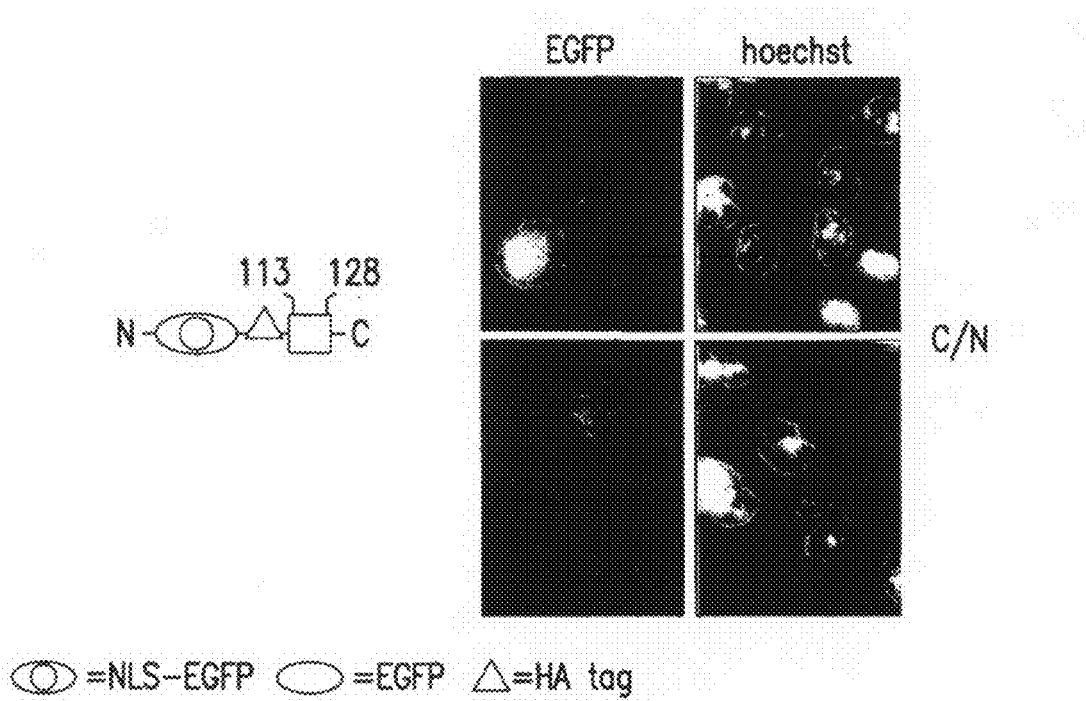

FIG. 23 shows the CRS within hA3G acts autonomously to localize NLS-EGFP and retain EGFP reporters in the cytoplasm. (A and B) The EGFP fluorescence (EGFP, left) and the live cell nuclear staining with hoechst (right) of two separate fields are shown for 293T cells transfected with the reporter construct listed to the left of each set of images. The observed localization is given on the right as cytoplasmic (C), or cytoplasmic and nuclear (C/N). The key for symbols used for NLS-EGFP, EGFP and the HA tag are shown (bottom). (C) Western blot with anti-GFP detecting EGFP-HA-113-128. The migration of molecular mass standards is indicated to the right.

IV. DETAILED DESCRIPTION

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

By "subject" is meant an individual. Preferably, the subject is a mammal such as a primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

By "contacting" is meant an instance of exposure of at least one substance to another substance. For example, contacting can include contacting a substance, such as a cell, or cell to a protein or analog described herein. A cell can be contacted with the protein or analog, for example, by adding the protein or analog to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the protein or analog is present at physiologically effective levels or at presumed physiologically effective levels in the medium or extracellular fluid bathing the cell. In some forms of the disclosed methods, for example, a virally infected cell (e.g., an HIV infected cell) or a cell at risk for viral infection (e.g., before, at about the same time, or shortly after HIV infection of the cell) can be contacted with a protein or analog.

"Treatment" or "treating" means to administer a composition to a subject with an undesired condition or at risk for the condition. The condition can be any pathogenic disease, autoimmune disease, cancer or inflammatory condition. The effect of the administration of the composition to the subject can have the effect of but is not limited to reducing the symptoms of the condition, a reduction in the severity of the condition, or the complete ablation of the condition.

By "effective amount" is meant a therapeutic amount needed to achieve the desired result or results, e.g., editing nucleic acids, interrupting APOBEC3G-Vif binding, reducing viral infectivity, altering the qualitative or quantitative nature of the proteins expressed by cell or tissues, altering the physiological shape of the APOBEC3G molecule, enhance functionality or stability of the LMM molecule, degrade or sequester the HMM molecule, etc.

Herein, "inhibition" or "inhibits" means to reduce activity as compared to a control (e.g., activity in the absence of such inhibition). It is understood that inhibition can mean a slight reduction in activity to the complete ablation of all activity. An "inhibitor" can be anything that reduces activity.

Many methods disclosed herein refer to "systems." It is understood that systems can, for example, be cells or, for example, columns or batch processing containers, or, for example, culture plates, or for example the combination of unique bacterial or mammalian cells together with recombinant molecules expressed therein such as in a genetic screening system used for the purpose of enriching and identifying macromolecules with sequences of specific interest. A system can be a set of components, any set of components that allows for the steps of the method to performed. Typically a system can comprise one or more components, such as a protein(s) or reagent(s). One type of system disclosed would be a cell that comprises APOBEC3G for example. Another type of system would be one that comprises a cell and an infective unit (e.g., an HIV unit). A third type of system might be a chromatography column that has APOBEC3G bound to the column. A fourth type of system might be a cell that comprises APOBEC3G.

By "virally infected mammalian cell system" is meant an in vitro or in vivo system infected by a virus. Such a system can include mammalian cellular components; mammalian cells, tissues, or organs; and whole animal systems.

The terms APOBEC3G and CEM15 are used interchangeably throughout. "hA3G" is also used to refer to the human form of APOBEC3G. APOBEC3G reduces HIV infectivity as a DNA mutating (editing) enzyme. APOBEC3G mRNA substrates transcribed from either HIV-1 viral genomes or host cell genomes can be edited by APOBEC3G as well "HMM" refers to the high molecular mass form of APOBEC3G, and "LMM" refers to the low molecular mass form of APOBEC3G. As disclosed herein, APOBEC3G can exist in two forms, HMM and LMM. The HMM form is catalytically inactive, and is larger in molecular mass than the LMM form. It is primarily found in HIV-permissive activated CD4+T-cells. The LMM form is catalytically active, and is primarily found in HIV non-permissive CD4+T-cells. It should be noted that these two forms differ in molecular mass and in physical structure, and one of skill in the art would readily be able to assess the difference between the two. A more detailed description of these two forms follows.

It is understood that the disclosed compositions can be labeled. Labeling can include covalent attachment of one or more labels, directly or through a spacer (e.g., an amide group), to non-interfering position(s) on the molecule being labeled, which can be determined empirically or through structure and structure-activity data and/or molecular modeling. Derivitization (e.g., labeling) of the compositions should not substantially interfere with the desired biological or pharmacological activity of the composition.

B. General

Human APOBEC3G (also referred to herein as hA3G or CEM15) is a cytidine deaminase (CDA) that restricts HIV-1 infection in a vif-dependent manner. hA3G from HIV-permissive activated CD4+ T-cells exists as an inactive, high-molecular-mass (HMM) complex that can be transformed in vitro into an active, low-molecular-mass (LMM) variant comparable to that of HIV-non-permissive CD4+T-cells. Shown herein are structures for hA3G in HMM and LMM forms determined by small angle X-ray scattering (SAXS) and advanced shape reconstruction methods. The results show that LMM particles have an extended structure, dissimilar to other cytidine deaminases, featuring novel tail-to-tail dimerization. Shape analysis of LMM and HMM structures revealed how symmetric association of LMM hA3G dimers can lead to minimal HMM ribonucleoprotein variants approximately 300 kDa in mass. These observations show that the disruption of cellular HMM particles can be achieved by regulation of protein-RNA, as well as protein-protein interactions.

As disclosed above, APOBEC3G is naturally occurring anti-retroviral host defense factor that restricts HIV infection by vif-deficient viral strains (Sheehy et al. 2002). hA3G is packaged into HIV-1 virions (Mariani et al. 2003, Stopak et al. 2003) and causes extensive dC-to-dU mutations of minus polarity viral DNA during reverse transcription (Yu et al. 2004). Such 'DNA editing' results in extensive dG-to-dA changes in the viral cDNA that contribute to reduced HIV infectivity (Harris et al. 2003, Mangeat et al. 2003, Zhang et al. 2003). However, a deaminase independent anti-viral mechanism exists as well (Newman et al. 2005) that entails RNA binding (Navarro et al. 2005). Although hA3G does not edit RNA, it exhibits general RNA binding properties (Jarmuz et al. 2002, Iwatani et al. 2006, Kozak et al. 2006). The principal form of hA3G in HIV infection-permissive CD4+ cells of lymphoid tissues is an HMM ribonucleoprotein complex with little or no deaminase activity (Chiu et al. 2005, Kreisberg et al. 2006). In contrast, an enzymatically active, LMM form of hA3G predominates in peripheral blood CD4+ cells, and serves as a potent post-entry HIV restriction factor (Chiu et al. 2005, Kreisberg et al. 2006). Activation of such cells recruits the LMM enzyme into HMM complexes rendering the cell permissive to infection (Kreisberg et al. 2006). In vitro treatment of HMM hA3G with RNase or in vivo treatment with interferon generates the enzymatically active LMM form and shows that anti-viral activity involves RNA-protein interactions (Chiu et al. 2005, Chelico et al. 2006, Chen et al. 2006).

hA3G belongs to the family of APOBEC-1 related proteins characterized by a ZDD fold featuring the consensus sequence $(C/H)xEx_{25-30}PCxxC$ (Wedekind et al. 2003). Although homology models have been generated for some APOBEC-1 family members (Navaratnam et al. 1998, Xie et al. 2004), no empirical structural information previously existed for it or any other members of the APOBEC family. The protein arose from a novel gene duplication of the fundamental ZDD motif such that tandem active sites are present in each subunit (Wedekind et al. 2003), which must be accounted for in modeling. To provide insight into the fundamental physical properties of hA3G in relation to known cytidine deaminase structures, as well as how hA3G oligomerization contributes to retroviral restriction, a solution SAXS analysis of the recombinant enzyme in its HMM and LMM forms was used.

Disclosed are methods and compositions for increasing the LMM (low molecular mass) form of APOBEC3G in a cell. This may be accomplished by a variety of methods which are disclosed herein.

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that, while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

By "derivative" or "variant" is meant a polypeptide having a particular sequence that differs at one or more positions from a reference sequence. The fragments or derivatives of a full length protein preferably retain at least one function of the full length protein. For example, a fragment or derivative of a deaminase includes a fragment of a deaminase or a derivative deaminase (e.g., APOBEC3G) that retains at least one binding or deaminating function of the full length protein. By way of example, the fragment or derivative can include a Zinc-Dependent Cytidine Deaminase domain or can include 20, 30, 40, 50, 60, 70 80, 90% similarity with the full length deaminase. The fragment or derivative can include conservative or non-conservative amino acid substitutions. The fragment or derivative can include a linker sequence joining a catalytic domain (CD) to a pseudo-catalytic domain (PCD) and can have the domain structure CD-PCD-CD-PCD or any repeats thereof; this nomenclature has also been referred to as N-terminal catalytic domain (NTCD), N-terminal non-catalytic domain (NTNCD), C-terminal catalytic domain (CTCD) and C-terminal non-catalytic domain (CTNCD), which may be used interchangeably. The fragment or derivative can comprise a CD. Other fragments or derivatives are identified by structure-based sequence alignment (SBSA) as shown herein. Additionally, such fragments can be identified by volumetric alignment of the fundamental ZDD domain with the SAXS-derived structure using volume matching procedures.

Also disclosed are chimeric proteins, wherein the APOBEC3G fragment or derivative has at least 20, 30, 40, 50, 60, 70, 80, or 90% amino acid similarity with APOBEC3G.

Disclosed are APOBEC3G mimetics, wherein the mimetic promotes retention of the LMM form of APOBEC3G. The APOBEC3G mimetic can have a truncated form, for example, wherein the N-terminal ends are truncated.

Disclosed are auxiliary proteins, wherein the auxiliary proteins bind and regulate or determine the (i) binding of non-specific RNA that associates with APOBEC3G and promotes the HMM form of APOBEC3G; (ii) protein-protein interactions that are necessary for dimerization or other activities involved in the formation of HMM forms of APOBEC3G or (iii) the function of the LMM form of APOBEC3G in terms of the level or efficiency of the deamination reaction.

1. Sequence Similarities

It is understood that, as discussed herein, the use of the terms "homology" and "identity" are used interchangeably with "similarity" with regard to amino acid or nucleic acid sequences. Homology is further used to refer to similarities in secondary, tertiary, and quaternary structures. High primary sequence homology often translates into high three dimensional structural similarity. Therefore, both sequence homology and structural homology can be used to identify similarities in proteins.

In general, it is understood that one way to define any known variants and derivatives or those that might arise, of the disclosed genes and proteins herein, is through defining the variants and derivatives in terms of similarity to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent similarity to the stated sequence or the native sequence. Specifically disclosed are variants of APOBEC-3G and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent similarity to the stated sequence. Those of skill in the art readily understand how to determine the similarity of two proteins or nucleic acids, such as genes. For example, the similarity can be calculated after aligning the two sequences so that the similarity is at its highest level. Three dimensional structure can also be used to determine similarity.

Another way of calculating similarity can be performed by published algorithms. Optimal alignment of sequences for comparison may be conducted by the algorithm of Smith and Waterman Adv. Appl. Math. 2: 482 (1981), by the alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of similarity can be obtained for nucleic acids by for example the algorithms disclosed in Zuker, M. Science 244:48-52, 1989, Jaeger, Proc. Natl. Acad. Sci. USA 86:7706-7710, 1989, Jaeger, Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent similarity to another sequence refers to sequences that have the recited homology as calculated by any one or more of the calculation methods described above. For example, a first sequence has 80 percent similarity, as defined herein, to a second sequence if the first sequence is calculated to have 80 percent similarity to the second sequence using the Zuker calculation method even if the first sequence does not have 80 percent similarity to the second sequence as calculated by any of the other calculation methods. As another example, a first sequence has 80 percent similarity, as defined herein, to a second sequence if the first sequence is calculated to have 80 percent similarity to the second sequence using both the Zuker calculation method and the Pearson and Lipman calculation method even if the first sequence does not have 80 percent similarity to the second sequence as calculated by the Smith and Waterman calculation method, the Needleman and Wunsch calculation method, the Jaeger calculation methods, or any of the other calculation methods. As yet another example, a first sequence has 80 percent similarity, as defined herein, to a second sequence if the first sequence is calculated to have 80 percent similarity to the second sequence using each of calculation methods (although, in practice, the different calculation methods will often result in different calculated similarity percentages).

Other structural similarities, aside from sequence similarity are also disclosed. For example, homology, as noted by similar secondary, tertiary, and quaternary structure can be analyzed, as taught herein. Homologous proteins may have minimal sequence similarity but have a homologous catalytic domain. Thus, proteins as used herein may be structurally similar based on the structure of the catalytic domain or other domain but have lower than 70% sequence similarity.

2. Hybridization/Selective Hybridization

The term "hybridization" typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution [6×SSC (saline sodium citrate) or 6×SSPE (saline sodium phosphate/EDTA)] at a temperature that is about 5-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook, Molecular Cloning: A Laboratory Manual, 2nd Ed., Cold Spring Harbor Laboratory, Cold Spring Harbor, N.Y., 1989; Kunkel, Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with similarity, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

3. Compositions Identified by Screening with Disclosed Compositions/Combinatorial Chemistry a) Combinatorial Chemistry and Protein Mimetics Given the information herein molecules that function like the disclosed molecules can be identified and used as discussed herein. For example, the knowledge there are two forms of APOBEC3G (HMM and LMM) and that the LMM form is more enzymatically active in viral interaction, indicates targets for identifying molecules that will affect viral infectivity by promoting more of the LMM form of APOBEC3G. Disclosed are compositions and methods of making these compositions that promote the LMM form, or that block the formation of the HMM form of APOBEC3G. As discussed herein, this knowledge can be used along with, for example, combinatorial chemistry techniques, to identify molecules that function as desired, by for example, enhancing the LMM form of APOBEC3G.

The disclosed compositions, such as APOBEC3G, can be used as targets for any combinatorial or screening technique to identify molecules or macromolecular molecules that interact with the disclosed compositions in a desired way or mimic their function. The nucleic acids, peptides, and related molecules disclosed herein can be used as targets for the combinatorial approaches. Also disclosed are the compositions that are identified through combinatorial techniques or screening techniques in which the compositions disclosed, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function, or retention of one form over another. The molecules identified and isolated when using APOBEC3G (in either form) are also disclosed. Thus, the products produced using the combinatorial or screening approaches that involve APOBEC3G are also disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins that either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference in their entirety for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen (Cohen B. A., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, Nature 340:245-6 (1989)). Cohen modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example the N-terminal portion of LMM, is attached to a DNA binding domain of a transcriptional activation protein, such as Gal 4. By performing the two-hybrid technique on this type of system, molecules that bind the N-terminal portion of LMM can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cycfics (U.S. Pat. No. 5,958,792), biaryl amino acid amides (U.S. Pat. No. 5,948,696), thiophenes (U.S. Pat. No. 5,942,387), tricyclic tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interactive processes.

b) Computer Assisted Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, proteins and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function, or promote retention of one form over the other (such as retention of the LMM form). The molecules identified and isolated when using the disclosed compositions, such as the two forms of APOBEC3G, are also disclosed. Thus, the products produced using the molecular modeling approaches that involve the disclosed compositions, such as the two forms of APOBEC3G, are also considered herein disclosed.

Thus, one way to isolate molecules that bind a molecule of choice is through rational design. This can be achieved through structural information and computer modeling or in silico (virtual) ligand screening of virtual compound libraries based on those available from the NCI. Computer modeling technology allows visualization of the three-dimensional atomic structure of a selected molecule and the rational design of new compounds that will interact with the molecule. In silico screening using computational methods [e.g. as implemented in Sybyl (Tripos) or FlexX] to identify a lead compound by providing the best six dimensional fit of a virtual compound at a targeted area of the protein molecule, such as a protein-protein interaction interface. The three-dimensional construct typically depends on experimentally derived atomic coordinates derived from x-ray crystallographic analyses or NMR structure determination of the selected molecule. The computer graphics systems enable user-based or automated prediction of how a new compound will bind to the target molecule and allow experimental manipulation of the structures of the compound and target molecule to perfect binding specificity. Prediction of what the molecule-compound interaction will be when small changes are made in one or both requires molecular mechanics and/or molecular dynamics software (which requires force field parameters) implemented on a computationally intensive computer platform, usually coupled with user-friendly, graphical user interfaces (GUI) between the molecular design program and the user.

Examples of molecular modeling systems are the CHARMm and QUANTA programs, Polygen Corporation, Waltham, Mass. CHARMm performs energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen (1988) Acta Pharmaceutica Fennica 97, 159-166; Ripka, New Scientist 54-57 (Jun. 16, 1988); McKinaly and Rossmann, 1989 Annu. Rev. Pharmacol. Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, 1989 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds that could alter binding, one could also screen libraries of known compounds, including natural products or synthetic chemicals, and biologically active materials, including proteins, for compounds which alter substrate binding or enzymatic activity.

A compound that is identified or designed as a result of any of the disclosed methods can be obtained (or synthesized) and tested for its biological activity, e.g., interaction with either form of APOBEC3G or inhibition of HIV infectivity.

Also disclosed are compositions produced by any of the processes as disclosed herein, as well as compositions capable of being identified by the processes disclosed herein.

It is understood that the disclosed methods can be performed with libraries of molecules as well as a single molecule. Typically, if a library of molecules is being used, a step of separating the molecules within the library that, for example, enhances LMM functionality, from those that do not, can be used. This step of separation can be performed in a number of ways, including for example, through various chromatography means, including column chromatography, as well as using high through put mechanism, such as affinity sorting fluorescence analysis or fluorescence activated cell sorting (FACS) by flow cytometry. Another method is to determine the structure of the protein in the presence of compound pools. The high resolution structure will reveal the binding of certain compounds that may provide the desired effect on molecular function (e.g. blocking RNA binding to LMM particles). Subsequent deconvolution of compounds from a given pool can identify lead compound that can be adapted through organic chemistry for tighter binding [Nienaber et al. *Nature Biotechnology* 18, 1105-1108 (2000)]

4. Peptides
  a) Protein Variants
  As discussed herein there are numerous variants of APOBEC3G that are known and herein contemplated, as well as two distinct forms of APOBEC3G (HMM and LMM). In addition to the known functional APOBEC3G strain variants there are derivatives of the APOBEC3G proteins that also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations generally do not place the sequence out of reading frame (unless the resulting missense and/or truncations are desired) and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

| Amino Acid Abbreviations | |
|---|---|
| Amino Acid | Abbreviations |
| Alanine | Ala; A |
| Arginine | Arg; R |
| Asparagine | Asn; N |
| Aspartic acid | Asp; D |
| Cysteine | Cys; C |
| Glutamic acid | Glu; E |
| Glutamine | Gln; Q |
| Glycine | Gly; G |
| Histidine | His; H |
| Isoleucine | Ile; I |
| Leucine | Leu; L |
| Lysine | Lys; K |
| Methionine | Met; M |
| Phenylalanine | Phe; F |
| Proline | Pro; P |
| Serine | Ser; S |
| Threonine | Thr; T |
| Tyrosine | Tyr; Y |
| Tryptophan | Trp; W |
| Valine | Val; V |

TABLE 2

Amino Acid Substitutions
Original Residue Exemplary Conservative Substitutions

Ala; Ser
Arg; Lys; Gln
Asn; Gln; His
Asp; Glu
Cys; Ser
Gln; Asn, Lys
Glu; Asp
Gly; Pro
His; Asn; Gln
Ile; Leu; Val
Leu; Ile; Val
Lys; Arg; Gln;
Met; Leu; Ile
Phe; Met; Leu; Tyr
Ser; Thr
Thr; Ser
Trp; Tyr
Tyr; Trp; Phe
Val; Ile; Leu

Substantial changes in function or immunological identity can be made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine (only in the case of a disulfide bond, but Cys-to-Ser mutations are common) or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the epsilon amino groups of lysine, the guanidinium group of arginine, or the imidizole ring of histidine side chains (T.E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of proteins herein disclosed which have at least, 70% or 75% or 80% or 85% or 90% or 95% similarity to the stated sequence. Those of skill in the art readily understand how to determine the similarity of two proteins. For example, the similarity can be calculated after aligning the two sequences so that the similarity is at its highest level or by a variety of methods described above.

Another way of calculating similarity can be performed by published algorithms. Optimal alignment of sequences for comparison may be conducted by the local algorithm of Smith and Waterman Adv. Appl. Math. 2: 482 (1981), by the alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of similarity can be obtained for nucleic acids by for example the algorithms disclosed in Zuker, M. Science 244:48-52, 1989, Jaeger Proc. Natl. Acad. Sci. USA 86:7706-7710, 1989, Jaeger Methods Enzymol. 183:281-306, 1989, which are herein incorporated by reference for at least material related to nucleic acid alignment.

It is understood that the description of conservative mutations and similarity can be combined together in any combination, such as embodiments that have at least 70% similarity to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. Provided herein are all degenerate variants of the nucleic acid sequences and all amino acids sequences with conservative amino acid substitutions.

It is understood that there are numerous amino acid and peptide analogs which can be incorporated into the disclosed compositions. For example, there are numerous D amino acids or amino acids which have a different functional substituent than the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill TIES, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2$—$CH_2$—$CH$=$CH$—(cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. Int J Pept Prot Res 14:177-185 (1979) (—$CH_2NH$—, $CH_2CH_2$—); Spatola, Life Sci 38:1243-1249 (1986) (—$CH H_2$—S); Hann J. Chem. Soc Perkin Trans. I 307-314 (1982) (—CH—CH—, cis and trans); Almquist, J. Med. Chem. 23:1392-1398 (1980) (—$COCH_2$—); Jennings-White, Tetrahedron Lett 23:2533 (1982) (—$COCH_2$—); Szelke, European Appin, EP 45665 CA (1982): 97:39405 (1982) (—$CH(OH)CH_2$—); Holladay, Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

5. Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, riboswitches, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with, for example, the RNA associated with the HMM of APOBEC3G, or the HMM molecule, or the LMM molecule, or any other disclosed molecule, or the genomic DNA of APOBEC3G, or any other disclosed molecule or they can interact with the polypeptide APOBEC3G, in either form, or any other disclosed molecule. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary or quaternary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (kD) less than 10-6. It is more preferred that antisense molecules bind with a kD less than 10-8. It is also more preferred that the antisense molecules bind the target molecule with a kD less than 10-10. It is also preferred that the antisense molecules bind the target molecule with a kD less than 10-12. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with kDs from the target molecule of less than 10-12 M. It is preferred that the aptamers bind the target molecule with a kD less than 10-6. It is more preferred that the aptamers bind the target molecule with a kD less than 10-8. It is also more preferred that the aptamers bind the target molecule with a kD less than 10-10. It is also preferred that the aptamers bind the target molecule with a kD less than 10-12. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a kD with the target molecule at least 10 fold lower than the kD with a background binding molecule. It is more preferred that the aptamer have a kD with the target molecule at least 100 fold lower than the kD with a background binding molecule. It is more preferred that the aptamer have a kD with the target molecule at least 1000 fold lower than the kD with a background binding molecule. It is preferred that the aptamer have a kD with the target molecule at least 10000 fold lower than the kD with a background binding molecule. It is preferred when doing the comparison for a polypeptide for example, that the background molecule be a different polypeptide. For example, when determining the specificity of APOBEC3G, or any other disclosed molecule aptamers, the background protein could be serum albumin. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Riboswitches are molecules that are comparable to aptamers except that they are naturally occurring RNAs that bind a metabolite. Such binding often sequesters the metabolite and can affect the structure of mRNA, thereby disrupting or stimulating protein translation. Some riboswitches are also ribozymes. For example, the naturally occurring glmS riboswitch binds the metabolite glucosamine-6-phosphate, which is the product of the enzyme encoded by the glmS gene. Binding of glucosamine-6-phosphate by the ribozyme results in cleavage of the glmS message in a chemical mechanism whereby the amine group of the metabolite directly participates in the chemical steps of the reaction. This process provides a means of modulating the production of glucosamine-6-phosphate in the cell.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with an equilibrium dissociation constant, $K_D$ less than $10^{-6}$M. It is more preferred that the triplex forming molecules bind with a $K_D$ less than $10^{-8}$ M. It is also more preferred that the triplex forming molecules bind the target molecule with a $K_D$ less than $10^{-10}$ M. It is also preferred that the triplex forming molecules bind the target molecule with a $K_D$ less than $10^{-12}$ M. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukaryotic cells. (Yuan, Proc. Natl. Acad. Sci. USA 89:8006-8010 (1992); WO 93/22434 by Yale; WO 95/24489 by Yale; Yuan and Altman, EMBO J 14:159-168 (1995), and Carrara, Proc. Natl. Acad. Sci. (USA) 92:2627-2631 (1995)). Representative examples of how to make and use EGS molecules to facilitate cleavage of a variety of different target molecules can be found in the following non-limiting list of U.S. Pat. Nos. 5,168,053, 5,624,824, 5,683,873, 5,728,521, 5,869,248, and 5,877,162.

6. Delivery of the Compositions to Cells

The disclosed proteins and compositions can be delivered to the target cells in a variety of ways. The peptides and mimetics disclosed herein can be added directly to cells in culture or injected into the body, or can be used in a chimeric protein to transduce the cell membrane and into the cell's interior. Alternatively, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham, Am. J. Resp. Cell. Mol. Biol. 1:95-100 (1989); Feigner, Proc. Natl. Acad. Sci. USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

7. Nucleic Acids

There are a variety of molecules disclosed herein that are nucleic acid based, including for example the nucleic acids that encode APOBEC3G, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenine-9-yl (A), cytosine-1-yl (C), guanine-9-yl (G), uracil-1-yl (U), and thymine-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide that contains some type of modification to either the base, sugar, or phosphate moieties. Modifications to the base moiety would include natural and synthetic modifications of A, C, G, and T/U as well as different purine or pyrimidine bases, such as uracil-5-yl ($\psi$), hypoxanthine-9-yl (I), and 2-aminoadenine-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[($CH_2$)$_n$ O]$_m$, $CH_3$, —O($CH_2$)$_n$ $OCH_3$, —O($CH_2$)$_n$ $NH_2$, —O($CH_2$)$_n$ $CH_3$, —O($CH_2$)$_n$—$ONH_2$, and —O($CH_2$)$_n$ON [($CH_2$)$_n$ $CH_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen, Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger, Proc. Natl. Acad. Sci. USA, 1989, 86, 6553-6556), cholic acid (Manoharan, Bioorg. Med. Chem. Let., 1994, 4, 1053-1060), a thioether, e.g., hexyl-5-tritylthiol (Manoharan, Ann. N.Y. Acad. Sci., 1992, 660, 306-309; Manoharan, Bioorg. Med. Chem. Let., 1993, 3, 2765-2770), a thiocholesterol (Oberhauser, Nucl. Acids Res., 1992, 20, 533-538), an aliphatic chain, e.g., dodecandiol or undecyl residues (Saison-Behmoaras, EMBO J., 1991, 10, 1111-1118; Kabanov, FEBS Lett., 1990, 259, 327-330; Svinarchuk, Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan, Tetrahedron Lett., 1995, 36, 3651-3654; Shea., Nucl. Acids Res., 1990, 18, 3777-3783), a polyamine or a polyethylene glycol chain (Manoharan, Nucleosides & Nucleotides, 1995, 14, 969-973), or adamantane acetic acid (Manoharan, Tetrahedron Lett., 1995, 36, 3651-3654), a palmityl moiety (Mishra, Biochim. Biophys. Acta, 1995, 1264, 229-237), or an octadecylamine or hexylamino-carbonyl-oxycholesterol moiety (Crooke, J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA or RNA. The Hoogsteen face includes the N7 position and reactive groups ($NH_2$ or O) at the C6 position of purine nucleotides.

8. Antibodies a) Antibodies Generally

Also disclosed are antibodies to APOBEC3G or any portion thereof, or to either of the specific forms of APOBEC3G such as HMM or LMM. As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as scFv, sFv, F(ab')2, Fab', Fab and the like, including hybrid fragments. Thus, fragments of the antibodies that retain the ability to bind their specific antigens are provided. For example, fragments of antibodies which maintain the LMM form of APOBEC3G are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane, Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits, Proc. Natl. Acad. Sci. USA, 90:2551-255 (1993); Jakobovits, Nature, 362:255-258 (1993); Bruggemann, Year in Immuno., 7:33 (1993)). Human antibodies can also be produced in phage display libraries (Hoogenboom, J. Mol. Biol., 227:381 (1991); Marks, J. Mol. Biol., 222:581 (1991)). The techniques of Cole and Boerner are also available for the preparation of human monoclonal antibodies (Cole, Monoclonal Antibodies and Cancer Therapy, Alan R. Liss, p. 77 (1985); Boerner, J. Immunol., 147(1):86-95 (1991)).

Also disclosed are hybridoma cells that produce the disclosed monoclonal antibodies. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison, Proc. Natl. Acad. Sci. USA, 81:6851-6855 (1984)).

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur, "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against HMM, for example. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal. The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the disclosed monoclonal antibodies can be readily isolated and sequenced using conventional procedures (e.g., by using oligonucleotide probes that are capable of binding specifically to genes encoding the heavy and light chains of murine antibodies). The disclosed hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of a disclosed antibody or substituted for the variable domains of one antigen-combining site of a disclosed antibody to create a chimeric bivalent antibody comprising one antigen-combining site having specificity for one and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the disclosed antibodies or chimeric proteins is to link two or more peptides or polypeptides together by protein chemistry techniques described herein.

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane, Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson, Anal. Biochem., 107:220 (1980).

Also provided is an antibody reagent kit comprising containers of the disclosed monoclonal antibody or fragment thereof and one or more reagents for detecting binding of the antibody or fragment thereof. The reagents can include, for example, fluorescent tags, enzymatic tags, or other tags. The reagents can also include secondary or tertiary antibodies or reagents for enzymatic reactions, wherein the enzymatic reactions produce a product that can be visualized.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

b) Human Antibodies

The disclosed human antibodies can be prepared using any technique. Examples of techniques for human monoclonal antibody production include those described by Cole (*Monoclonal Antibodies and Cancer Therapy*, Alan R. Liss, p. 77, 1985) and by Boerner (*J. Immunol.*, 147(1):86-95, 1991). The disclosed human antibodies (and fragments thereof) can also be produced using phage display libraries (Hoogenboom, J. Mol. Biol., 227:381, 1991; Marks, J. Mol. Biol., 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits, Proc. Natl. Acad. Sci. USA, 90:2551-255 (1993); Jakobovits, Nature, 362:255-258 (1993); Bruggermann, Year in Immunol. 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

c) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fc, Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones, Nature, 321:522-525 (1986), Reichmann, Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones, Nature, 321:522-525 (1986), Riechmann, Nature, 332:323-327 (1988), Verhoeyen, Science, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly), U.S. Pat. No. 5,565,332 (Hoogenboom), U.S. Pat. No. 5,721,367 (Kay), U.S. Pat. No. 5,837,243 (Deo), U.S. Pat. No. 5,939,598 (Kucherlapati), U.S. Pat. No. 6,130,364 (Jakobovits), and U.S. Pat. No. 6,180,377 (Morgan).

d) Administration of Antibodies

The disclosed antibodies preferably can be administered to a subject in a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. Local or intravenous injection is preferred. Furthermore, ex vivo administration can be used wherein cells or tissues are isolated, treated, and returned to the subject to be treated.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., Handbook of Monoclonal Antibodies, Ferrone, eds., Noges Publications, Park Ridge, N.J., (1985) ch. 22 and pp. 303-357; Smith, Antibodies in Human Diagnosis and Therapy, Haber, eds., Raven Press, New York (1977) pp. 365-389. A typical daily dosage of the antibody used alone might range from about 1 µg/kg to up to 100 mg/kg of body weight or more per day, depending on the factors mentioned above.

Following administration of an antibody for treating, inhibiting, or preventing an HIV infection, the efficacy of the therapeutic antibody can be assessed in various ways well known to the skilled practitioner. For instance, one of ordinary skill in the art will understand that an antibody as disclosed can be efficacious in treating or inhibiting an HIV infection in a subject by observing that the antibody reduces viral load or prevents a further increase in viral load. Viral loads can be measured by methods that are known in the art, for example, using polymerase chain reaction assays to detect the presence of HIV nucleic acid or antibody assays to detect the presence of HIV protein in a sample (e.g., but not limited to, blood) from a subject or patient, or by measuring the level of circulating anti-HIV antibody levels in the patient. Efficacy of the antibody treatment may also be determined by measuring the number of $CD4^+$ T cells in the HIV-infected subject. An antibody treatment that inhibits an initial or further decrease in $CD4^+$ T cells in an HIV-positive subject or patient, or that results in an increase in the number of $CD4^+$ T cells in the HIV-positive subject, is an efficacious antibody treatment.

Antibodies disclosed herein can also be used to detect various of the disclosed compounds. Such antibodies can be used for research and clinical purposes.

9. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, Bioconjugate Chem., 2:447-451, (1991); Bagshawe, K. D., Br. J. Cancer, 60:275-281, (1989); Bagshawe, Br. J. Cancer, 58:700-703, (1988); Senter, Bioconjugate Chem., 4:3-9, (1993); Battelli, Cancer Immunol. Immunother., 35:421-425, (1992); Pietersz and McKenzie, Immunolog. Reviews, 129:57-80, (1992); and Roffler, Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes, Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release. This liposome delivery system can also be made to target B cells by incorporating into the liposome structure a ligand having an affinity for B cell-specific receptors.

Compositions including the liposomes in a pharmaceutically acceptable carrier are also contemplated.

Transdermal delivery devices have been employed for delivery of low molecular weight proteins by using lipid-based compositions (i.e., in the form of a patch) in combination with sonophoresis. However, as reported in U.S. Pat. No. 6,041,253 to Ellinwood, Jr. et al., which is hereby incorporated by reference in its entirety, transdermal delivery can be further enhanced by the application of an electric field, for example, by ionophoresis or electroporation. Using low frequency ultrasound which induces cavitation of the lipid layers of the stratum corneum, higher transdermal fluxes, rapid control of transdermal fluxes, and drug delivery at lower ultrasound intensities can be achieved. Still further enhancement can be obtained using a combination of chemical enhancers and/or magnetic field along with the electric field and ultrasound.

Implantable or injectable protein depot compositions can also be employed, providing long-term delivery of, e.g., the first and second chimeric proteins. For example, U.S. Pat. No. 6,331,311 to Brodbeck, which is hereby incorporated by reference in its entirety, reports an injectable depot gel composition which includes a biocompatible polymer, a solvent that dissolves the polymer and forms a viscous gel, and an emulsifying agent in the form of a dispersed droplet phase in the viscous gel. Upon injection, such a gel composition can provide a relatively continuous rate of dispersion of the agent to be delivered, thereby avoiding an initial burst of the agent to be delivered.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

a) Pharmaceutically Acceptable Carriers

By "delivery of the protein into a cell" is meant contacting the cell with the protein under conditions effective for cellular uptake of the c protein. Such delivery occurs in the absence of genetically modifying the cell. This provides a significant advantage over gene therapy as the delivery can be controlled in a dose-dependent fashion, is adaptable to variations in the subject's needs, protein administration is reversible, and is generally more acceptable to a subject.

Disclosed are compositions comprising a protein and a pharmaceutical carrier. Such compositions can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including opthamalically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any contraindications. Dosage can vary, and can be administered in one or more dose administrations daily, for one or several days. While individual needs vary, determination of optimal ranges of effective amounts of each of the first and second chimeric proteins is within the skill of the art. Typical dosages comprise about 0.01 to about 100 mg/kg·body wt. The preferred dosages comprise about 0.1 to about 100 mg/kg·body wt. The most preferred dosages comprise about 1 to about 100 mg/kg·body wt.

Other chimeric proteins or mimetics which do not have a specific pharmaceutical function, but which may be used for tracking changes within cellular chromosomes or for the delivery of diagnostic tools for example can be delivered in ways similar to those described for the pharmaceutical products.

The chimeric proteins can also be used for example as tools to isolate and test new drug candidates for a variety of diseases.

10. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

11. Computer Readable Media

It is understood that the disclosed nucleic acids and proteins can be represented as a sequence consisting of the nucleotides or amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable media comprising the sequences and information regarding the sequences set forth herein.

12. Kits

Disclosed herein are kits that are drawn to reagents (e.g., peptides, drugs, or mimetics) that can be used in practicing the methods disclosed herein. The kits can include any reagent or combination of reagent discussed herein or that would be understood to be required or beneficial in the practice of the disclosed methods.

13. Compositions with Similar Functions

It is understood that the compositions disclosed herein have certain functions, for example, RNA editing and/or DNA mutation (editing), or interacting with the various forms of APOBEC3G. Disclosed herein are certain structural requirements for performing the disclosed functions, and it is understood that there are a variety of structures which can perform the same function which are related to the disclosed structures, and that these structures will ultimately achieve the same results as previously described.

D. Methods of Using the Compositions

As defined herein, an "LMM enhancing substance" refers to any peptide, nucleic acid, mimetic, compound, or drug that increases the formation or retention of the LMM form of APOBEC3G, or that reduces or prevents HMM formation. By "increasing retention of the LMM form" is meant that LMM is allowed to retain its form and not be converted to the HMM form to the degree found in a control or in an unregulated cell. The LMM enhancing substance can also reduce or prevent HMM formation by blocking, preventing, or inhibiting the processes and associated peptides and nucleic acids that are necessary for the formation of the HMM form. By "reduce or prevent HMM formation" is meant that the substance can block, inhibit, decrease, or slow the formation of HMM from LMM molecules. It can also mean that the substance increases the degradation or sequesters HMM so that it cannot interfere with the action of LMM.

As used herein, the term "HMM conversion molecules" refers to those substances, including peptides, polypeptides, proteins, mimetics, analogs, nucleic acids, antibodies, pharmaceutical compositions, chemical compositions, and compounds that interact with LMM to convert it to HMM, either directly or indirectly, or that interact with HMM to stabilize it, thereby increasing its half life.

Disclosed are methods for enhancing, sustaining, increasing, or promoting the LMM form of APOBEC3G. Also disclosed are methods of reducing interactions between LMM and those proteins and nucleic acid molecules that associate with it in order to convert the LMM form to HMM. These methods can comprise, for example, a step of incubating an inhibitor of the interaction between LMM and HMM conversion molecules. Also disclosed are methods for inhibiting HIV infectivity comprising administering an inhibitor of the interaction between LMM and HMM conversion molecules.

Disclosed are methods of treating a subject comprising administering to the subject an inhibitor of viral infectivity (e.g., HIV infectivity), wherein the inhibitor reduces the interaction between LMM and HMM conversion molecules, and wherein the subject is in need of such treatment. Disclosed are methods of identifying an inhibitor of an interaction with APOBEC3G, in either form, that causes it to aggregate into the HMM form. Such a method can comprise, for example, the steps of incubating a library of molecules with APOBEC3G (in either form) to form a mixture, and identifying the molecules that disrupt the interaction between LMM and HMM conversion molecules. An isolating step can comprise incubating the mixture with a molecule comprising LMM or HMM or a fragment or derivative thereof.

Also disclosed are methods of treating a subject comprising administering to the subject an inhibitor of viral infectivity (e.g., HIV infectivity), wherein the inhibitor interacts with HMM to destroy or sequester it, wherein the subject is in need of such treatment. Disclosed are methods of identifying an inhibitor of HMM. Such a method can comprise, for example, the steps of incubating a library of molecules with HMM to form a mixture, and identifying the molecules interact with HMM, and, optionally, those which can degrade, destroy, or sequester HMM. An isolating step can comprise incubating the mixture with HMM or a fragment or derivative thereof.

Disclosed are methods of identifying an inhibitor of an interaction between LMM (or HMM) and HMM conversion molecules, comprising incubating a library of molecules with APOBEC3G (in either form) to form a mixture, and identifying the molecules that disrupt the interaction between LMM (or HMM) and HMM conversion molecules. The interaction disrupted can comprise an interaction between LMM and HMM conversion molecules, or can comprise an interaction between HMM and HMM conversion molecules. An isolation step can comprises incubating the mixture with a molecule comprising APOBEC3G (in either form) or fragment or derivative thereof.

By "interrupting viral infectivity" is meant stopping or reducing the production of infective viral genomes. HIV infectivity, for example, is known to depend on a variety of proteins leading to the synthesis of double stranded DNA from single stranded HIV RNA genome and the integration of HIV DNA into the host cell's chromosomal DNA from where it is expressed to form viral genomes and viral proteins necessary for virion production.

Disclosed are methods of interrupting viral infectivity (e.g., retroviral infectivity like HIV infectivity) comprising contacting an infected cell or a cell prior to infection with an LMM enhancing substance, under conditions that allow delivery of the LMM enhancing substance into the cell, wherein the LMM enhancing substance allows for LMM to continue to interrupt viral infectivity. Interruption of viral infectivity may occur at the different level, including, for example, at the level of RNA on the incoming virus, on first or second strand cDNA, after dsDNA integration and/or on transcripts from the viral integrin.

Disclosed are methods of treating a subject with a viral infection (e.g., HIV infection) or at risk for an infection comprising administering to the subject an effective amount of an LMM enhancing substance. Preferably, the administration step is dose-dependent and transient. As used throughout, administration of a protein or agent described herein can be combined with various others therapies. For example, a subject with HIV may be treated concomitantly with protease inhibitors and other agents.

As discussed and described further elsewhere herein, some forms of LMM enhancing substances can modulate, block or otherwise interfere with interaction of APOBEC3G subunits and/or RNA or other multimerization factors to form the HMM form of APOBEC3G. The disclosed structures of HMM and LMM indicate areas of the APOBEC3G subunit that can be targeted for binding or interaction with LMM enhancing substances. Such areas can also serve as the basis for peptides and other structural analogs or mimetics that can interact with LMM forms to reduce or prevent formation of HMM. For example, a peptide derived from a region of the APOBEC3G subunit that contacts another APOBEC3G subunit or associated RNA in HMM but not in LMM, or a mimetic of such a peptide, can be used to compete with APOBEC3G subunits for contacts needed to form HMM, thus reducing or preventing HMM formation. As another example, nucleic acids that can bind to APOBEC3G-associated RNA in a region needed for formation of HMM, thus reducing or preventing HMM formation, can be used as LMM enhancing substances.

In the LMM oligomeric state the N-terminal catalytic domains do not interact with one another (dimerized) and given their role in RNA binding in vitro, can bind RNA in the formation of HMM. This does not exclude the possibility that the C-terminal catalytic domains, the N-terminal pseudo catalytic domains, the C-terminal pseudo catalytic domains or any other part of the APOBEC3G subunit can bind RNA or that RNA binding is further induced or enhanced along the APOBEC3G subunit during formation of the HMM particle. RNA oligonucleotides, DNA oligonucleotides or peptides that bind to the N-terminal catalytic domain will compete for cellular or viral RNA binding to the N-terminal domain and prevent or destabilize the formation of HMM. Protein-protein interactions are also critical to the formation of HMM. Protein-protein interaction between the C-terminal pseudo catalytic domains (i.e. the last 50-55 amino acids of hA3G) is essential for formation of tail-to-tail dimers of A3G (LMM) and this interaction persists in HMM particles. Since subunit dimerization is key in the enzyme's processive DNA deaminase activity, RNA oligonucleotides, DNA oligonucleotides or peptides that stabilize the subunit interaction are predicted to preserve or enhance antiviral catalytic activity of APOBEC3G. An interaction of the N-terminal pseudo catalytic domain of one subunit within LMM with the C-terminal pseudo catalytic domain of another subunit in an adjacent LMM are predicted as stabilizing the dimerization of dimers (multiple LMM particles) leading to HMM particles. Hence, RNA oligonucleotides, DNA oligonucleotides or peptides that can interact with the N-terminal or C-terminal pseudo catalytic domains are predicted to destabilize or prevent HMM formation. The HMM structure predicts that APOBEC3G dimers are aligned in the HMM structure such that the N-terminal catalytic domains of adjacent molecules are not face to face with one another but are staggered such that protein-protein interactions occur through NTPCD and CTPCD interactions related through and approximate dyad axis of symmetry (FIG. 3A). In this case RNA oligonucleotides, DNA oligonucleotides or peptides that can interact with the N-terminal pseudo catalytic domain or C-terminal pseudo catalytic domain can destabilize or prevent HMM formation. The preceding is meant as an example of the design of therapeutics derived from protein surfaces that appear to be aligned in the HMM and LMM structures.

Also disclosed are methods that include mixing a pharmaceutical carrier with the inhibitor as disclosed herein and produced by any of the disclosed methods.

By "an agent that enhances the efficiency of editing" is meant a genetic, pharmacologic, or metabolic agent or condition that increases the RNA or DNA editing or mutating function of the chimeric protein, as compared to the amount of editing that occurs in the absence of the agent. Some of the conditions and agents that modulate editing activity include: (i) changes in the diet, (ii) hormonal changes (e.g., levels of insulin or thyroid hormone), (iv) osmolarity (e.g., hyper or hypo osmolarity), (v) ethanol, (vi) inhibitors of RNA or protein synthesis and (vii) conditions that promote liver proliferation. Thus, the disclosed methods can further comprise administering to the subject an agent that enhances the efficiency of mRNA editing function of the chimeric protein.

Disclosed are methods of treating a condition in a subject comprising administering to the subject an LMM enhancing substance. It is understood that the effect of the administration of the composition to the subject can have the effect of but is not limited to reducing the symptoms of the condition, a reduction in the severity of the condition, or the complete ablation of the condition.

1. Methods of Using the Compositions as Research Tools

The disclosed compositions can be used in a variety of ways as research tools. For example, the disclosed compositions, such as APOBEC3G in either form, can be used to study the interactions between LMM and virions or T-cells, or the interactions between HMM and its associated proteins and RNA, or the interaction that occurs to convert LMM molecules to HMM molecules.

The compositions can be used for example as targets in combinatorial chemistry protocols or other screening protocols to isolate molecules that possess desired functional properties related to enhancing LMM functionality or amounts.

The disclosed compositions can be used as discussed herein as either reagents in microarrays or as reagents to probe or analyze existing microarrays. The disclosed compositions can be used in any known method for isolating or identifying single nucleotide polymorphisms. The compositions can also be used in any method for determining allelic analysis. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

Disclosed are methods of screening for an LMM enhancing substance comprising adding the agent to be screened to a virally infected mammalian system and detecting levels of edited viral RNA and/or mutated (edited) viral DNA, elevated levels of edited viral RNA or mutated (edited) viral DNA indicating a LMM-enhancing substance. By "elevated levels" is meant levels above that of a control system in which the LMM-enhancing substance is not present.

The virus can be a retrovirus (e.g., HIV). The virus can be an RNA virus. Also disclosed are methods, wherein the RNA virus can be selected from the list of viruses consisting of Vesicular stomatitis virus, Hepatitis A virus, Hepatitis C virus, Rhinovirus, Coronavirus, Influenza virus A, Influenza virus B, Measles virus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Hantavirus, and Rubella virus.

Disclosed are methods of identifying HMM conversion molecules comprising: a) incubating a library of potential HMM conversion molecules with LMM to form a mixture, and b) identifying the molecules that cause LMM to aggregate to the HMM form, thereby identifying HMM conversion molecules.

Also disclosed are methods of identifying HMM conversion molecules comprising: a) incubating a library of potential HMM conversion molecules with HMM to form a mixture, and b) identifying the molecules that stabilize the HMM form, thereby identifying HMM conversion molecules.

Also disclosed are methods of identifying inhibitors of HMM conversion molecules comprising: a) incubating the following: i) a library of potential inhibitors of HMM conversion molecules; ii) LMM; and iii) HMM conversion molecules to form a mixture, and b) identifying the molecules that disrupt the interaction between LMM and HMM conversion molecules, thereby identifying inhibitors of HMM conversion molecules.

Also disclosed are methods of treating a subject with or at risk of having a viral infection, comprising administering to the subject an inhibitor of viral infectivity, wherein the inhibitor interacts with HMM to destroy or sequester it, wherein the subject is in need of such treatment.

Also disclosed are methods of identifying an inhibitor of HMM comprising: a) incubating the following: i) a library of potential inhibitors of HMM, and ii) HMM to form a mixture, and b) identifying from the library of potential inhibitors of HMM those molecules that interact with HMM; and c) testing those molecules that interact with HMM to determine those that inhibit HMM, thereby identifying an inhibitor of HMM. For example, the inhibitor of HMM can degrade, destroy, or sequester HMM.

Also disclosed is a method of screening for an LMM enhancing substance comprising adding the agent to be screened to a virally infected mammalian system and detecting levels of edited viral RNA, elevated levels of edited viral RNA indicating a LMM-enhancing substance. Also disclosed are methods of using computer readable media to analyze a comparison sequence.

E. Methods of Making the Compositions

The compositions disclosed herein and the compositions necessary to perform the disclosed methods can be made using any method known to those of skill in the art for that particular reagent or compound unless otherwise specifically noted.

Disclosed are methods of manufacturing a composition for (e.g., APOBEC3G in either the HMM or LMM form, or an LMM enhancing substance) comprising synthesizing the inhibitors as disclosed herein.

Disclosed are methods of making a composition capable of inhibiting infectivity (e.g., HIV infectivity) comprising admixing a compound with a pharmaceutically acceptable carrier, wherein the compound is identified by administering the compound to a system, wherein the system supports infectivity via a deaminase interaction, assaying the effect of the compound on the amount of infectivity in the system, and selecting a compound which causes a decrease in the amount of infectivity in the system because of an inhibition of the deaminase interaction, relative to the system without the addition of the compound.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook *Molecular Cloning: A Laboratory Manual,* 2nd Edition (Cold Spring Harbor Laboratory Press, Cold Spring Harbor, N.Y., 1989, Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta, Ann. Rev. Biochem. 53:323-356 (1984), (phosphotriester and phosphite-triester methods), and Narang, Methods Enzymol., 65:610-620 (1980), (phosphotriester method). Protein nucleic acid molecules can be made using known methods such as those described by Nielsen, Bioconjug. Chem. 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L, Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson, Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M (1992) FEBS Lett. 307:97-101; Clark-Lewis I, J. Biol. Chem., 269: 16075 (1994); Clark-Lewis I., Biochemistry, 30:3128 (1991); Rajarathnam K., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M Science, 256:221 (1992)). This technique has been used to synthesize analogs of protein domains as well as large amounts of relatively pure proteins with full biological activity (deLisle Milton R C, Techniques in Protein Chemistry IV. Academic Press, New York, pp. 257-267 (1992)).

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Nanostructures of APOBEC3G Support a Hierarchical Assembly Model of High Molecular Mass Ribonucleoprotein Particles from Dimeric Subunits a) Experimental Procedures Preparation of hA3G Full—length hA3G cDNA was amplified from oligo-dT primed H9 cell RNA and a four His tag (4×His) was added to the C-terminus by PCR. This construct was subcloned into pFastbac™ (Invitrogen, CA). Baculovirus production and infection of Sf9 cell cultures for expression were carried out by Immunodiagnostics, Inc.

Frozen cells (4 g) where lysed in 20 mL of 0.5×hA3G buffer [1×=50 mM HEPPS pH 8.8, 75 mM NaCl, 10 mM $MgCl_2$, 5% (v/v) glycerol, 0.2 mM β-mercaptoethanol and EDTA-free complete protease inhibitor (Roche, Ind.)] by freezing in $N_2$ (l) and thawing followed by shearing via successive passes through 22 and 26 gauge needles. The lysis solution was brought to 1% (v/v) Triton X100 and made 0.1 mM in $CaCl_2$. Nuclease digestion ensued with either 0.125 mg/mL RNase-free DNase I (Sigma, Mo.) (hereafter this protein is referred to as hA3G-D) or 0.125 mg/mL DNase 1 and 0.25 mg/mL RNase A (Sigma) (hA3G-DR) at 37° C. for 30 min. The sample was brought to 1 M urea final concentration, incubated at 24° C. for 20 min and centrifuged (10K×g for 10 min at 24° C.). Cleared supernatants were adsorbed onto 2 mL Ni-NTA agarose (Qiagen, Germany) and mixed for 2 h at 24° C. Contaminants were removed by centrifugation of resin (500×g for 5 min) washed consecutively over a 2 h period with 10 volumes of: (i) 1×hA3G buffer with 1M urea; (ii) 1×hA3G buffer with 0.5M urea; (iii) 5×hA3G buffer; (iv) 1×hA3G buffer containing 0.010 M imidazole; and (v) 1×hA3G buffer with 0.070 M imidazole. Remaining Ni-NTA-bound hA3G was placed in a 15 mL Econo column (BioRad, CA) and eluted with 1× hA3G buffer with 0.25 M imidazole. Elution was monitored at 280 nm. Pure fractions were identified and pooled based on SDS PAGE gels stained with Coomassie blue dye; estimated purity was >99%. Samples were centrifuged at 50K×g for 60 min after purification. DNA deaminase assays (Supplemental Methods (below) and FIG. 4) demonstrated nominal activity for hA3G-D, whereas hA3G-DR produced a specific activity of 30 μmol $μg^{-1}$ $min^{-1}$. These activity trends are consistent with those reported (Chelico et al. 2006).

SAXS Experiments—Scattering experiments were performed at beamline G1 of CHESS (Ithaca, N.Y.). Scattered X-rays were recorded on a custom 1024×1024 (69.78 μm) pixel CCD detector fabricated by the Gruner group (Cornell University, NY). Scattering was performed at 20° C. at a sample-to-detector distance of 138.0 cm. The wavelength, λ, was 1.249 Å, which produced an accessible q-range from 0.012 to 0.215 $Å^{-1}$, where q=4π sin θ/λ (2θ is the scattering angle). Samples of hA3G were prepared at various concentrations in 1× hA3G buffer containing 0.250 M imidazole. Protein concentrations were 0.9 mg·$mL^{-1}$ and 1.8 mg·$mL^{-1}$ for hA3G-D, and 0.55 mg·$mL^{-1}$ and 1.1 mg·$mL^{-1}$ for hA3G-DR; lower concentrations were examined as well to assure there was no aggregation. Samples were centrifuged at 14K×g and immediately transferred to a home-made cuvette composed of a plastic micro-machined disk (ALine Inc, CA) fitted with 25 μm mica walls. This cell had a capacity of 12 μL and was loaded through an inlet port with a 25 μL blunt-end syringe (Hamilton Corp., NV). The X-ray beam size was 0.5×0.5 $mm^2$, which was significantly smaller than the sample cell window. Exposure times were 2 to 80 sec to assess radiation damage; each exposure was recorded in triplicate. Two-dimensional scattering data were corrected for buffer scatter, CCD dark current and detector non-uniformity. Ag-Behenate powder (The Gem Dugout, State College, Pa.) was used to calibrate the beam center and sample-to-detector distances. Two-dimensional scattering data were integrated by Data Squeeze 2.07 (Heiney et al. 2006) yielding a one-dimensional intensity profile as a function of scattering vector q.

Analysis of Reduced Scattering Data—The radius of gyration ($R_G$) was calculated using the indirect Fourier transform package GNOM (Svergun et al. 1992). The result is a pair-distance distribution function, p(r), in real space that represents an alternative means to calculate $R_G$ compared to traditional Guinier approximations that are produced from low angle q values in which q·$R_G$<1.3 (Guinier et al. 1955). In contrast, GNOM produces an $R_G$ calculated from the full experimental scattering curve and generates a maximum particle dimension ($D_{Max}$) as the distance where p(r) reaches zero, which is generally superior to the Guinier approximation (Glatter et al. 1977). The GNOM method relies upon perceptual criteria (Svergun et al. 1992) such that a solution for a compact, globular molecule obeys a smooth, monomodal Gaussian centered at $R_G$. Goodness-of-fit scores were 0.92 for hA3G-D (an "excellent" score) and 0.894 (a "good" score) for hA3G-DR. The MW for each sample was obtained from the respective pair-distance distribution functions by extrapolating to I(q=0) using GNOM (Svergun et al. 1992).

Ab Initio Structural Modeling—The low resolution molecular envelopes of hA3G-D and hA3G-DR were restored from their respective SAXS profiles using DAMMIN (Svergun, et al. 1999). In this method, simulated annealing is employed for global minimization, whereby random movements in a multiphase dummy atom model minimize the discrepancy $\chi$ between observed and calculated scattering curves. No symmetry constraints were applied to the hA3G-D restorations. Scattering curves with a q range between 0.021 to 0.17 Å$^{-1}$ and 0.016 to 0.18 Å$^{-1}$ were used for hA3G-D and hA3G-DR, respectively, corresponding to a resolution range between 300 and 35 Å ($2\pi/q_{max}$). A sphere was chosen as the initial starting model for each molecule, with $D_{Max}$ derived from the corresponding p(r). For hA3G-D, a dummy atom packing radius of 8.6 Å was assigned by the program; this radius was 3.75 Å for hA3G-DR. All calculations were run in 'slow' annealing mode. DAMMIN calculations were performed on a 64 node dual processor cluster at MacCHESS (Ithaca, N.Y.). Each restoration required ~20 h of CPU time on a 2.0 GHz 32-bit AMD processor. Ten independent DA models were calculated for hA3G-D and hA3G-DR. The 10 models of each class were subjected to automated envelope averaging using DAMAVER (Volkov et al. 2003). Here, each model was compared in a pairwise manner to other models of its class, resulting in a series of NSD values. The model with the lowest NSD was chosen as a reference onto which all other models were fit using SUPCOMB (Kozin et al. 2001). Neither ensemble included outliers based on the NSD criterion. As such, each group of ten models was included in the calculation of the average envelope. Each of the ten individual envelopes of a given class (hA3G-D or hA3G-DR) was mapped onto a densely packed grid of atoms with each position marked by its own occupancy value. Positions with significant, non-zero occupancies were chosen to produce a final model whose volume was equivalent to the average excluded volume derived from each independent model. It has been noted that final averaged structures from small angle scattering should not be considered a single unique macromolecular conformation in solution (Hammel et al. 2005, Johs et al 2006).

Shape Analysis—To determine whether multiple hA3G-DR envelopes could fit inside the hA3G-D particle, the hA3G-D envelope was moved to the origin and its principal axis of inertia oriented along the z-direction using ALPRAXIN. The hA3G-DR dimer was then subjected to a six-dimensional search of the oriented envelope using SUPMON (Kozin et al. 2001).

Relating Dimeric hA3G-DR to Cytidine Deaminase Crystal Structures—A single CDA domain of yeast CDD1 (PDB entry 1R5T) was subjected to a six-dimensional search against the hA3G-DR envelope using COLORES in the SITUS suite (Chacon et al. 2002, Wriggers et al. 2001). Several similar solutions were obtained that differed only by the rotational placement of the CDA monomer into the hA3G-DR envelope. With the first CDA subunit fixed, a second search was conducted to fit the remaining hA3G-DR envelope.

b) Supplemental Methods

DNA Deamination Assays—The in vitro activity of purified recombinant hA3G was measured using a 5'-$^{32}$P end-labeled single stranded DNA. Assay conditions were based on previous work in the field (Iwatani 2006, Chelico 2006). The substrate [5'-ATT ATT ATT ATT ATT CCC AAT TAT TTA TTT ATT TAT TTA TTT-3' SEQ ID NO: 1] and mock substrate (5'-ATT ATT ATT ATT ATT AGA AAT TAT TTA TTT ATT TAT TTA TTT-3', SEQ ID NO: 2) were generated by chemical synthesis (IDT, Iowa) and purified by denaturing PAGE. Specific activities for hA3G-D and h-A3G-DR were evaluated using 12.8 and 63.9 pM of NiNTA purified enzyme per reaction. Reactions were carried out in a deaminase buffer comprising: 40 mM TRIS pH 8.0, 40 mM KCl, 50 mM NaCl, 5 mM EDTA, 1 mM DTT, 2% (v/v) glycerol, and 0.1% (v/v) Triton X-100. The respective enzyme samples were mixed with 0.9-, 2.3-, 5.8-, 10-, 12-, 25-, 50- or 100-fold molar excess DNA substrate (or mock substrate) to a yield a final volume of 100 µl. The reactions were incubated at 37° C. for 30 min and stopped by addition of an equal volume of 2× Stop Buffer (0.10 M TRIS pH 7.5, 10 mM EDTA, 0.4% SDS, 0.2 µg/mL proteinase K and 0.2 µg/mL *E. coli* tRNA), which was allowed to digest for 20 min at 37° C. Each digestion was extracted with phenol:chloroform:isoamyl alcohol (50:49:1, v/v) and then re-extracted with chloroform:isoamyl alcohol (49:1 v/v) prior to ethanol precipitation with glycogen carrier. Each extracted time point was incubated with UDG (NEB, MA) in the manufacturer's buffer at 37° C. for 2 hours. The reactions were then treated with 0.15 M NaOH for 5 min at 37° C. and neutralized subsequently with 0.15 M HCl. The products were suspended in denaturing 90% formamide 1×TBE gel buffer, boiled for 1 min, cooled on ice and separated by 10% PAGE containing 8 M urea. Quantification of substrate and product bands was performed by phosphorimaging using ImageQuant software (Molecular Dynamics). Samples of hA3G-DR exhibited the highest specific activity with 100-fold excess substrate. The results suggested that a higher concentration of substrate would yield even greater activity.

Gel Filtration Chromatography—Pure hA3G-DR was applied to a Superose 6 10/300 GL column (GE Healthcare). The column was pre-calibrated with molecular weight standards in a range from 669 kDa to 13.7 kDa (GE Healthcare). A flow rate of 0.5 mL min$^{-1}$ was maintained with a System Gold Model 126 HPLC (Beckman Coulter). Elution was monitored at 280 nm by a Model 168 diode array spectrophotometer (Beckman Coulter). Samples were loaded in 250 µL volumes at 0.9 mg·mL$^{-1}$ and run at 4° C. The running buffer comprised 0.050 M HEPPS (pH 8.8), 0.070 M NaCl, 0.01 M MgCl$_2$, 0.2 mM DTT and 5% (v/v) glycerol.

Circular Dichroism Spectroscopy—To measure the RNA absorption of hA3G-D and hA3G-DR samples, CD spectra were acquired in the near UV between 250 to 300 nm (Tinoco, 2002) on a Model 202 CD Spectrometer (Aviv Inc.). To maintain concentrated protein, each sample was kept in 1×hA3G buffer containing 0.25 M imidazole. The UV spectroscopic 260:280 nm ratio was 1.65 for hA3G-D versus 1.0 for hA3G-DR. The absorbance reported here is in machine units. To demonstrate that hA3G-D and hA3G-DR of this study exhibit similar secondary structure contents in the presence and absence of RNA, far UV spectra for secondary structure calculations were recorded in a wavelength range from 190 to 250 nm. Ni-NTA purified samples were dialyzed first for 20 hours against 0.01 M Na$^+$/K$^+$ phosphate buffer at pH 8.5 containing 0.02 M Na$_2$SO4 and centrifuged at 14K×g for 10 min before use. Each scan was recorded at 20° C. with a 1 nm step size, a 4 nm bandwidth and a 10 sec averaging time; spectra were recorded in triplicate and background corrections were performed by subtracting the spectra of dialysis buffer. Machine units $\theta_{obs}$ (millidegrees) were converted to mean residue ellipticity $|\theta|$ (degree·cm$^2$·dmol$^{-1}$) by the following relationship:

$$|\theta| = (\theta_{obs} \cdot MRW)/(10 \cdot c \cdot l) \quad \text{(Eq. 1)}$$

where MRW is the mean residue molecular weight (protein MW/number of amino acids), l is the path length in cm and c is the concentration of the sample in mg·mL$^{-1}$. Samples were placed in a 400 µl quartz cuvette with a 0.1 cm path length. All spectral measurements were converted to delta epsilon for secondary structure analysis by the relationship:

$$De = |\theta|/3298 \qquad (Eq. 2)$$

Spectra were smoothed using a Savitsky-Golay function employing an 11 point window as implemented in Igor Pro 3.14 (Wavemetrics, Inc.). Spectra were analyzed using the CDPro suite (Sreerama 2000). The results reported are from CONTIN/LL using a basis set of 43 soluble proteins in the range of 190 to 240 nm. The CONTIN/LL program was selected because test studies showed it provided relatively superior results in the prediction of α,β and turn content for proteins in the far UV (Sreerama 2000). The method of von Hippel (Gill 1989) was employed to calculate an extinction coefficient, $\epsilon_{280}$ of 106.1 mM$^{-1}$·cm$^{-1}$, which was used for all hA3G protein concentration calculations. Additional CD experiments were conducted at 222 nm to evaluate the effects of urea on the hA3G sample. Chemical denaturation of hA3G at 20° did not begin until concentrations exceeded 2M.

Dynamic Light Scattering—Dynamic light scattering (DLS) measurements guided the purification procedures developed in this study with the goal of obtaining minimal HMM and LMM forms of hA3G in high quantity, purity and solubility. Scattering data were collected on a DynaPro 801 Molecular Sizing Instrument (Protein Solutions, Inc.). All measurements were recorded at 22° C. Pre-centrifuged samples were injected into a 12 µL cell and illuminated by a 25 mW laser at 750 nm. The hydrodynamic radius ($H_r$) and apparent MW of hA3G-D and hA3G-DR, respectively, were calculated using the Dynamics software package version 4.0 provided with the instrument (Protein Solutions Inc.). Calculation of the hydrodynamic MW was based on a standard curve generated for small globular proteins. The calculated $H_r$ range for the hA3G-D sample used in SAXS studies was 68.8-83.6 Å, corresponding to a MW range of 311-499 kDa. For hA3G-DR, the $H_r$=37.6-38.9 Å, corresponding to a MW range of 72-78 kDa. Errors in the $H_r$ measurements are distributed within ±10% of the mean of each sample.

c) Results and Discussion

Figure 1A:
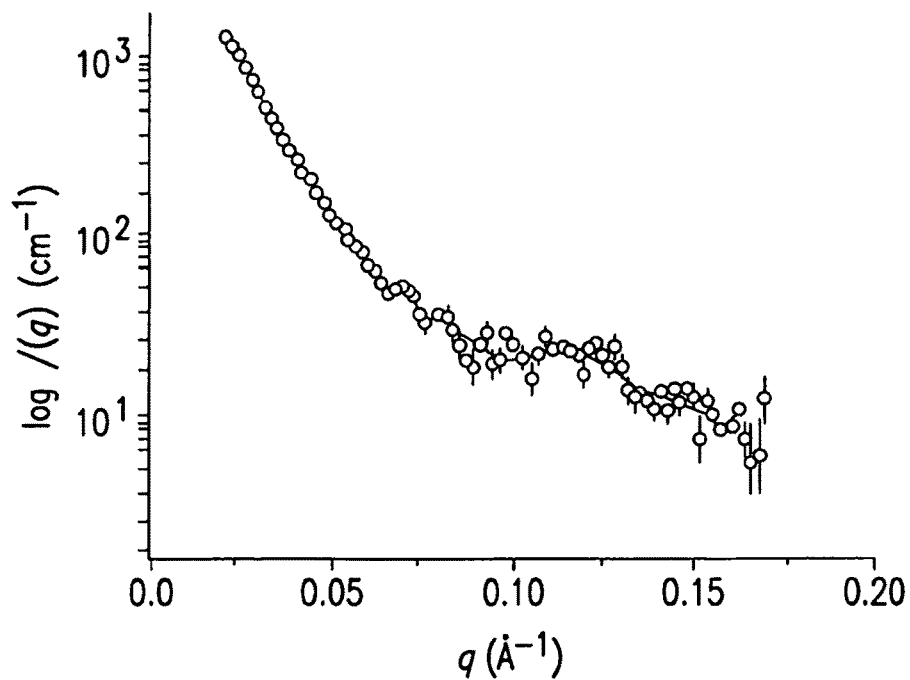
Figure 1B:
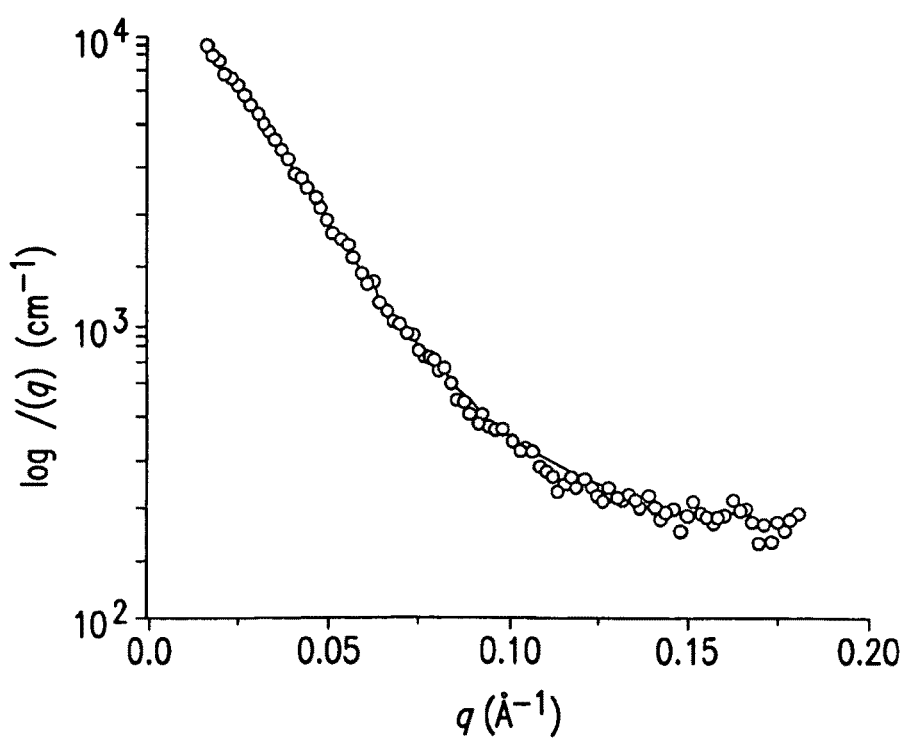
Figure 1C:
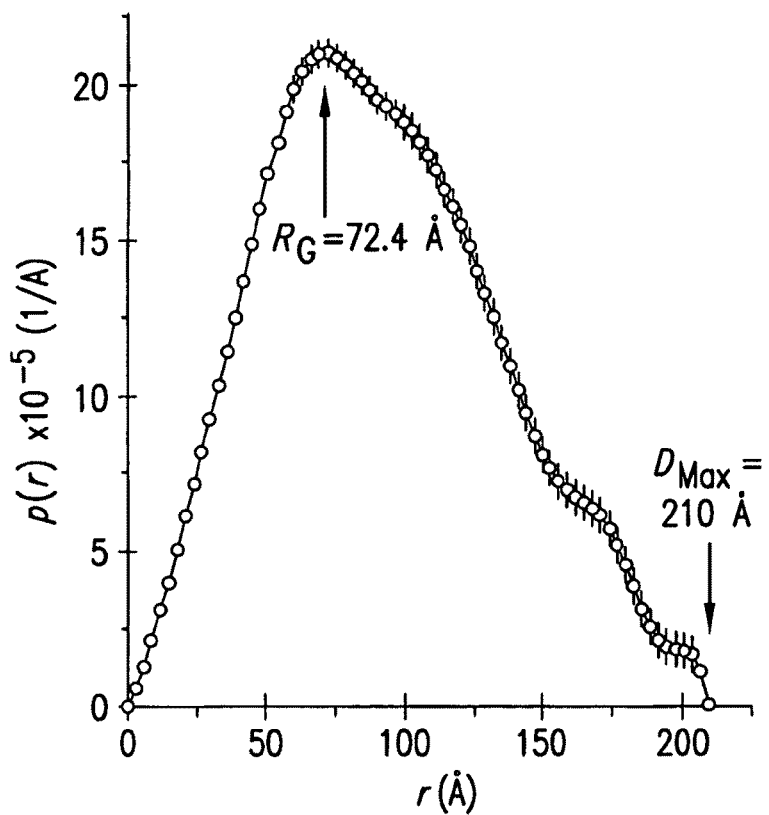
Figure 1D:
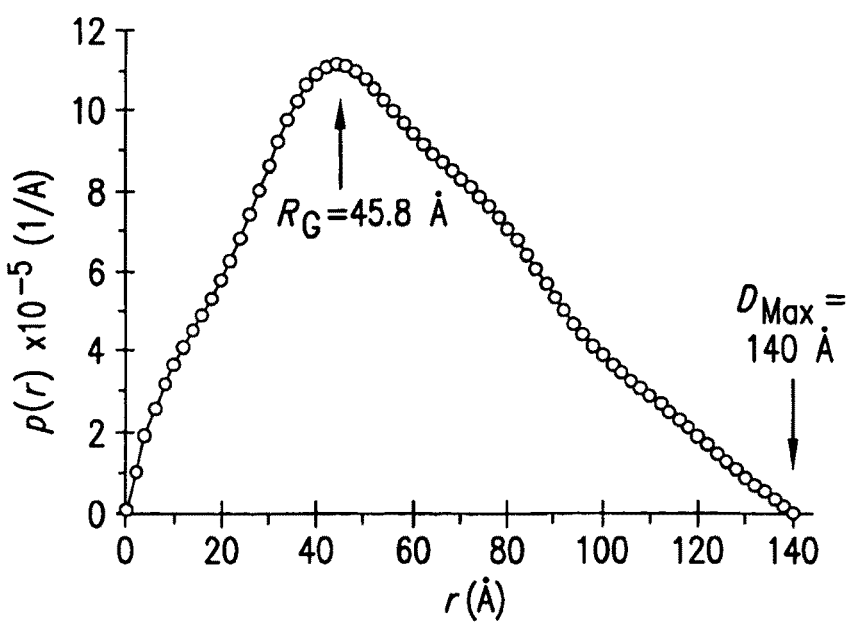

SAXS Data and Distance Distribution Functions—The experimental scattering profiles of pure recombinant hA3G-D (no RNase treatment) and hA3G-DR (RNase treated) are depicted in FIGS. 1A and 1B. Respective distance distribution functions (FIGS. 1C & 1D) were calculated by GNOM (Svergun et al. 1992). Both distance distributions are skewed from an ideal bell-shaped curve characteristic of elongated particles (Feigin et al. 1987, Petoukhov et al. 2006). The p(r) for hA3G-D indicates an $R_G$ of 72.4±0.9 Å and a maximum molecular dimension ($D_{Max}$) of 210 Å. The forward scattering I(0) was also calculated by the GNOM method and corresponds to a MW of 292±8 kDa. RNase treated hA3G-DR exhibits a smaller $R_G$ of 45.8±0.2 Å with a $D_{Max}$ of 140 Å; its I(0) corresponds to a MW of 100.6±4.5 kDa, consistent with a dimer of hA3G subunits. These MW values are in agreement with those obtained by DLS and/or gel filtration chromatography (FIG. 6).

Quality of Ab Initio Models. Bead models for hA3G-D and hA3G-DR were reconstructed from the experimental SAXS curves in DAMMIN (Svergun, et al. 1999). The agreement between an individual ab initio model and the experimental data is indicated by the fit of the model scattering curve with actual data (FIGS. 1A and 1B). Ten ab initio models each were calculated for hA3G-D and hA3G-DR. The final models exhibited λ values of ~1.2 for hA3G-D and ~2.8 for hA3G-DR. The observation that the hA3G-DR MW was consistent with a dimer prompted the use of a P2 symmetry constraint in model calculations; no significant difference in χ was observed using P1 symmetry. The average shape of each molecule was calculated by superposition of all 10 independent models. The average NSD value for hA3G-D models was 0.74 and that for P2 symmetric hA3G-DR was 1.144 (a value of 1.048 was obtained when no symmetry restraint was applied). An NSD value close to unity indicates good agreement between models, whereas ideally superimposed objects tend towards zero (Volkov et al. 2003, Kozin et al. 2001).

Figure 2A:
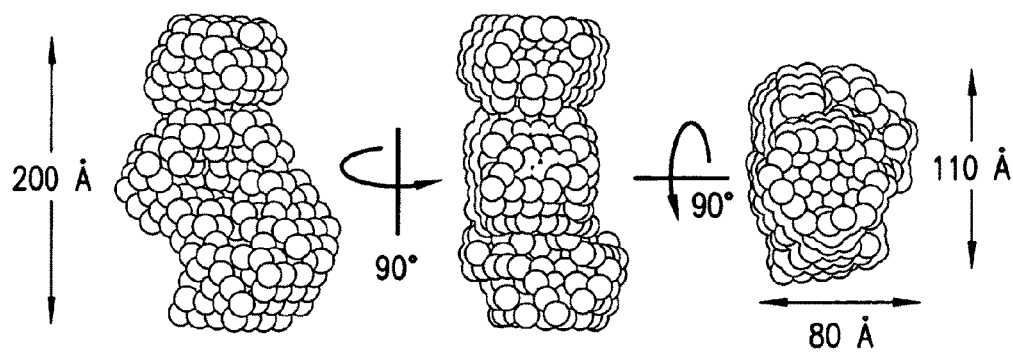
Figure 2B:
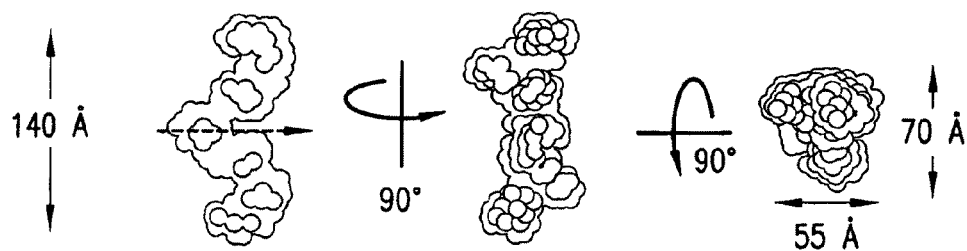
Figure 3A:
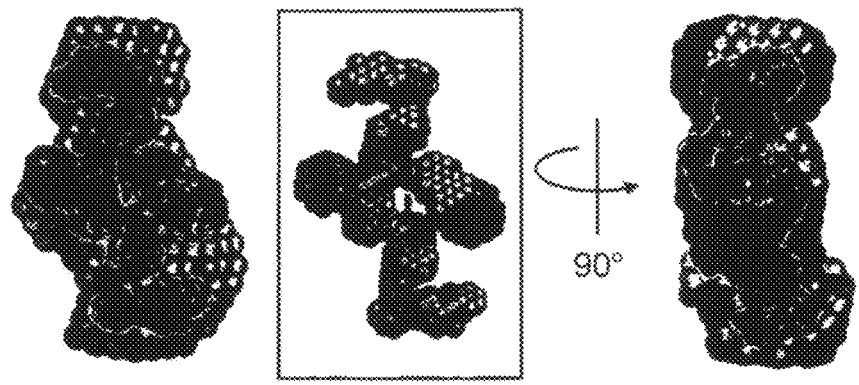

Descriptions of Average hA3G Models—The hA3G-D shape is an elongated cylinder (FIG. 2A). Three principal domains are apparent along the major axis of inertia with each being separated by a narrow cleft. The central domain possesses a depression in its broad face producing a toroid. The RNase sensitivity of this particle and its prominent CD absorption at 267 nm (FIG. 6) demonstrate that this structure represents a ribonucleoprotein complex. In contrast, the hA3G-DR structure is significantly smaller (FIG. 2B) consisting of an elongated multi-lobed organization comparable to 'beads-on-a-string'. The molecule possesses dyad symmetry with only a small buried surface area in the subunit interface, which is different from known CDA structures in which the dimer interface is extensive (Smith 2005).

hA3G-D is a Minimal HMM Particle that Accommodates two hA3G-DR Dimers—The highly purified hA3G-D can represent a minimal HMM particle. To analyze the size and shape relationship between hA3G-D and hA3G-DR, the latter's dimeric envelope was fitted inside that of the HMM particle using SUPMON (Kozin et al. 2001). The top solutions revealed that two independent hA3G-DR dimers (4 subunits) can be fit about a dyad-axis inside hA3G-D with no spatial overlap (FIG. 3A) giving an NSD of 1.1. A second mode of translational packing was also identified by manual inspection (FIG. 7). The rotational symmetry depicted in FIG. 3A is favored because it accounts for the depression in the central domain of hA3G-D (FIGS. 2A & 3A).

Figure 3B:
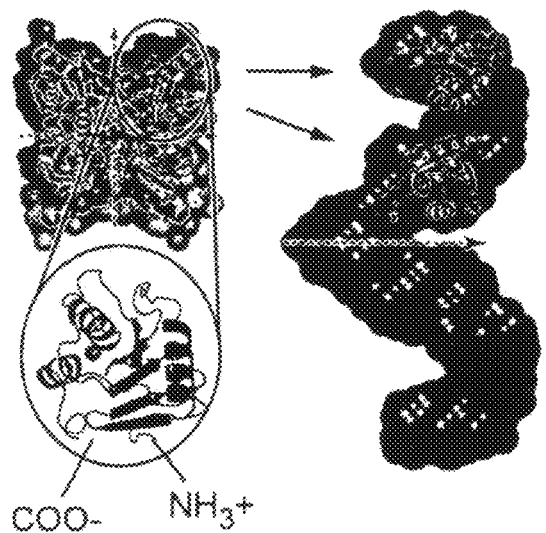
Figure 3C:
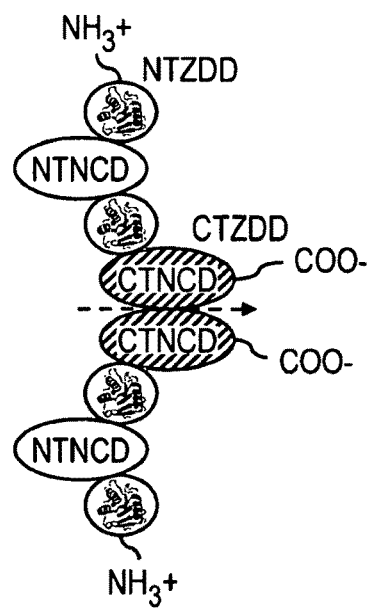
Figure 3D:
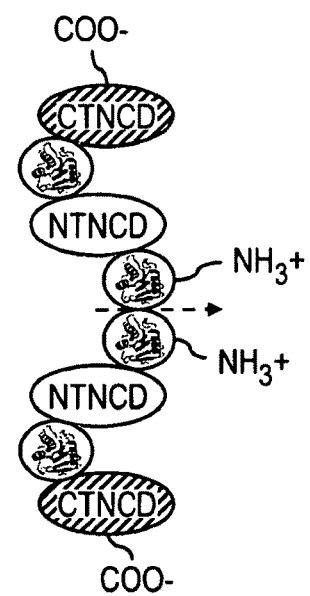

The Fold of the hA3G-DR Dimer is a Novel Structure by Comparison to Known Cytidine Deaminases—hA3G is a ZDD enzyme based on its catalytic activity and amino acid sequence alignment with known CDAs (Wedekind et al. 2003). However, its secondary structure content and fold classification have not been analyzed experimentally. Using CD spectroscopy, it was demonstrated that (i) hA3G-D and hA3G-DR belong to the α/β-fold fold class, consistent with the CDA family (Xie 2004), and (ii) the secondary structure content of hA3G-D does not change significantly upon RNase treatment (Table 3 and FIG. 5). These structural and functional similarities prompted a comparison of the hA3G-DR dimer to the fold of a representative CDA crystal structure, i.e. yeast CDD1 (Xie 2004). The CDD1 tetramer cannot superpose with upon either monomeric or dimeric hA3G-DR (FIG. 3B). CDD1 like other CDAs (such as the dimeric enzyme from *E. coli*) is much more compact than the elongated hA3G-DR structure. These observations show a tertiary and quaternary organization for hA3G.

Docking of a Minimal CDA Domain into the hA3G-DR Envelope Supports Tail-to-Tail Dimerization—The presence of deaminase activity, an α/β-fold and two ZDD signature motifs per polypeptide showed that the hA3G-DR envelope can accommodate at least two minimal CDA structures per subunit. An automated rigid body search of the hA3G-DR envelope was conducted using a single CDD1 subunit (FIG. 3B, oval inset) in the program SITUS (Chacon et al. 2002, Wriggers et al. 2001). A CDD1 monomer was chosen because it exhibits the minimal deaminase fold (~132 amino acids) and is structurally homologous to numerous other deaminases with the ZDD signature sequence (Xie et al. 2004). The results revealed that two ZDD motifs could be accommodated per hA3G-DR subunit with an average correlation coefficient of 0.76 per subunit. The top solutions differed only by rotational placement in the hA3G-DR envelope. For practical considerations, solutions were chosen (FIG. 3B) to orient the C-terminus of one CDA domain in close proximity to the N-terminus of another domain. The overall volumetric relationship within a single subunit follows a "large-small-large-small" pattern, which correlates with the domain organization of the hA3G sequence; i.e. an N-terminal ZDD motif, a smaller non-catalytic domain, a C-terminal ZDD motif and a short non-catalytic C-terminal domain (Wedekind et al. 2003). The results support a tail-to-tail dimerization model for hA3G (FIG. 3C), rather than a head-to-head (FIG. 3D) or head-to-tail configuration as proposed (Chelico et al. 2006). The extended tail-to-tail topology explains why each hA3G active site functioned as a monomer, devoid of dominant negative effects characteristic of trans subunit complementation (Opi et al. 2006). Tail-to-tail organization can also confer bidentate substrate affinity and deamination properties. As such, each solvent exposed N-terminal domain of a subunit can exhibit its established nucleic-acid binding properties, contributing to the affinity of substrates deaminated by a catalytically active C-terminal ZDD (Navarro et al. 2005). In this manner, transient binding and release of substrate by each half of a dimer would confer processivity, as well as the ability to 'jump' large distances past double-stranded substrate sequences (Chelico et al. 2006). Finally, the tail-to-tail dimer shows that hA3G possesses more than one mode of intersubunit interaction: (i) those promoted by protein, leading to self (or hetero) association (Jarmuz et al. 2002) and (ii) those promoted by RNA. The solvent accessibility and RNA avidity of the N-terminal ZDD combined with the ability of the C-terminus to form intermolecular subunit interactions imply that assembly of higher order ribonucleoprotein complexes is hierarchical. The close-packing of hA3G-DR dimers within a minimal HMM particle (i.e. hA3G-D) can attenuate substrate affinity and deamination through sequestration of N- and C-terminal ZDDs. Such a situation can arise if multiple hA3G-D particles were to coalesce, possibly through an RNA bridge. By analogy, sequestration of APOBEC-1 within inactive 60S editosomes was established as a mechanism to regulate mRNA editing, which requires reorganization into active, 27S complexes (Sowden et al. 2002).

TABLE 3

Protein Secondary Structure Calculations from CD spectra of hA3G-D and hA3G-DR

| Sample | α-helix | β-strand | Turn | Coil | NRMSD[a] |
|---|---|---|---|---|---|
| hA3G-D | 18% | 32% | 21% | 29% | 0.028 |
| hA3G-DR | 16% | 46% | 23% | 15% | 0.102 |

[a]The root mean square deviation between the experimental curve and the calculated spectrum.

Example 2

APOBEC3G Domains that Autonomously Dimerize and Bind to HIV-1 Vif and Gag

Human APOBEC3G (hA3G) is a cytidine deaminase that is a host defense factor against HIV-1. The HIV-1 protein, Vif, counteracts hA3G by preventing viral encapsidation and inducing hA3G degradation. Small angle X-ray scattering (SAXS) predicted that hA3G dimerization occurs via the C-terminus with a series of solvent exposed domains capable of autonomously interacting with other macromolecules. Structure-based methods were employed to identify domains that functioned autonomously in dimerization and interactions with HIV-1 Gag and Vif. The C-terminal catalytic domain (CD2, a.a 209-336) was necessary and sufficient for hA3G homodimerization. The N-terminal catalytic domain (CD1, a.a. 1-143) was sufficient for Vif binding and the N-terminal half (N1/2, a.a. 1-208) was required for viral encapsidation and Gag binding. Binding of discrete hA3G domains to Vif and Gag supports the hypothesis of an elongated structure for hA3G featuring independent functional domains. Conversely, the ability of hA3G to bind RNA and maintain anti-viral activity was intrinsic to only the full-length protein. This new understanding is important for therapeutic targeting to shield hA3G from Vif binding while not affecting viral encapsidation.

Human APOBEC3G (ApoB mRNA Editing Catalytic subunit-like 3G) or hA3G is a 384 amino acid member of the APOBEC family of cytidine deaminases that catalyzes the deamination of cytidine to uridine in the context of single stranded DNA (Jarmuz 2002; Wedekind 2003). hA3G is an anti-retroviral host defense factor that is a potent inhibitor of vif-deficient HIV-1 infectivity (Sheehy 2003). Vif(Viral infectivity factor) is an HIV-1 accessory protein and its N-terminus interacts with an N-terminal region of hA3G centered at aspartic acid 128 (Schrofelbauer, 2006; Mangeat 2004; Schrofelbauer 2004; Huthoff 2007). This interaction with Vif counteracts the host's innate anti-viral activity by inhibiting hA3G encapsidation into viral particles and promoting its degradation via the ubiquitin-dependent proteasomal degradation pathway (Mariani 2003; Mehle 2004; Stopak 2003; Yu 2003).

In the absence of Vif, hA3G can interact with RNA and the nucleocapsid (NC) portion of the HIV-1 Gag polyprotein during viral assembly enabling it to be packaged into the HIV-1 virus (Burnett 2007; Navarro 2005; Svarovskaia 2004; Khan 2005; Schafer 2004; Zennou 2004; Luo 2004; Cen 2004; Alce 2004). Virion packaged hA3G inhibits reverse transcription and hypermutates minus-strand HIV-1 DNA during reverse transcription to render the HIV-1 genome uninfectious (Bishop 2006; Guo 2006; Mangeat 2003; Harris 2003; Yu 2004; Zhang 2003). An N-terminal region of ~50-60 amino acids (a.a.) following the first zinc-dependent deaminase (ZDD) (Wedekind 2003; Xie 2004) motif within hA3G is necessary for hA3G incorporation into HIV-1 virus-like particles (VLPs) (Luo 2004; Cen 2004).

hA3G is actively retained in the cytoplasm (Bennett 2006) and its intrinsic ability to bind to a variety of RNAs, including endogenous retroviral RNAs (Kinomoto 2007; Chiu 2006), contributes to its localization in mRNA processing centers, stress granules and p-bodies (Kozak 2006; Wichroski 2006; Gallois-Montbrun 2007) as high molecular mass (HMM) complexes (Chiu 2006; Chiu 2005). It has been proposed that these characteristics prevent hA3G from acting on genomic DNA in the nucleus and protect cells from the threat posed by endogenous retroviruses (Kinomoto 2007; Chiu 2006).

Recently, small angle X-ray scattering (SAXS) and advanced shape restoration methods were used to analyze the global shape of hA3G as an active deaminase in solution. The resultant molecular envelope suggested that hA3G subunits associate through the C-terminus giving rise to a tail-to-tail dimer. The SAXS shape also supported an elongated morphology with substantial exposed surface area of the dimer, but limited intermolecular contact between the subunits (giving rise to the LMN model disclosed herein). The recently published crystal structure of APOBEC-2 revealed that it too has a unique elongated structure in the crystal lattice (Prochnow 2007). Collectively, these observations lend support to the concept that APOBEC family members possess an elongated shape that contrasts markedly with the zinc dependent cytidine/cytosine deaminases of pyrimidine metabolism whose structures are globular and compact with significant buried surface area at the oligomeric subunit interface (Prochnow 2007; Newman 2005). The structural hypotheses posited by the hA3G SAXS model as been tested, and has been evaluated in the context of dimerization, binding to Gag, Vif and RNA, as well as anti-viral activity.

Results

Rationale and Expression of hA3G Domains

Figures 8A, 8B, 8C:
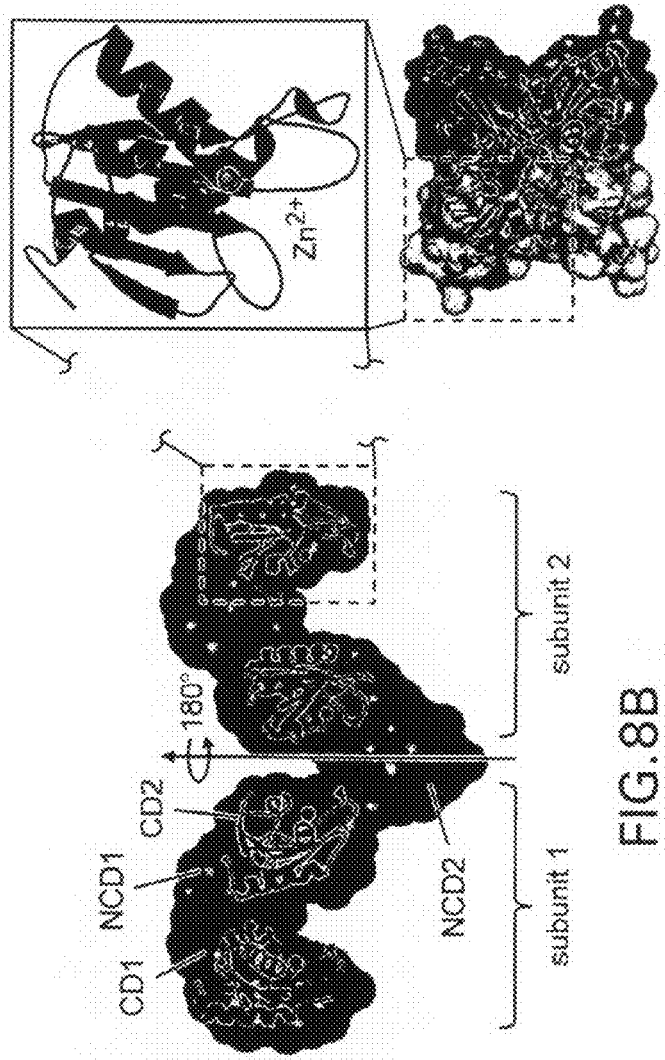

The nanoscale structure of catalytically active hA3G in solution suggested that the protein was a dimer comprising four discrete large volumes arranged in a linear manner (FIGS. 8a and b). Each large volume accommodated the equivalent of a single cytidine deaminase subunit, defined by the signature zinc dependent deaminase (ZDD) amino acid motif (Wedekind 2006) (FIG. 8a), which has been characterized structurally in the context of numerous pyrimidine metabolism enzymes, such as the yeast enzyme Cdd1 (Xie 2005) (FIG. 8c). Armed with this knowledge, probable domain boundaries were designed for the hA3G polypeptide with an initial emphasis on the ZDD catalytic regions. Catalytic domain 1 (CD1) a.a. 1-143 and catalytic domain 2 (CD2) a.a. 209-336 were expressed. The subdomains adjacent to CD1 and CD2 that have no known signature sequence were also expressed to relate them to an existing crystal structure; these regions are referred to as non-catalytic domain 1 (NCD1, a.a. 144-208) and non-catalytic domain 2 (NCD2, a.a. 337-384) (FIGS. 8a and b). In addition, larger constructs containing two or more domains were expressed that incorporated CD1-NCD1 (N1/2, a.a. 1-208), CD2-NCD2 (C1/2, a.a. 209-384), and a larger C-terminal domain lacking only CD1 (C3/4, a.a. 144-384). All constructs were expressed with N-terminal tags of HA, V5, EGFP-HA, or EGFP-V5. EGFP added size to the smaller domains, which aided in their analysis by SDS-PAGE. Constructs with and without EGFP behaved similarly in downstream functional assays (FIG. 9).

The crystal structure of APOBEC-2 would have appeared to be a more appropriate model, but was not used for several reasons. First, APOBEC-2 contains only a single ZDD motif while hA3G contains two within a single polypeptide (FIG. 8a) and APOBEC-2 shares only 41.2% and 38.2% identity between N1/2 and C1/2 of hA3G, respectively. Second, the oligomerization of APOBEC-2 differs from hA3G.

Whereas APOBEC-2 contains a head-to-head dimeric interface and a tail-to-tail tetrameric interface and hA3G appears to exhibit only a single tail-to-tail interface (Wedekind 2006; Prochnow 2007). Moreover, although the shapes of APOBEC-2 and hA3G are each elongated, an analysis of their overall shape similarity revealed that they are significantly different (FIG. 15). Specifically, a comparison of the observed one-dimensional scattering profile of hA3G in solution to those calculated from crystallographic coordinates revealed that APOBEC-2 does not describe the shape of hA3G in solution as well as the model derived from the restored envelope. This point is emphasized by the λ value of each comparison, which indicates Cdd1 is the worst model for hA3G, APOBEC-2 is intermediate, but the dummy atom model derived from SAXS is most plausible (FIG. 15). Finally, there is no known functional endpoint for analyzing APOBEC-2 compared to hA3G, because APOBEC-2 is not an active deaminase and has no known function making it difficult to relate structure and function. Therefore, the hA3G SAXS nanostructure was used as a plausible means to define domain boundaries that could be tested in functional assays.

hA3G Dimerization Occurs Through the CD2 Domain

The SAXS analysis of RNA depleted hA3G predicted a homodimer of hA3G subunits with a molecular mass of 100.6±4.5 kDa (i.e. monomer is 46.4 kDa). Gel filtration chromatography also supported a dimeric organization with an elution time corresponding to 95.2 kDa. Most significantly, the SAXS molecular envelope revealed a dimeric mass/volume distribution featuring a large-small-large-small:small-large-small-large pattern that best accounted for tail-to-tail hA3G domain organization of the form CD1-NCD1-CD2-NCD2:NCD2-CD2-NCD1-CD1 (FIGS. 8a and b). To validate the predictions from the SAXS molecular envelope, alternatively tagged (HA and V5) forms of hA3G domains were expressed in HEK-293T (293T) cells. These cells do not express endogenous hA3G but have been used widely for analyzing hA3G mutants in single round virus infectivity assays.

Figure 9B:
Figure 9C:
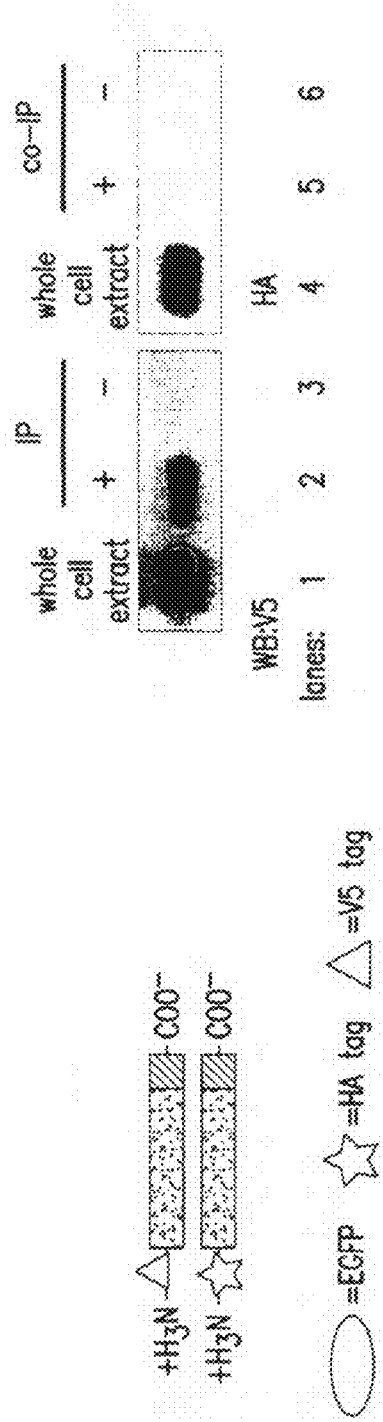
Figure 9D:
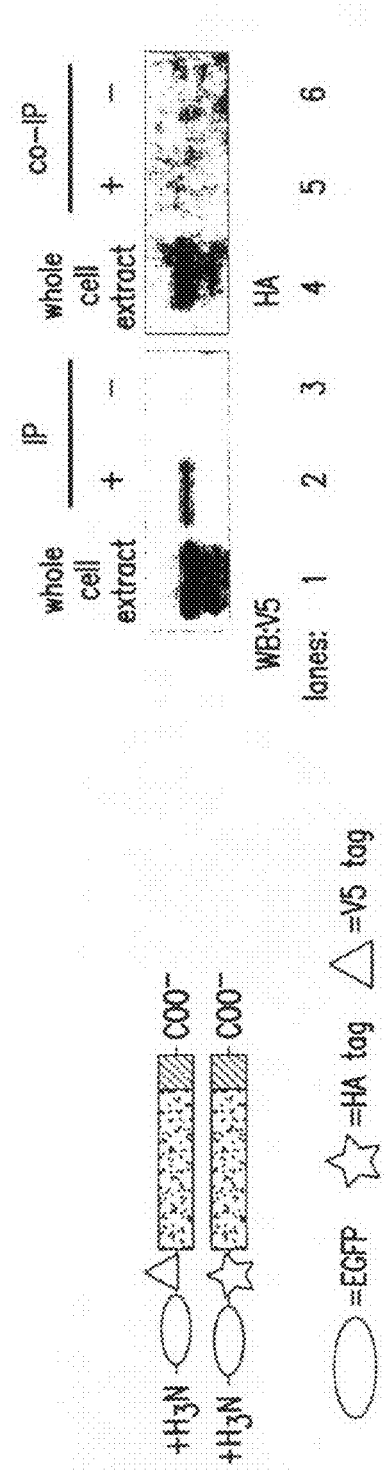
Figure 9E:
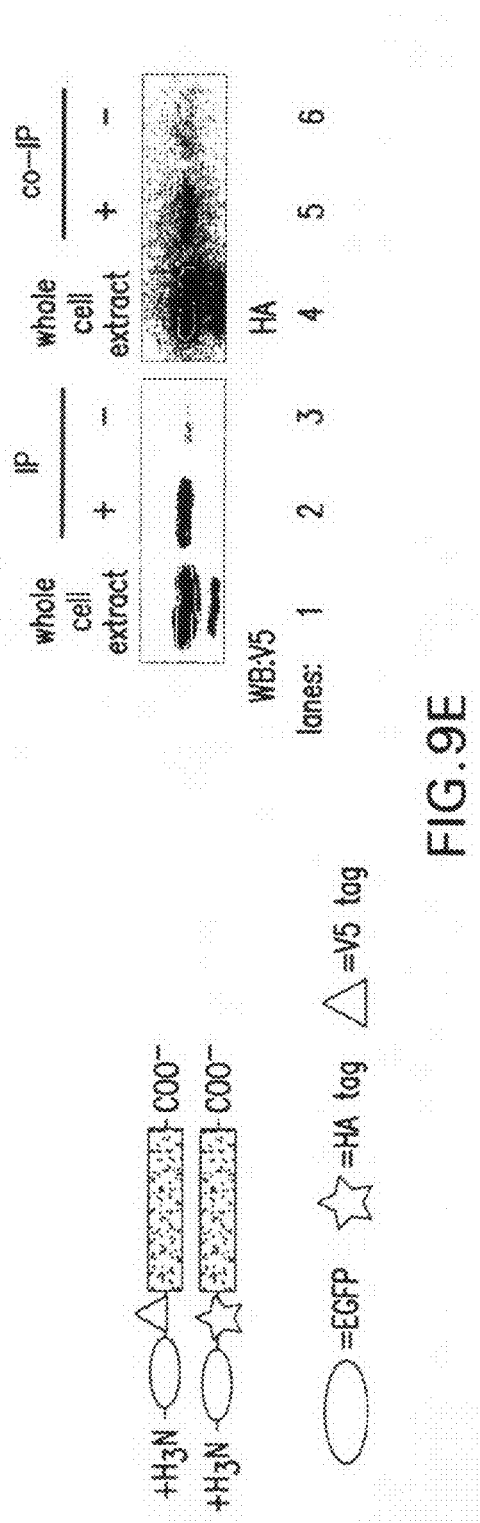
Figure 9F:
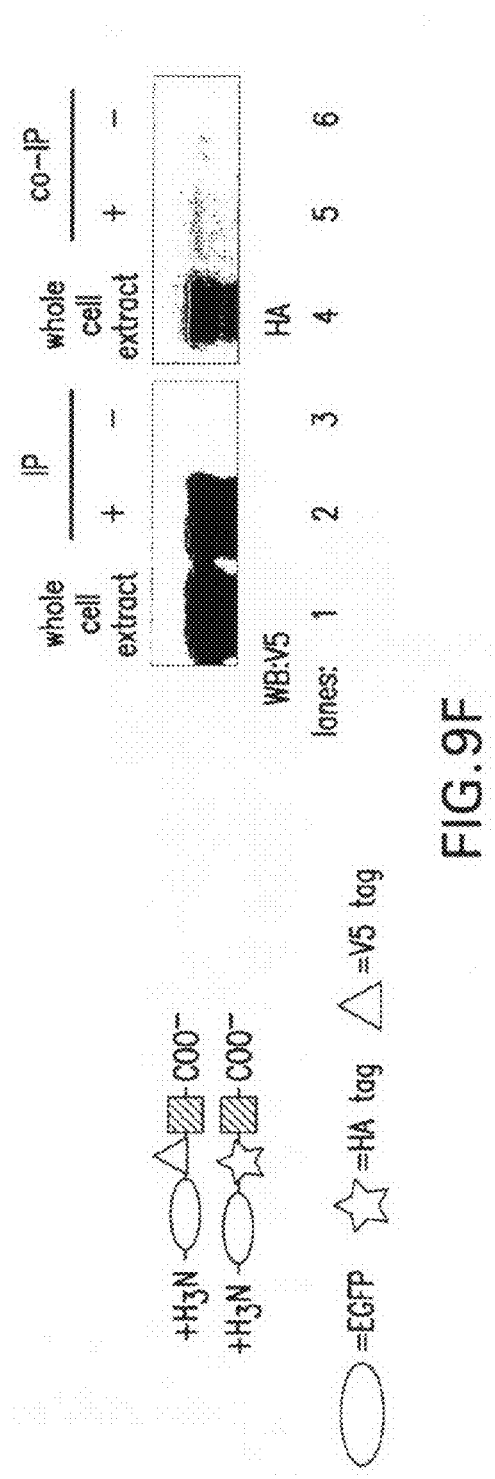
Figure 9G:
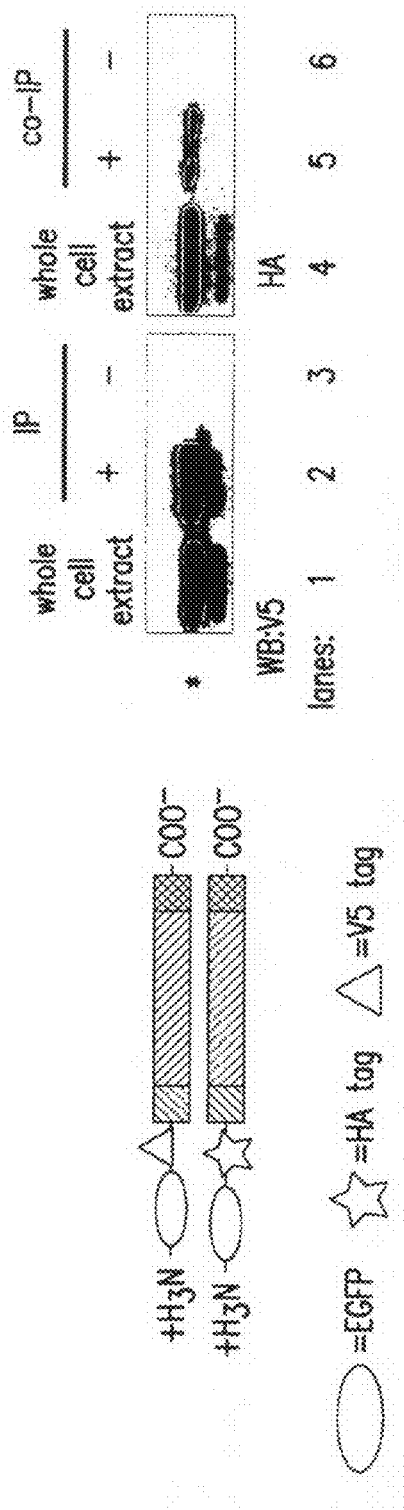
Figure 9H:
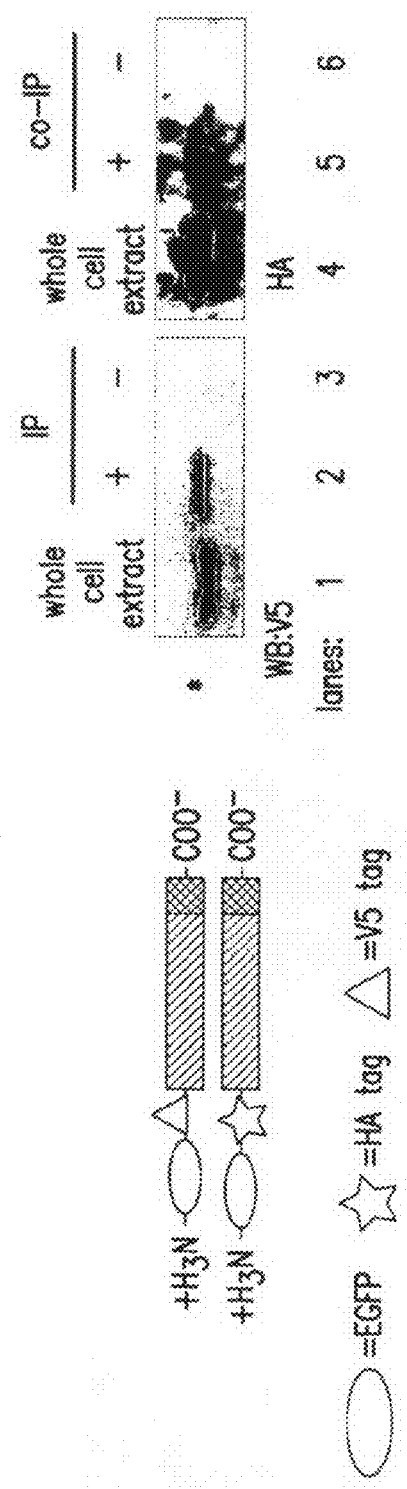
Figure 9I:
Figure 9J:
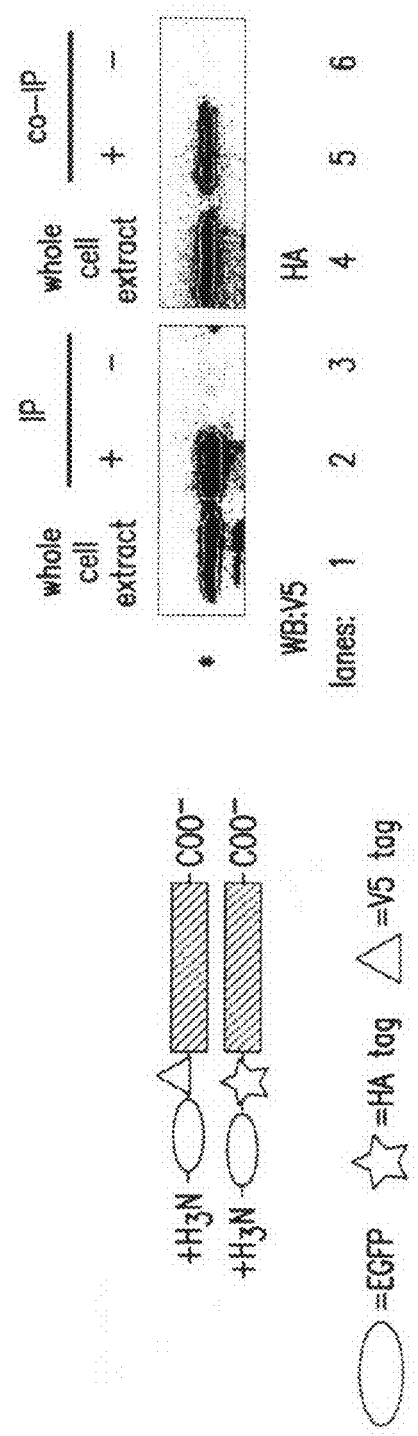
Figure 90:
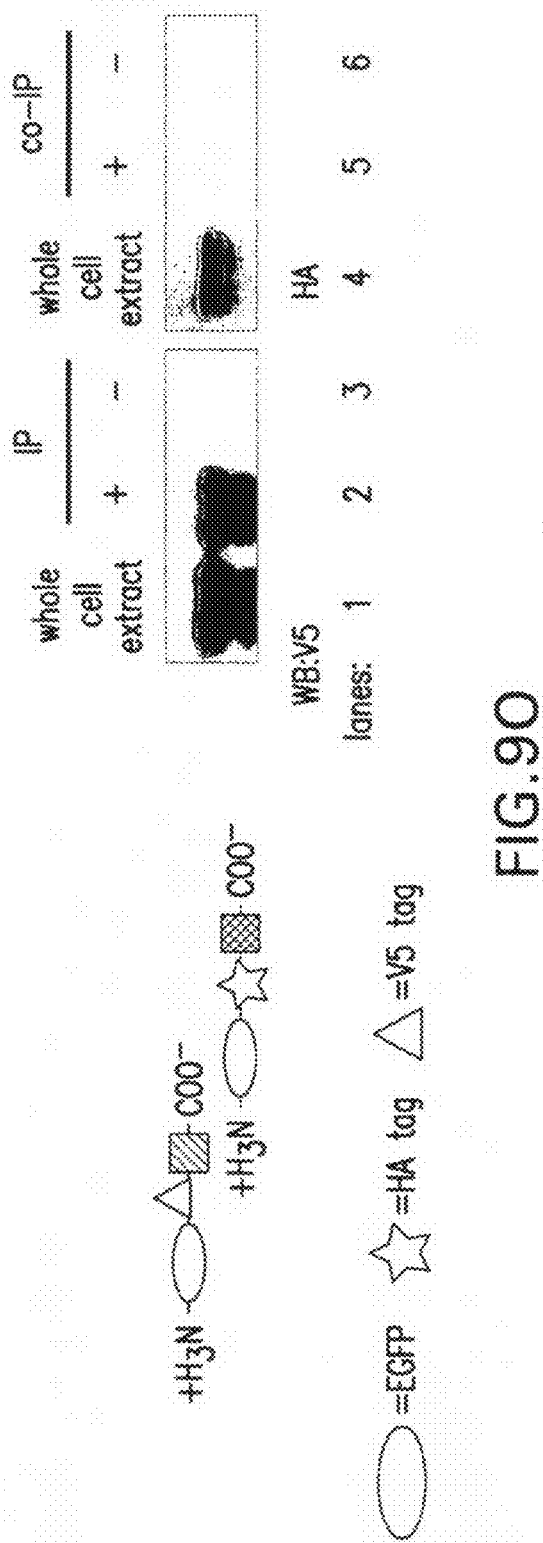

Twenty-four hours after transfection the cells were harvested and cell extracts were analyzed by co-immunoprecipitation (co-IP). Extracts were treated with RNase A prior to IP to eliminate interactions that were due to RNA bridging. All domains were expressed at equivalent levels (FIG. 9, lanes 1 and 4) and each could be immunoprecipitated (IPed) utilizing the V5 tag (FIG. 9, lane 2). Ts performed with Protein A beads alone indicated that none of the domains associated non-specifically with Protein A (FIG. 9, lanes 3 and 6). As an additional control for non-specific binding we showed that EGFP-V5-hA3G did not co-IP EGFP (FIG. 9a, lane 5), but that EGFP-V5-hA3G successfully co-IPed HA-hA3G (FIG. 9b, lane 5).

Co-IP analysis of hA3G domains revealed that C3/4, C1/2 (±EGFP) and CD2 alone all successfully co-IPed their alternatively tagged versions (FIG. 9g-j, lane 5). Domains that did not contain CD2 were unable to co-IP their alternatively tagged forms (FIG. 9c-f,k, lane 5). Combinations of N1/2 with C1/2, CD1 with CD2, and NCD1 with NCD2 were also unable to co-IP (FIG. 9l-o, lane 5). These data showed that CD2 was necessary and sufficient for hA3G dimerization, which corroborated the orientation of hA3G as a tail-to-tail dimer predicted by the SAXS envelope. The data also show that domains or subdomains expressed from other regions of hA3G are soluble as monomeric proteins.

Viral Encapsidation and Vif Interacting Determinants are within the N-terminal Half of hA3G Deletion mutagenesis has elucidated regions of hA3G predicted to be necessary for its packaging into VLPs (Luo 2004; Cen 2004). In the context of the hA3G structural predictions, the domain constructs of this study were evaluated for the ability to function autonomously in viral encapsidation, as well as the ability of Vif to influence their assembly into virions. To this end, pseudotyped wild-type (WT) and Δvif HIV-1 virions were produced in 293T cells co-transfected with hA3G domain constructs and evaluated for viral encapsidation. Western blotting for β-actin and p24 revealed equal loading of cell extracts and viral particles, respectively (FIG. 10). Vif westerns verified Vif expression by the WT viral DNA construct (FIG. 10). As a positive control, full-length hA3G was encapsidated into viral particles and its packaging was observed to be significantly reduced in WT virions showing that Vif had inhibited its packaging (FIG. 10, viral particle lanes 1-2).

N1/2 containing CD1-NCD1 was the minimal domain that was encapsidated and its packaging was inhibited by Vif (FIG. 10, viral particle lanes 3 and 4). Notably, CD1 (a.a. 1-143) alone was not encapsidated showing that the region encompassing NCD1 (a.a. 143-208) was required (FIG. 10, viral particle lanes 3-6). Moreover, NCD1 and C3/4 alone were not sufficient for encapsidation (FIG. 10, viral particle lanes 7-10). The data showed that multiple determinants within a larger domain comprised of CD1 and NCD1 were required for viral packaging.

N-terminal Domains Interact Directly with Gag and Vif

Figure 11A:
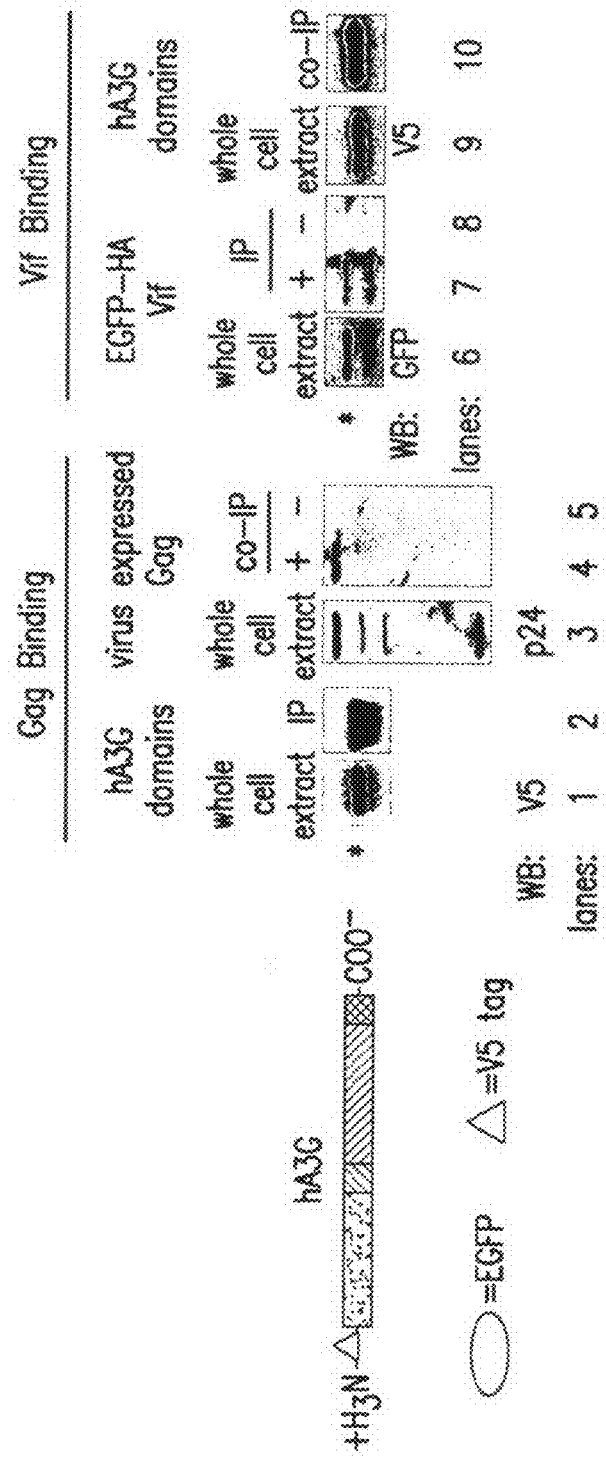
Figure 11B:
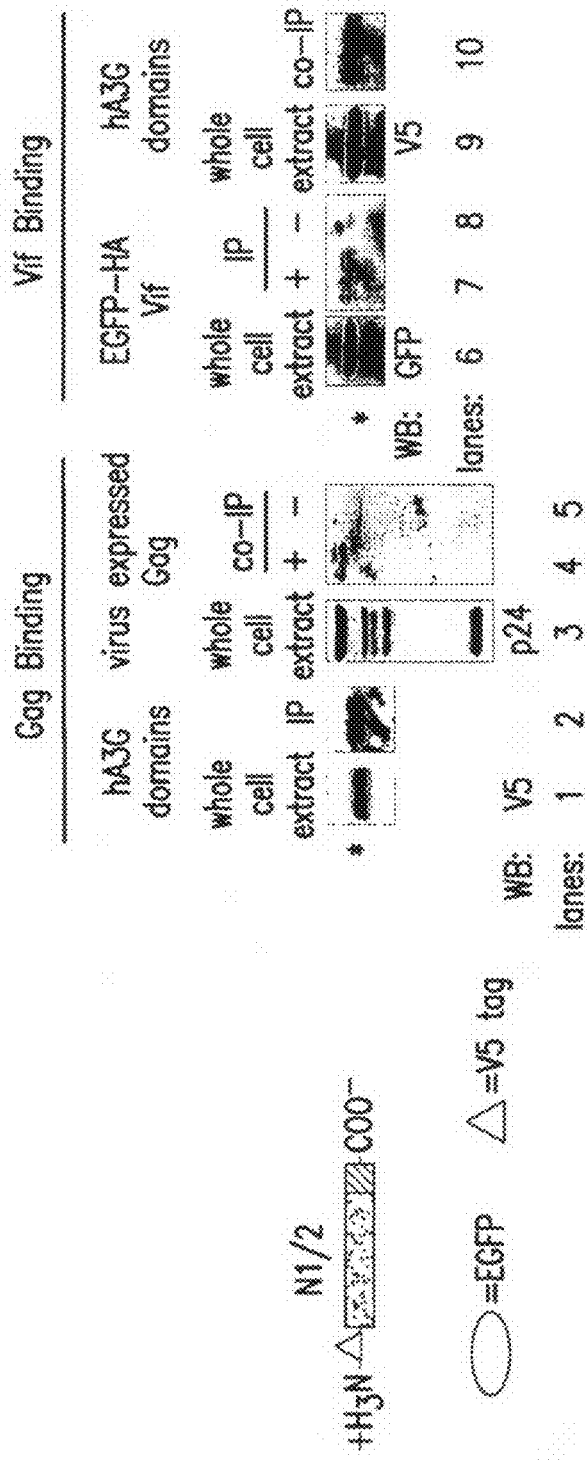
Figure 11C:
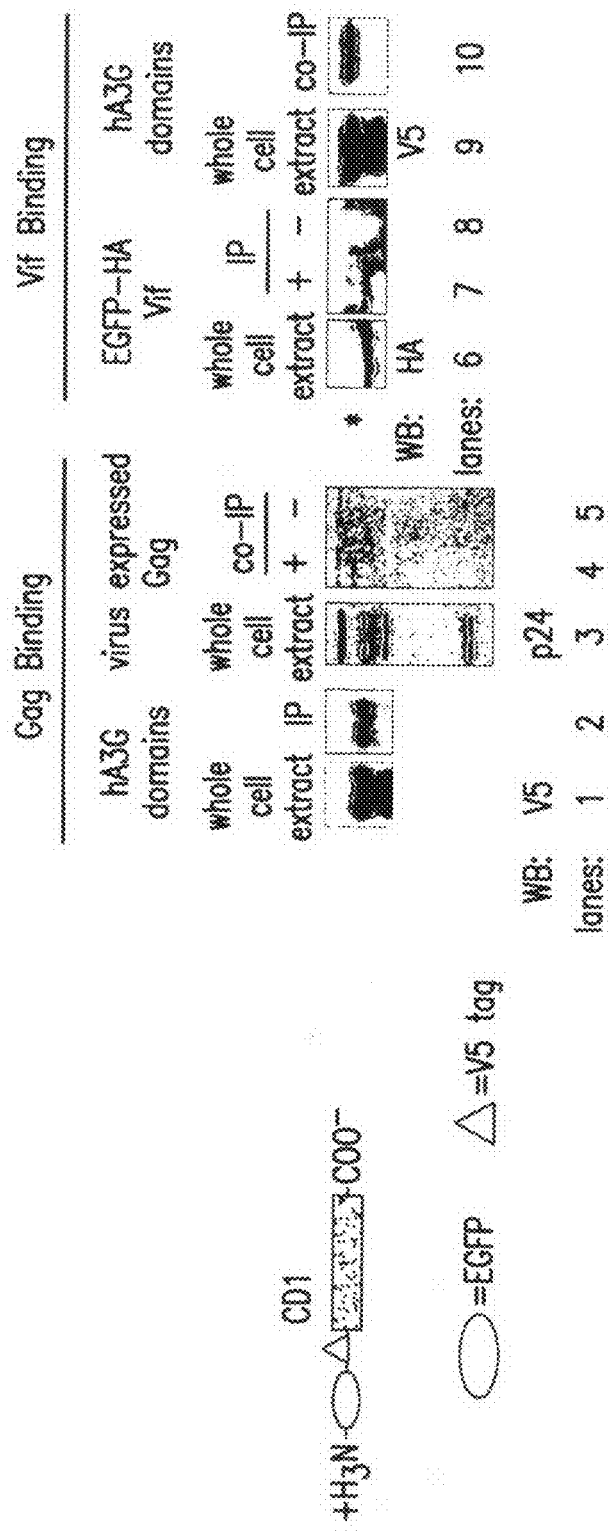
Figure 11D:
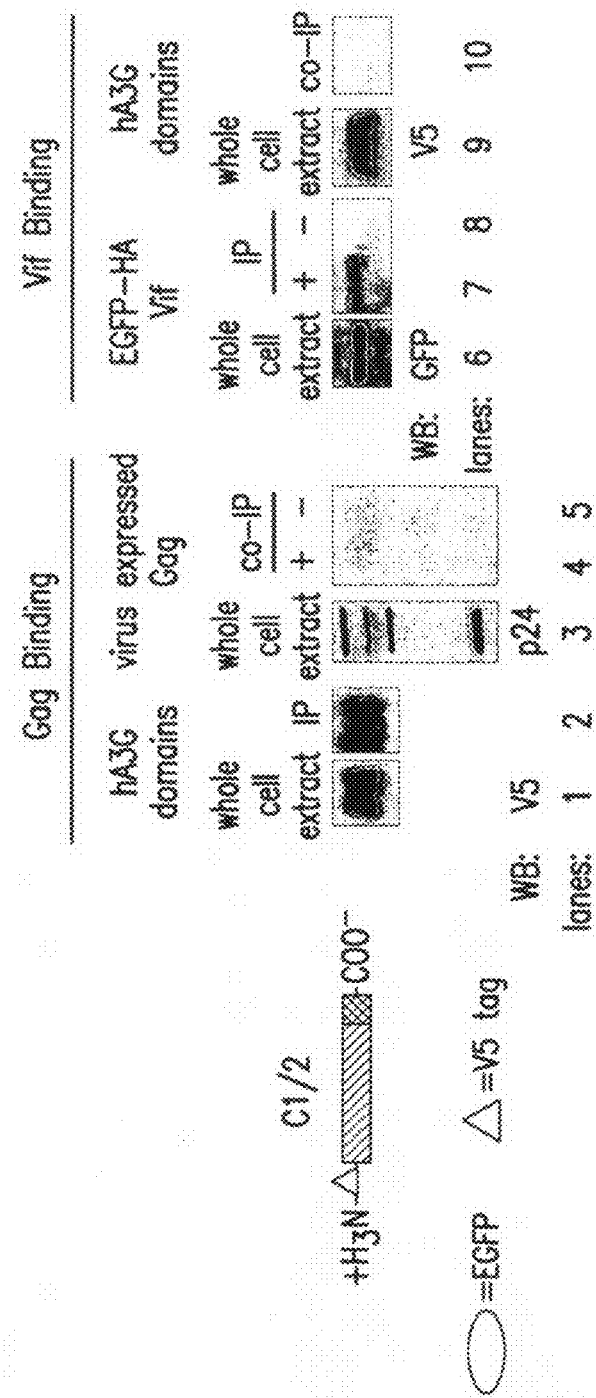
Figure 11E:
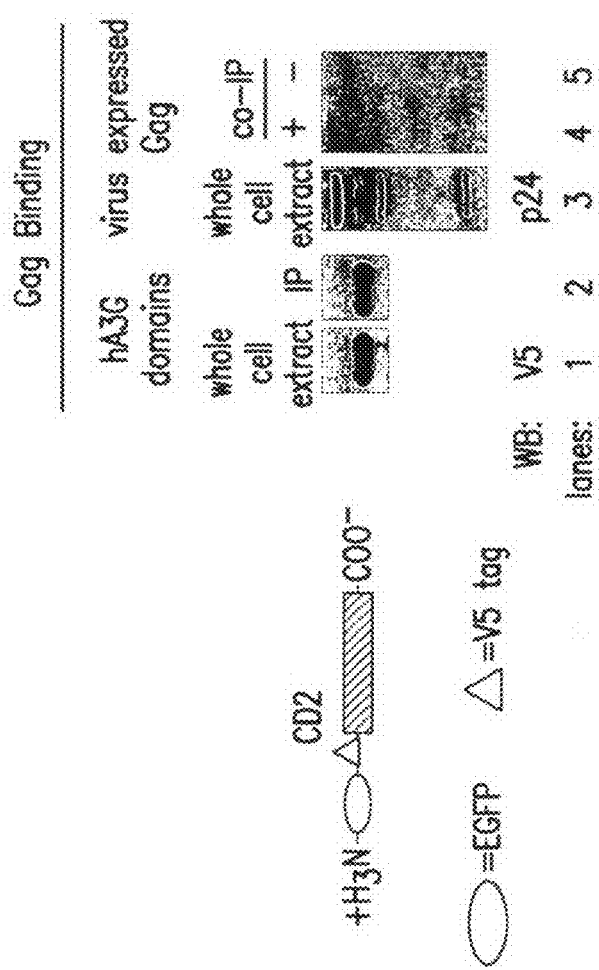

To further explore the concept that hA3G exhibits a 'modular' domain organization, experiments were conducted to elucidate the contribution of various regions to viral encapsidation. Co-IP experiments were performed using various hA3G domains and Gag or Vif following RNase A digestion of cell extracts. Control IP as described above demonstrated that Gag and Vif were not non-specifically associated with Protein A (FIG. 11, lanes 5 and 8). Gag polyprotein co-Ted with full-length hA3G and N1/2 in support of the viral encapsidation results (FIG. 11a-b, lane 4). CD1, C1/2, and CD2 did not co-IP Gag (FIG. 11c-e, lane 4) consistent with all three being unable to be packaged into the virus.

Interestingly, the whole cell extract lanes showed multiple cleavage products normally observed when western blotting for p24 (24 kDa capsid domain of Gag) (FIG. 11, lane 3). Only the p55 Gag polyprotein (55 kDa) co-IPed with N1/2 (FIG. 11a-b, lane 4), confirming that hA3G interacted specifically with the NC domain of Gag (p24 detected bands below p55 lack NC) and underscoring that only biologically relevant interactions were observed in the coIPs. Both hA3G and N1/2 had significantly lower abundance in WT viral particles compared to ΔVif suggesting that Vif was inhibiting encapsidation (FIG. 10, lanes 1-4). Consistent with this, both hA3G and N1/2 were co-IPed with Vif (FIG. 4a-b lane 10).

CD1 alone was not packaged in WT or Δvif virions (FIG. 10, viral particle lanes 5 and 6), but CD1 was co-IPed with Vif (FIG. 10c, lanes 6-10). In contrast, the C1/2 domain did not co-IP with Vif (FIG. 10d, lanes 6-10) consistent with the known requirement for the region surrounding aspartic acid 128 (contained in CD1) for Vif binding. Taken together with the previous findings, these data showed that although CD1 did not contain sufficient structural information to impart a Gag interaction, it contains determinants sufficient for a specific Vif interaction.

In the course of this investigation it was noted that the abundance of hA3G and Vif interacting domains was not significantly reduced by Vif expressed from WT virus (FIG. 10, cell extracts lanes 1-6). Others have observed reduced virion incorporation of hA3G by Vif in the absence of degradation (Opi 2007) and Vif-dependent degradation of hA3G is affected by the ratio of Vif to hA3G, which must be at least 4:1 (based on plasmid DNA input) for significant amounts of hA3G degradation by Vif (Wichroski 2005). In these experiments the ratio was only 2:1 for plasmids expressing viral DNA and hA3G domains.

ha3G Protects RNAs of Specific Sizes from Nuclease Digestion

The ability of N1/2 to co-IP Gag following exhaustive RNase A digestion of extracts (FIG. 4b, lanes 1-5) suggested that RNA was not required for packaging. However, point mutagenesis of hA3G and gel shift analyses demonstrated that residues within the N-terminal ZDD alone (CD1) contributed to RNA binding. The N-termini were predicted to be surface exposed in the SAXS envelope of dimeric hA3G showing that they can be relatively accessible for RNA binding. Moreover, the SAXS shape restoration of purified hA3G bound to RNA predicted that at least two hA3G dimers (i.e. a dimer of dimers) can be accommodated within the molecular envelope of an HMM-like complex with sufficient volume for an additional ~300 nucleotides (nt) of RNA. If this model is correct, at least one N-terminal domain of each hA3G dimer can be solvent exposed in these larger complexes showing a possible mode of hA3G coalescence into RNA-bridged particles of MDa complexity.

Given that the RNA binding activity of hA3G is not sequence specific but is integral to the formation of higher order oligomeric forms of hA3G, the physical interaction of hA3G with RNA was evaluated by RNase protection assays. In this method unbound and surface exposed RNAs were digested to nucleotides whereas RNA protected by its interaction with protein was recoverable as discrete RNA fragments. RNA co-purified with hA3G in the absence of exogenous RNase was visualized by denaturing PAGE and silver staining and exhibited a size distribution ranging from 0.4 to 0.75 kb (FIG. 12a, lane 2). RT-PCR revealed that this RNA contained rRNA (18S and 28S) and hA3G mRNA expressed through Baculovirus infection of Sf9 cells (FIG. 16). Furthermore, hA3G UV crosslinked with equivalent efficiency to the first 520 nt of radiolabeled HIV-1 RNA and a 448 nt region of apoB RNA (7.4% identity) (FIG. 17). Taken together these data demonstrated that purified hA3G has an intrinsic, but non-specific RNA binding activity.

Figure 12C:
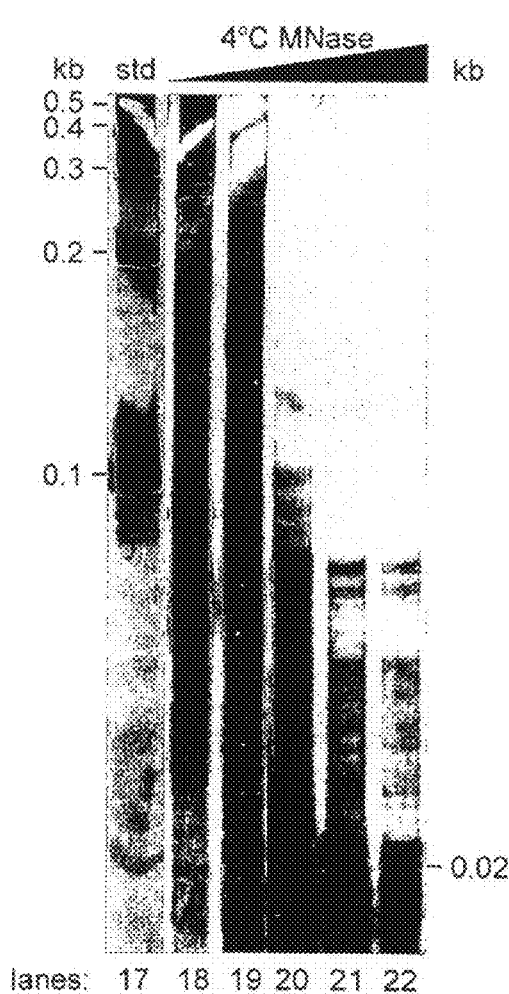

Upon nuclease digestion of hA3G-RNA complexes at 37° C. with increasing amounts of Micrococal Nuclease (MNase) or RNase A, protected fragments of RNA became apparent initially at 90 nt (predominating at lower MNase and RNase A concentrations) followed by a 70 nt band (predominating at higher nuclease concentrations) (FIG. 12a, lanes 3-12). MNase digestion at 4° C. revealed another 20 nt band (FIG. 12c, lanes 20-22). Recovery of these RNA fragments was dependent on hA3G protection and was not due to a nuclease-resistant RNA secondary structure as nuclease digestion of naked cellular RNA did not yield protected RNA fragments (FIG. 12b, lanes 15 and 16).

Figure 12D:
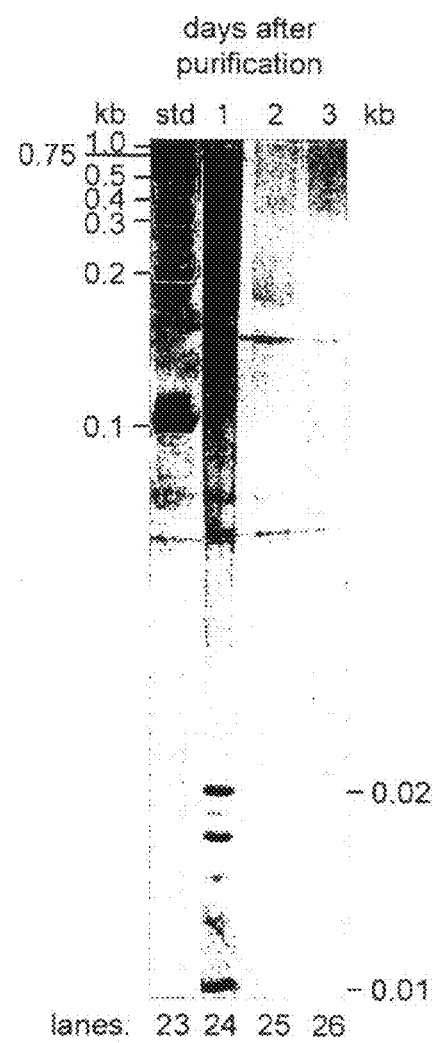
Figure 13A:
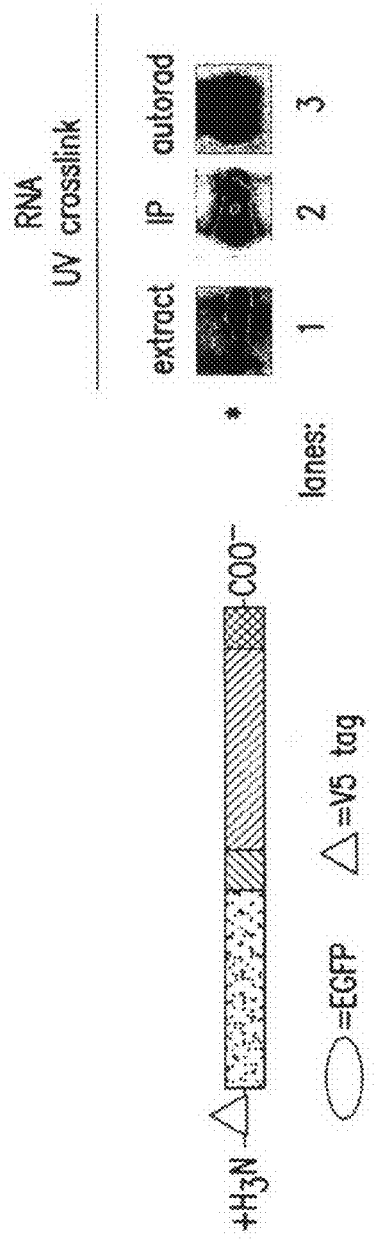
Figure 13B:
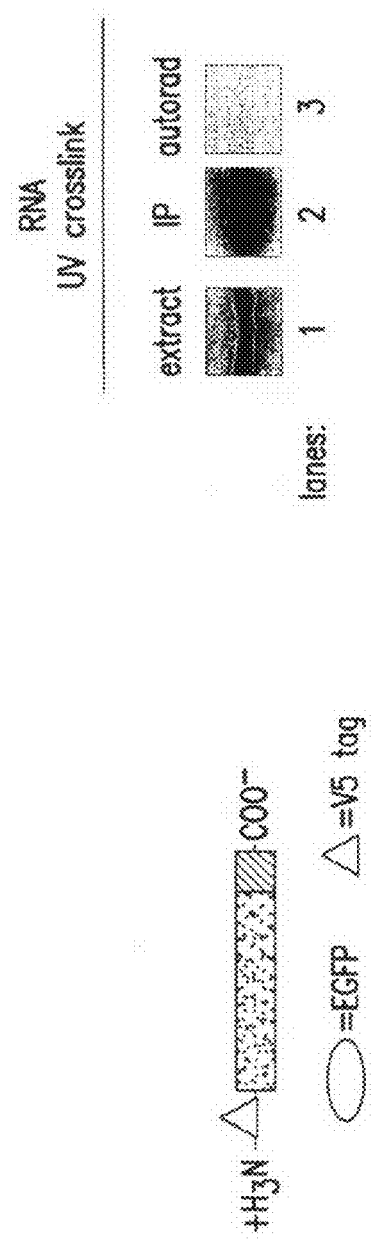
Figure 13C:
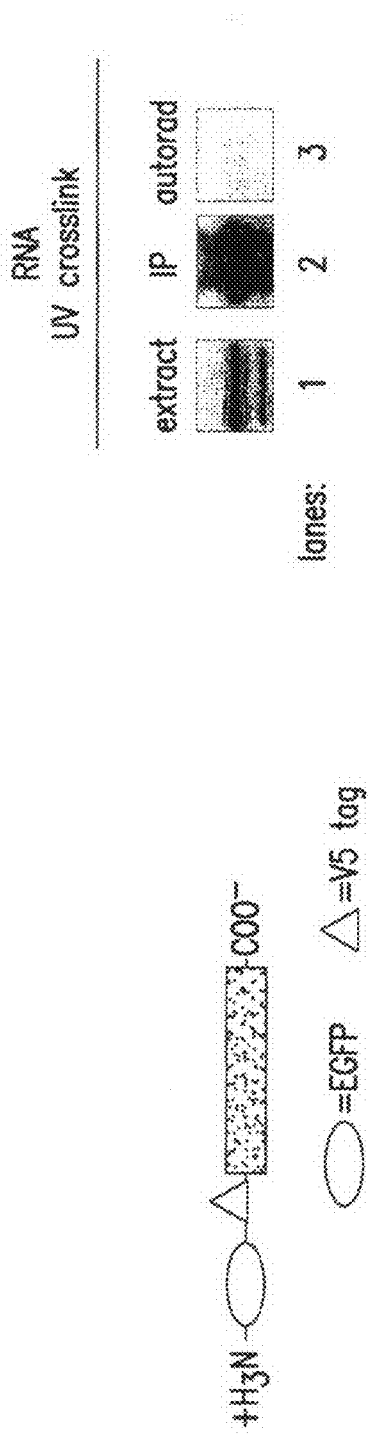
Figure 13D:
Figure 13E:
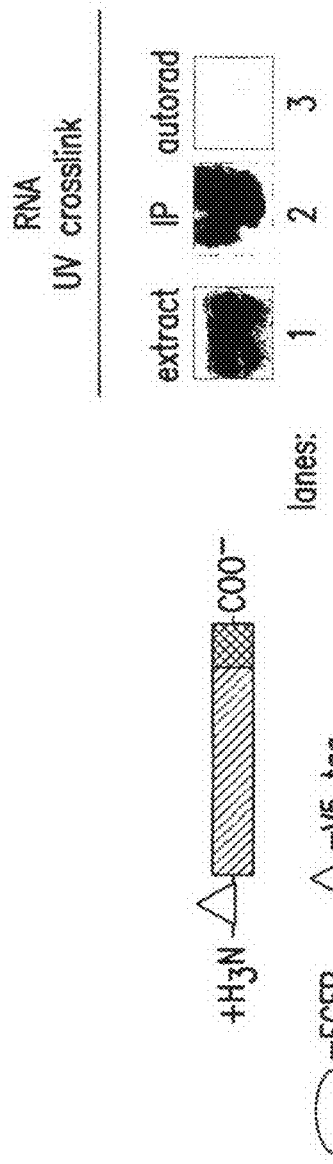
Figure 13F:
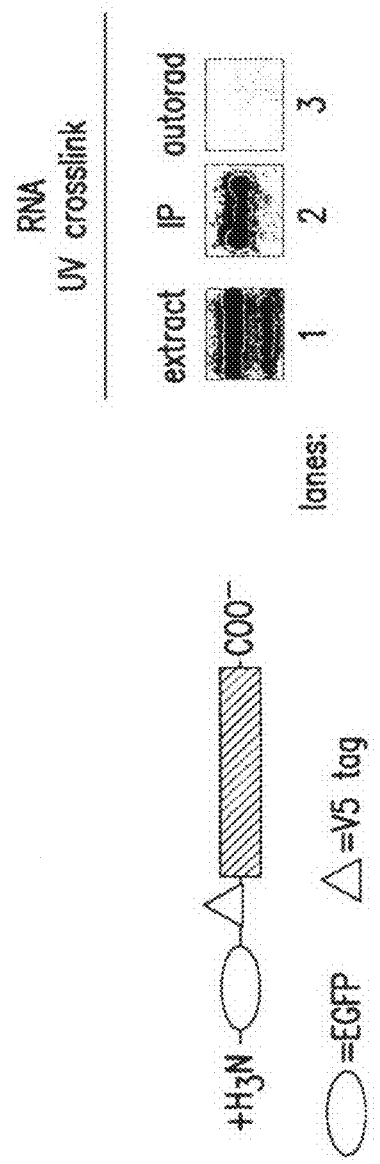

Exhaustive digestion of hA3G with RNase A during purification to produce catalytically active protein retained protected RNAs of only 10-20 nt (FIG. 12d, lane 24). The protection of RNA fragments of discrete size that became progressively smaller with increased nuclease concentration shows that specific protein-RNA contacts exist that may serve to recruit hA3G dimers into higher order ribonucleoprotein complexes. The oligomerization of such dimers through RNA bridging can result in the protection of significantly large segments of RNA such as those observed here. The participation of this extended hA3G surface area may sterically hinder hA3G from binding single stranded DNA substrates and thereby account for the RNA-dependent inhibition of deaminase activity previously observed (Chiu 2005; Wedekind 2006; Chelico 2006; Soros 2007). Such RNA-dependent inhibition has been reported for a related family member, AID, whose DNA deaminase activity can only be capitulated by treatment with RNase (Bransteitter 2003).

RNA Binding Requires Full-length hA3G

The protection of large RNA fragments by hA3G suggests that an extensive protein surface may be required for RNA binding, which is consistent with a non-specific interaction motif rather than a novel module. However, protection of small RNA fragments may be due to the RNA binding capacity of a specific domain. To determine if autonomous domains of hA3G are involved in RNA binding, radiolabeled RNA was UV crosslinked to the respective hA3G domains in cell extracts followed by IP analysis. Surprisingly, it was found that although full-length hA3G efficiently bound RNA in vitro (FIG. 13a), N1/2 and other monomeric domains and subdomains of hA3G did not associate with RNA (FIG. 13b-

*d*). Moreover, the N1/2 domain of hA3G that bound to Gag (i.e. as Gag-N1/2 IPed complexes derived from HIV-1 transfected cell extracts) also did not bind RNA (FIG. 18). These results showed that RNA binding may not be required for hA3G encapsidation and that protein-protein interactions between Gag and hA3G are sufficient for viral encapsidation. It is likely that full-length hA3G is required for RNA binding because only dimers of hA3G present sites capable of coordinating a stable interaction with RNA via CD1 domains (since dimeric domains containing CD2 but lacking CD1 did not bind RNA (FIG. 13*e-f*)). This model is consistent with an extensive surface area requirement for binding large RNase protected fragments and accounts for the HMM forms of hA3G seen both in endogenously expressed hA3G in cells as well as purified hA3G in the presence of RNA (Chelico 2006).

Anti-viral Activity Requires Full-length hA3G

Soros et al. has shown that newly synthesized hA3G was encapsidated in viral particles prior to its interaction with cellular RNA and formation of HMM complexes (Soros 2007). Newly synthesized hA3G bound to viral RNA genomes to form deaminase inactive HMM-like complexes within the core of HIV-1 viral particles. Upon entry of this virus into host cells, hA3G deaminase activity within the C-terminal domain, CD2, was restored by the RNase H functionality of HIV reverse transcriptase. This work suggested that the anti-viral activity of hA3G related closely to the intimate association of hA3G with HIV RNA in the viral capsid.

In light of this mechanistic scenario, neither the C1/2 nor N1/2 of hA3G alone should have anti-viral activity, because they both lack RNA binding activity. Given that N1/2 was encapsidated, it was tested for its ability to function autonomously as an anti-viral protein in single round infectivity assays using pseudotyped Δvif HIV-1 produced in 293T cells. Viral particles were isolated from 293T cells expressing Δvif HIV-1 and VSV-G co-transfected with hA3G, N1/2 or vector alone (no hA3G), and their infectivity was analyzed in TZM-bl cells that express luciferase from an HIV LTR promoter (Platt 1998). Consistent with the literature, viral particles collected from cells expressing full-length hA3G had 100-fold less infectivity than those collected from cells that did not express hA3G (FIG. 14). In contrast, the infectivity of viral particles collected from cells expressing N1/2 had nearly wild type levels of infectivity (only 2-fold less infectivity than those collected from cells that did not express hA3G) (FIG. 14). Therefore, while N1/2 was sufficient for viral packaging, hA3G anti-viral activity was dependent on functions within C1/2, such as dimerization and deaminase activity along with the global fold of full-length hA3G required for RNA binding.

Discussion

At present, the SAXS envelope of hA3G at nanometer resolution represents the only experimentally derived model for this important anti-viral host defense factor (Wedekind 2006). The restored hA3G shape is consistent with an elongated tail-to-tail dimer with discrete volume distributions that can make autonomously functioning domains accessible to other macromolecules in the cell. In this investigation, this hypothesis was tested by identifying discrete domains of hA3G determined by the SAXS envelope, relating them to the amino acid sequence, and subjecting them to functional end-point analyses. It was demonstrated that: (i) the individual structural domains of hA3G can be expressed as soluble proteins to the extent that they support specific cellular interactions in an isolated state; (ii) CD2 was necessary and sufficient for homodimerization of hA3G subunits, thereby validating and refining the tail-to-tail dimer predicted by SAXS; (iii) domain N1/2 comprising CD1-NCD1 was necessary for viral encapsidation and Gag binding while CD1 alone was sufficient for Vif binding; and (iv) despite the modular function of the domains, RNA interactions and anti-viral activity were not supported by any particular domain alone. Rather, these properties required the attributes of more than one functional domain, which are characteristic of full-length hA3G and/or its homo-oligomeric state.

It has been demonstrated that the two homologous catalytic domains of hA3G (CD1 and CD2) have different capacities for homodimerization, RNA binding and viral interactions. This observation is revealing since each domain is likely to exhibit a conserved cytidine deaminase three-dimensional fold (organized about the ZDD amino acid signature motif), but with the caveat that common fold does not equal a common function in this instance. This finding necessitates an empirical structural characterization of hA3G that does not rely solely on modeling of hA3G based on structural orthologs, since such molecules can display distinct oligomeric, sequence and shape differences that influence biological functions. Certainly the SAXS envelope along with biochemical data presented here, as well as gel filtration of RNase treated hA3G shown previously, supports a model in which hA3G is a dimer in the absence of RNA (Opi 2007; Chelico 2006). The fact that CD2 was sufficient for dimerization, but not NCD2, redefines the domain assessment from SAXS. Although, it cannot be ruled out that there are dimer contacts in NCD2 in full-length hA3G, the data clearly show that it is not required possibly due to a more complex protein fold that requires CD2 for stability or simply as a result of the absence of NCD2 in the interface. Overall, the results showing the behavior of hA3G in cell extracts devoid of RNA provide compelling proof that hA3G is a dimer in solution.

The elongated linear array of discrete domains revealed by the SAXS molecular envelope showed that many of these domains may be accessible for interactions with other macromolecules and therefore can function autonomously or as monomeric binding domains. The data presented here demonstrate that hA3G binding to Gag or Vif, as well as viral encapsidation, have such characteristics. It must be kept in mind that in the cell, all interactions occur in the context of full-length hA3G. In fact, RNA binding and anti-viral activity are only supported by full-length hA3G and higher-order complexes.

CD2 has been established as the catalytically active dC-to-dU deaminase domain. Homodimerization of hA3G through interactions involving CD2 can be essential for enzymatic activity. Consistent with this possibility are data showing that dimerization was essential for enzymatic activity of other APOBEC family members. Specifically, catalytically inactive mutants of APOBEC-1 had a dominant negative effect on the ability of wild type APOBEC-1 to edit apoB mRNA (Lau 1994); and dimerization deficient mutants of AID were non-functional for class switching, (a function that requires deaminase activity) (Wang 2006).

The N1/2 domain had markedly reduced anti-viral activity even though it had the ability to be packaged into virions. The simplest explanation for this finding is that N1/2 alone did not bind RNA (a prerequisite to block reverse transcription) and lacked single stranded DNA deaminase activity catalyzed by CD2. Given that only full-length hA3G bound RNA, the data showed that dimerization of hA3G enabled N1/2 RNA binding activity. Perhaps this is because RNA binding by a single N1/2 is not stable (i.e. the RNA binding scaffold is created by two low affinity N1/2 domains associated through dimerization) or appropriate folding and presentation of RNA binding sites within N1/2 is a characteristic of full-length hA3G.

Viral encapsidation and Gag binding required both CD1 and NCD1 within the N1/2 domain (a.a. 1-208). CD1 and NCD1 alone may not have been able to bind Gag because amino acids in both domains are required to coordinate Gag binding. Previous deletion mutagenesis analyses have shown that residues within a region comprising parts of both CD1 and NCD1 (a.a. 104-154) were crucial for hA3G packaging into VLPs (Luo 2004; Cen 2004). Huthoff and Malim showed that mutations within a.a. 124-127 inhibited viral encapsidations by alanine scanning (Hutoff 2007). Taken together with this analysis the data support multiple points of interaction between Gag and hA3G that involved more than one domain within hA3G.

It was demonstrated that Vif interaction with hA3G occurred through CD1 alone (a.a. 1-143). This finding supports the established role of aspartic acid 128 and select residues in the surrounding region of hA3G as being essential for Vif interaction. These findings also show that Gag binding and hA3G encapsidation (requiring CD1-NCD1) can be unaffected by therapeutics that selectively targeted the hA3G-Vif interaction.

The analysis of individual domains of hA3G in this investigation provides structural and functional insight into the organization of hA3G, as well as the autonomy of specific domains with respect to interactions with viral proteins. This analysis has enabled the identification of distinct functional units of hA3G that can be expressed as soluble proteins as demonstrated by the ability to interact with biologically relevant viral partners Gag and Vif. The solubility of N1/2, C1/2, CD1 and CD2 can provide an alternative strategy to attain hA3G structures in the context of therapeutically relevant HIV proteins.

Methods

Plasmid construction. Full-length hA3G and domains described above (C3/4, C1/2, N1/2, CD1, CD2, NCD1, and NCD2) were cloned into the pIRES-P (Hobbs 1998) vector containing either an EGFP-HA, EGFP-V5, HA, or V5 tag in the N-terminus using EcoRV and Not1 restriction sites. HIV-1 expression construct pDHIV3-GFP is a pNL4-3 derived vector that contains a deletion of the env gene and the nef gene is replaced with EGFP. The Δvif HIV-1 expression construct pDHIV3-GFP/Δvif contains a 12 base pair insert containing two termination codons that lies near residue 89 of Vif, thereby leading to the production of a truncated and non-functional vif gene product. The vif gene was also PCR amplified from pDHIV3-GFP and inserted into the pIRES-P vector containing an N-terminal EGFP-HA tag using EcoRV and Not1.

Co-immunoprecipitation analysis. Various combinations of alternatively tagged hA3G domains, HIV-1 expression constructs and EGFP-HA-Vif were transfected into 293T cells with FuGENE® 6 (Roche). 24 hours after transfection cell extracts were harvested in NP-40 lysis buffer (50 mM Tris pH 7.4, 150 mM NaCl, 0.1% NP-40) with Complete® Mini EDTA free protease inhibitors (Roche). Cell extracts were treated with 40 µg/mL of RNase A for 1 hour at 37° C. and subsequently pre-cleared with Protein A agarose beads (Roche) tumbling for 1 hour at 4° C. The pre-cleared extracts were split and added to a Protein A bead slurry±V5 (Invitrogen) or GFP antibody (Clontech) for immunoprecipitation by tumbling overnight at 4° C. The beads were washed 3 times with NP-40 lysis buffer and eluted 3 times with 1×Treat (50 mM Tris pH 7.4, 10 mM DTT, 0.1% SDS). Elutions were acetone precipitated and resuspended in SDS-PAGE gel loading buffer and run on a 10.5% SDS-PAGE. The protein was transferred to nitrocellulose (BioRAD) and western blotted with V5 (Invitrogen), HA (Convance), GFP (Clontech), or p24 (#3537, NIH AIDS Research and Reference Reagent Program) (Chesebro 1998) antibodies. Trueblot™ ULTRA anti-mouse secondary antibody (eBioscience), which does not bind to unfolded antibody, was used to prevent immunoglobulin heavy chain from being detected on western blots.

Viral Encapsidation Analysis. 293T cells were transfected with 2 µg of pDHIV3-GFP or pDHIV3-GFP/Δvif and 1 µg of EGFP-HA tagged versions of either hA3G, N1/2, CD1, NCD1, C3/4, C1/2, CD2, or NCD2 using FuGENE® 6 (Roche). 48 hours after transfection cell extracts were harvested in Reporter Lysis Buffer (Promega) with Complete® Mini EDTA free protease inhibitors (Roche) and equivalent µg quantities of protein was loaded into each lane for analysis by SDS-PAGE and western blotting with HA (Convance), β-actin (Sigma), or Vif (#6459, NIH AIDS Research and Reference Reagent Program) (Simon 1995) antibodies. Viral particles were isolated by filtering the cell media through a 0.45 micron filter followed by p24 ELISA assays (Zeptometrix) to normalize viral load. p24-equivalent amounts of viral particles were pelleted through a 20% sucrose cushion at 150,000×g for 2 hours. The viral particles were resuspended in SDS-PAGE loading buffer, boiled and analyzed by SDS-PAGE and western blotting with HA (Convance), and p24 (#3537, NIH AIDS Research and Reference Reagent Program) antibodies.

RNA UV crosslinking. A 448 nt RNA was in vitro transcribed with $^{32}$P radiolabeled ATP and CTP (NEN) using T7 polymerase (Promega). The radiolabeled RNA was gel isolated and added to cell extracts made from 293T cells expressing V5 or EGFP-V5 tagged hA3G, N1/2, C1/2, CD1, NCD1, or CD2 for 30 minutes at 4° C. The RNA was UV crosslinked to the proteins in the cell extract using short wave UV light in quartz cuvettes at 4° C. for 7 minutes as described previously (Smith 1998). Immediately after UV crosslinking cell extracts were treated with a mix of RNases T1 and A for 1 hour at 37° C. followed by preclearing and immunoprecipitations as described above. The nitrocellulose transferred protein was exposed to Biomax XAR film (Kodak) for 48 hours to identify radiolabeled bands from nucleotides covalently crosslinked to hA3G or domains. The nitrocellulose was subsequently western blotted for V5 (Invitrogen) to overlay with the radiolabeled band.

RNase protection assays. Baculovirus expressed hA3G-4-his was purified from Sf9 insect cells (provided by Immunodiagnostic Inc., MA) without RNase A treatment during purification as described previously. Equal amounts of purified protein were subjected to increasing amounts of MNase (1, 5, 10, 50, 100 Units) or RNase A (5, 50, 250, 500, 1500 ng) at 4 or 37° C. and reactions were stopped by adding TRI Reagent® (MRC, Inc.) after 20 minutes. Naked cellular RNA was also subjected to digestion by 10 Units of MNase and 250 ng of RNase A. Isolated RNA and RNA century markers (Ambion) were run on a denaturing RNA PAGE and silver stained by methods optimized for staining RNA.

Single round infectivity assays. 293T cells were transfected with pDHIV3-GFP/Δvif and pVSV-G, together with V5-hA3G, V5-N1/2, or a vector control and pseudotyped viral particles were normalized for p24 as described above. TZM-bl cells (#8129, NIH AIDS Research and Reference Reagent Program) in 96 well plates at 10,000 cells/well were infected with 6000 pg p24/mL in triplicate. 48 hours after infection, Steady Glo Reagent (Promega) was added to each well and incubated for 7 minutes before reading the luminescence in a Wallace 1420-Victor Multilabel Counter (Perkin Elmer).

Comparison of Small Angle X-ray Scattering Curves. hA3G protein purification and SAXS data collection were as described for RNase A treated samples (Wedekind 2006). One-dimensional scattering profiles for the respective crystallographic or dummy atom (i.e. hA3G) coordinates were generated by use of the program CRYSOL (Svergun 1995) and fit against the observed solution scattering profile recorded for hA3G (Wedekind 2006). The generation of a representative hA3G dummy atom model and fit to the experimental scattering curve were by use of the programs GNOM (Svergun 1992) and DAMMIN (Svergun 1997) as described previously (Wedekind 2006).

RT-PCR Analysis. Isolated RNA that co-purified with hA3G (purified without RNase A as described previously in Wedekind 2006) was annealed to oligodT (0.5 mg/ml) at 65° C. for 10 minutes and ramp cooled for 40 minutes. First-strand cDNA synthesis was performed with 2.5 mM MgCl$_2$, 1XRT buffer, 1 mM dNTPs, 5-10U RNasin, ±5U AMV reverse transcriptase (Promega) at 42° C. for one hour. Reactions were heated to 99° C. for 5 minutes and then crashed on ice for 2 minutes. Polymerase chain reaction was then used to amplify cDNA using 1 mM of each paired primer for hA3G mRNA

```
5' primer:
                                    (SEQ ID NO: 3)
CTCGAATTCAGGGATGAAACCTCACTTCAGAAACACAGTG 3' primer:
                                    (SEQ ID NO: 4)
CTGGAGAATGGCCCGCAG 18S rRNA
5' primer:
                                    (SEQ ID NO: 5)
GATAACTGTGGTAATTCTAGAG 3' primer:
                                    (SEQ ID NO: 6)
GTAATTTGCGCGCCTGCTG
or 28S rRNA
5' primer:
                                    (SEQ ID NO: 7)
GAGCCCAGCGCCGAATCC 3' primer:
                                    (SEQ ID NO: 8)
CTCTTGAACTCTCTCTTCAAAG
```

10 mM dNTPs, 5 µL of the RT reaction, 2.5 mM MgCl$_2$, and Taq polymerase (Promega) for 30 cycles as described previously[5]. PCR reactions were resolved on a 1% agarose gel containing ethidium bromide for visualization of DNA bands.

RNA UV Crosslinking. hA3G was purified without RNase A as described previously (Wedekind 2006). hA3G concentrations of 0.75 and 1.5 µg were UV crosslinked to in vitro transcribed RNAs from either the first 520 nt of HIV-1 or the region between nt 6413-6860 of apoB mRNA (7.4% identity) as described previously (Smith 1998). The protein was acetone precipitated, run on SDS-PAGE and the gel was exposed to Biomax XAR Film (Kodak) for 12 hours (FIG. 17). Also, UV crosslinking was performed as described in Methods except that pDHIV3-GFP was co-transfected with hA3G or N1/2 (FIG. 18).

Example 3

Nuclear Exclusion of the HIV-1 Host Defense Factor APOBEC3G Requires a Unique Cytoplasmic Retention Signal Human APOBEC3G (hA3G) is a host factor that defends against HIV-1 as well as other exogenous retroviruses and endogenous retroelements. To this end, hA3G is restricted to the cytoplasm of T lymphocytes where it interacts with viral RNA and proteins to assemble with viral particles causing a post-entry block during reverse transcription. hA3G also exhibits a mechanism to inhibit the reverse transcription of retroelements by RNA binding and sequestration into mRNA processing centers in the cytoplasm. It has been determined that the molecular basis for this specialized property of hA3G is a novel cytoplasmic retention signal (CRS) that is necessary and sufficient to restrict wild type hA3G and chimeric constructs to the cytoplasm. The CRS resides within amino acids 113-128 and is embedded within a basic flanking sequence. Paralogs of hA3G that have nuclear or cytoplasmic distributions differ from hA3G within the region encompassing the CRS motif with respect to charge and amino acid composition. It is herein proposed that the CRS of hA3G serves a vital role in host cell defense by restricting an antiviral sentinel to the cytoplasm. Identification of this motif has important implications for the design of therapeutics that target HIV-1 while maintaining the suppression of retroelements.

Cytidine deaminases of the APOBEC family (ApoB mRNA Editing Catalytic subunit) have one or more zinc dependent deaminase (ZDD) signature motifs of the form (C/H)xEx$_n$PCxxC that is characteristic of enzymes that use RNA or single stranded DNA (ssDNA) as substrates for C to U or dC to dU deamination (Jarmuz 2002; Wedekind 2003). APOBEC-1, activation induced deaminase (AID) and APOBEC3G are the most extensively characterized members of this family. In mammals APOBEC-1 carries out site-specific editing of apoB and NF1 mRNAs to produce nonsense codons that lead to truncated proteins with altered functional properties 1996). Though not observed under physiological conditions, APOBEC-1 can carry out dC to dU ssDNA mutation when expressed under selection in an *E. coli*-based DNA mutator assay (Harris 2002). In contrast, the physiological function of AID in germinal center B cells is to carry out multiple dC to dU mutations on ssDNA regions within the variable region and switch regions of immunoglobulin genes as an essential mechanism for somatic hypermutation and class switch recombination, respectively (Honjo 2004; Muramatsu 2000).

The activities of APOBEC-1 and AID are regulated through their tissue-specific and temporal expression during cell differentiation (Muramatsu 2000; Huguchi 1992; Muramatsu 1999; Papavasiliou 2000; von Wronski 1998). Both enzymes have cytoplasmic and nuclear distributions within cells but the RNA and ssDNA editing activity of APOBEC-1 and AID are restricted to the cell nucleus (Lau 1991; Nambu 2003; Sowden 2002; Yang 1997; Ito 2004; Chester 2003; Brar 2004; Ta 2003; Chaudhuri 2004; Barreto 2003; Yang 1997). Each enzyme has a nuclear localization signal (NLS) and a nuclear export signal (NES) (Nambu 2003; Sowden 2002; Yang 1997; Ito 2004) and their interaction with cytoplasmic chaperones is essential for nuclear import and site-specific editing activities (Lau 1991; Chester 2003; Brar 2004; Ta 2003; Chaudhuri 2004; Barreto 2003; Yang 1997). Overexpression of such enzymes and their production in cell types lacking regulatory chaperones results in promiscuous editing activity on RNA and DNA (Sowden 1996; Yamanaka1996). This nonspecific activity can lead to cell transformation and cancer (Oppezzo 2003; Okazaki 2003; Yamanaka 1995; Yamanaka1997; Babbage 2006; Duquette 2005; Rucci 2006).

In contrast to APOBEC-1 and AID, the ssDNA deaminase human APOBEC3G (hA3G) has N- and C-terminal ZDD motifs that contribute to RNA binding and dC to dU conversion in the context of ssDNA, respectively (Mangeat 2003; Navarro; 2005; Newman 2005; Sheehy 2002; Yu 2004; Zhang 2003). hA3G, along with other APOBEC3 paralogs, serves as a host defense factor against exogenous retroviruses and endogenous retroelements (Bogerd 2006; Muckenfuss 2006; Esnault 2005; Chiu 2006; Kinomoto 2007). hA3G is the most potent inhibitor of vif-deficient HIV-1 infectivity in the APOBEC family (Bishop 2004). Of particular interest is that hA3G is restricted to the cytoplasm of T lymphocytes where it has diffuse as well as punctuate distributions (Wichroski 2006; Kozak 2006; Wichroski 2005; Bennett 2006). The localization of hA3G is functionally significant for each of its known activities. hA3G has an intrinsic ability to bind to RNA, and its cytoplasmic localization enables it to bind HIV-1 and retroviral/retroelement RNA. Cytoplasmic localization also enables hA3G to block reverse transcription for both HIV-1 (Chiu 2005) and hepatitis B virus (Nyguen 2007). hA3G also is bound to retroelement RNA as high molecular mass (HMM) complexes, and this has been posited to block their replication by sequestration within stress granules and p-bodies (Gallois-Montbrun 2007). Several proteins co-purify with HMM complexes but most are indirectly associated with hA3G via an RNA bridge. Recently, hA3G has been shown to enhance the stability and translation of cellular mRNAs that would be otherwise targeted for degradation by micro RNA (miRNA) by excluding them from p-bodies and enhancing their association with polysomes (Huang 2007). Finally, HIV-1 Vif inhibits hA3G activity by shuttling hA3G to proteasomal degradation (Mariani 2003; Mehle 2004; Stopak 2003; Yu 2003). However, in the absence of Vif, hA3G is packaged within HIV-1 virions in the cytoplasm through interactions with RNA and the nucleocapsid (NC) portion of the HIV-1 Gag polyprotein (Burnett 2007; Svarovskaia 2004; Khan 2005; Schafer 2004; Zennou 2004; Luo 2004; Cen 2004; Alce 2004). Viral packaging provides spatially privileged access of hA3G to the reverse transcription complex and enables it to block viral replication as well as catalyze dC to dU hypermutations of single stranded newly replicated proviral DNA (Bishop 2006; Guo 2006; Harris 2003). Cytoplasmic retention of hA3G can also be important as a means to prevent genotoxicity due to hA3G activity on chromosomal DNA as has been observed for uncontrolled APOBEC-1 and AID expression.

Described herein is the identification of a novel cytoplasmic retention signal (CRS). Although hA3G has no NLS, it is shown that the CRS can act dominantly over an NLS from the SV40 large T antigen (Kalderon 1984). The crucial components of the CRS map to a 16 a.a. region adjacent to the first ZDD motif (a.a. 113-128) that overlaps with critical residues for both HIV-1 Gag and Vif interactions (Schrofelbauer 2006; Mangeat 2004; Schrofelbauer 2004; Huthoff 2007). It is shown that this region is both necessary and sufficient for cytoplasmic retention of reporter constructs that are otherwise nuclear. These findings explain why hA3G is restricted to the cytoplasm and are relevant in the rational design of novel HIV/AIDS therapeutics.

Results

The CRS is within the N-terminal Half of hA3G. Previously, indirect immunostaining of fixed HeLa cells was utilized to determine that hA3G was actively retained in the cytoplasm even when a strong NLS from SV40 was added onto the protein. Focusing on the cis-acting sequence determinants for the cytoplasmic localization of hA3G, a live cell assay system was established using transfection of chimeric proteins containing enhanced green fluorescent protein (EGFP) or NLS-EGFP. This reporter system enabled visualization of the subcellular distribution of hA3G and parts thereof. EGFP was selected because it has no subcellular localization determinants (diffuses freely throughout the cell) and it, along with its derivatives (i.e. YFP and CFP), has been shown not to affect hA3G functionality or localization when attached to the N-terminus of hA3G reporter constructs.

Figure 19A:
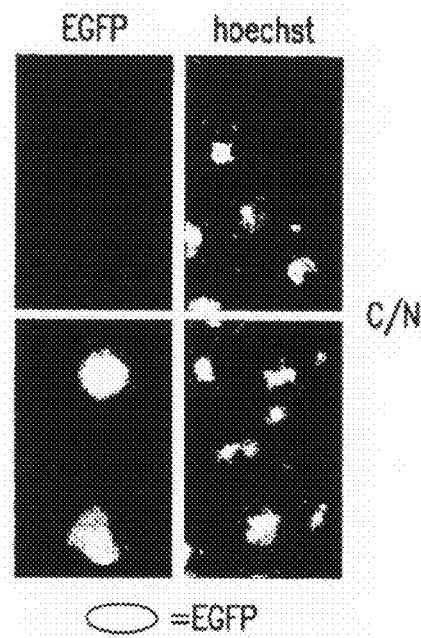
Figure 19B:
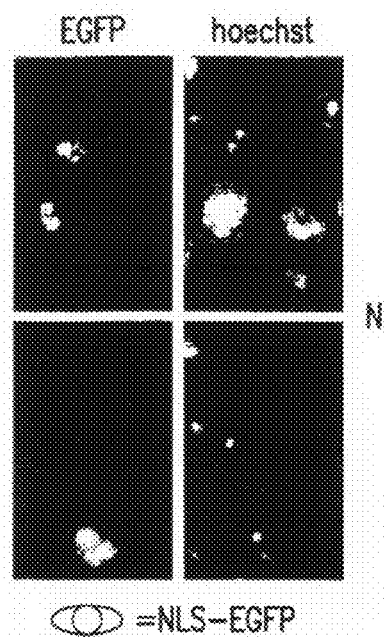
Figure 19C:
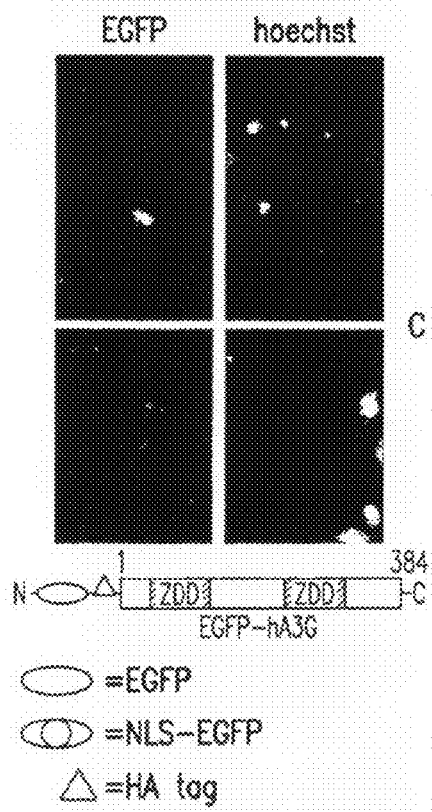
Figure 19D:
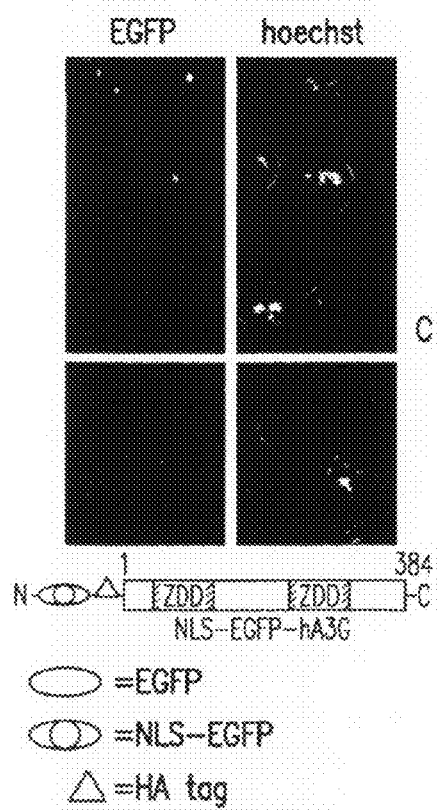

As expected, EGFP alone was distributed homogenously throughout both the cytoplasm and nucleus of 293T cells (FIG. 19A). The addition of the SV40 NLS to EGFP (NLS-EGFP) resulted in near quantitative nuclear localization of the chimeric protein (FIG. 19B). However, when hA3G was attached to the C-terminus of EGFP or NLS-EGFP the chimeric proteins demonstrated a cytoplasmic localization (FIGS. 19C and D).

Each half of hA3G contains a consensus ZDD motif and have 62.8% similarity in pairwise amino acid sequence relatedness (Table 4). To begin to determine the position of the CRS within hA3G the N-terminal half (a.a. 1-208) and C-terminal half (a.a. 209-384) of hA3G were attached to NLS-EGFP (NLS-EGFP-NT and NLS-EGFP-CT, respectively) and expressed in 293T cells. Whereas NLS-EGFP-NT was cytoplasmic (FIG. 19E), NLS-EGFP-CT had a predominant nuclear localization (FIG. 19F). This established the N-terminal portion of hA3G as the region containing the CRS. Western blotting with anti-GFP or anti-HA confirmed that all chimeric proteins were expressed and were of the expected size (FIG. 19G).

Mapping the CRS with NLS-EGFP. FIG. 20 shows the predicted secondary structure of hA3G based on sequence alignment with the known crystal structures of APOBEC-2 and other cytidine deaminases (Prochnow 2007; Wedekind 2006) as well as exon junctions. Deletion constructs of the N-terminal half of hA3G were prepared using predicted loop regions of hA3G as break points to avoid disrupting predicted secondary structural elements. All hA3G deletions constructs were prepared as NLS-EGFP chimeric proteins and transfected into 293T cells and validated for their expression by western blotting.

Figure 21K:
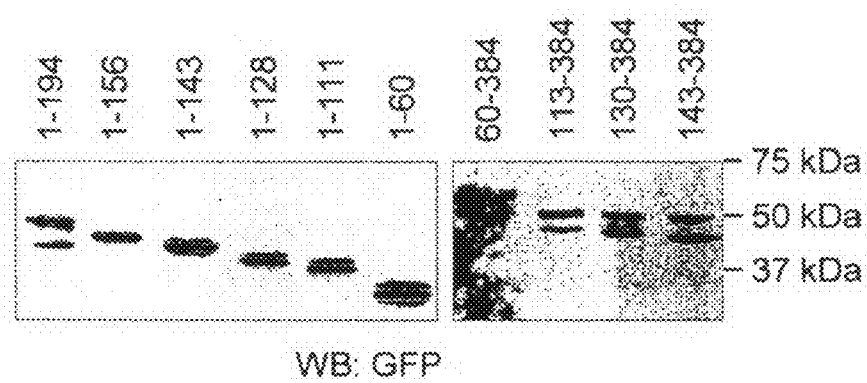

Deletion of 14 residues from the C-terminus of the N-terminal half (a.a. 1-194) did not affect the cytoplasmic retention of the chimeric protein (FIG. 21A). However, deletion of predicted alpha helix five (α5) located between two exon junctions (FIG. 20) in the construct containing a.a. 1-156 resulted in partial distribution of the chimeric protein to the nucleus (FIG. 21B). This showed that the CRS had been weakened and that the NLS function was partially able to compete with the CRS. Further deletion (to a.a. 1-143 and a.a. 1-128) did not alter the cytoplasmic and nuclear distribution of the chimeric proteins (FIGS. 21C and D). Deletion of the predicted beta strand 4 (β4) (a.a. 1-111) or further (a.a. 1-60) resulted in a prominent nuclear accumulation of the chimeric protein as expected from the SV40 NLS containing reporter (FIGS. 21E and F). Expression of the appropriate molecular mass for each construct was confirmed by western blotting (FIG. 21K). These data suggested that the CRS mapped to a region including the predicted β4 within the N-terminus of hA3G.

To confirm these data, progressively smaller constructs from the N-terminus of hA3G were made as NLS-EGFP chimeric proteins and transfected into 293T cells. Chimeric proteins lacking the first 59 amino acids (a.a. 60-384) were restricted to the cytoplasm (FIG. 21G). Chimeras with a deletion of the first 112 a.a., which removed the ZDD motif, had predominantly cytoplasmic distribution with some nuclear distribution (FIG. 21H). Further deletion of the first 129 a.a. (FIG. 21I) and 143 a.a. (FIG. 21J) resulted in a predominant nuclear localization of chimeric proteins. As with the constructs above western blots with anti-GFP established that the reporter constructs were expressed and had the expected sizes (FIG. 21K).

Together, these data showed that a.a. 60-194 were required to completely restrict hA3G to the cytoplasm in the presence of NLS-EGFP and that the ZDD motif and the predicted α5 may contribute structural elements. However, the CRS itself must reside between a.a. 113-128 in the predicted β4 because reporter constructs lacking this region were predominantly nuclear (FIGS. 3E and I).

Figure 22A:
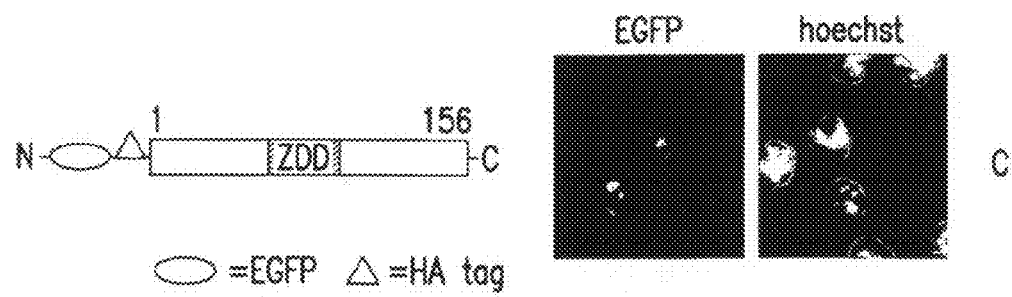
Figure 22B:
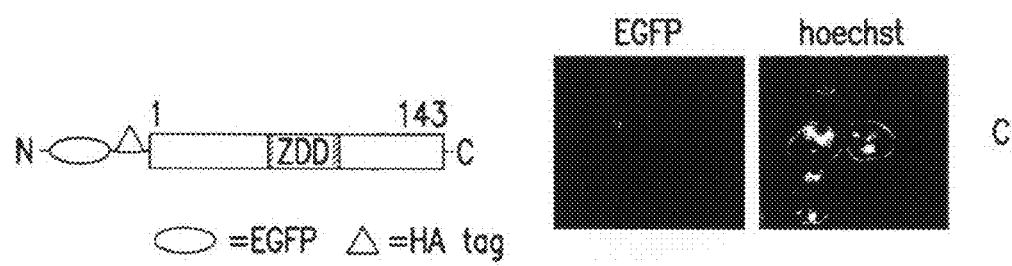
Figure 22C:
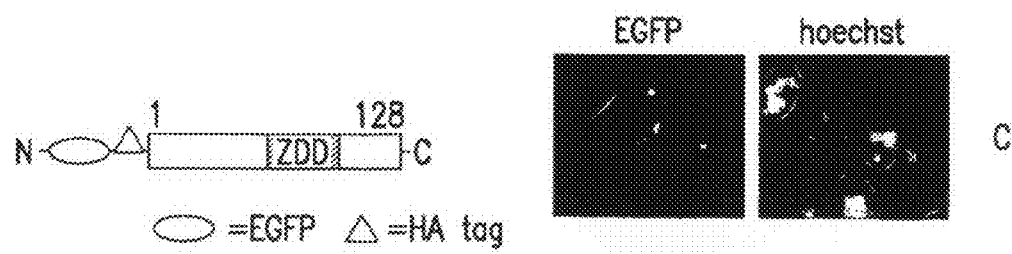

Mapping the CRS with EGFP. Native hA3G does not contain an NLS and does not traffic. In the foregoing experiments the SV40 NLS was used to rapidly focus on the occurrence and position of a CRS within hA3G sequence. In the absence of an NLS or CRS, EGFP has a homogeneous distribution determined by diffusion. To further define the boundaries of the hA3G CRS, deletion constructs were made as EGFP chimeras lacking the SV40 NLS with the anticipation that the hA3G CRS would restrict diffusion of these proteins to the cytoplasm. As expected, all deletion constructs that contained β4 (a.a. 1-156, 1-143, 1-128) had robust cytoplasmic localization (FIG. 22A-C). Alternatively, constructs lacking this region (a.a. 1-60, 1-111) distributed to both the cytoplasm and nucleus (FIGS. 4D and E), similar to that observed with EGFP alone (FIG. 19A) suggesting the loss of CRS function. The data corroborate findings with NLS-EGFP chimeric deletion constructs of hA3G suggesting that the region including the predicted β4 is essential for cytoplasmic retention.

Figure 22D:
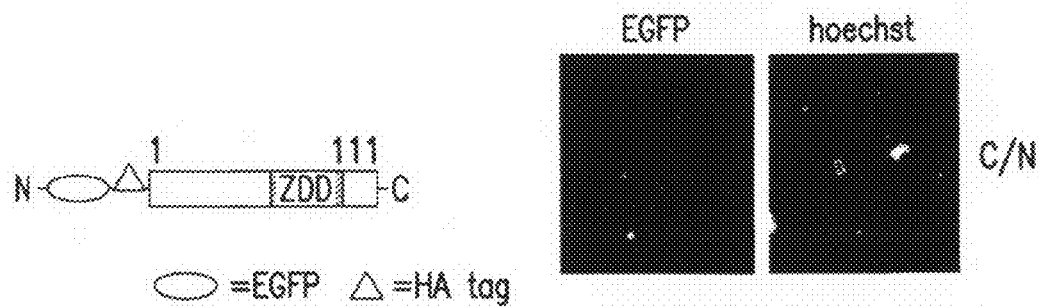
Figure 22E:
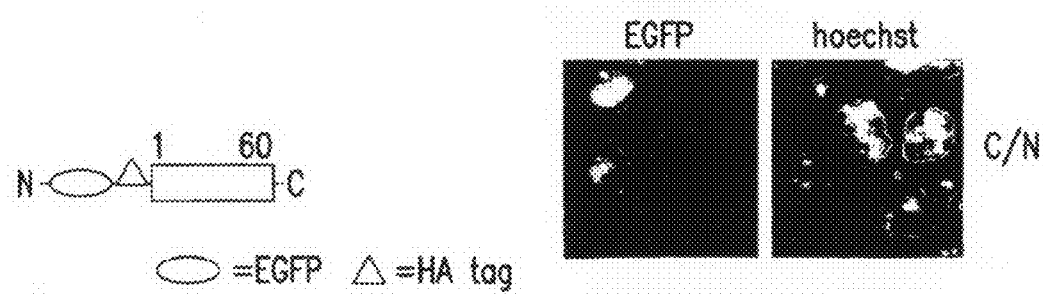
Figure 23B:
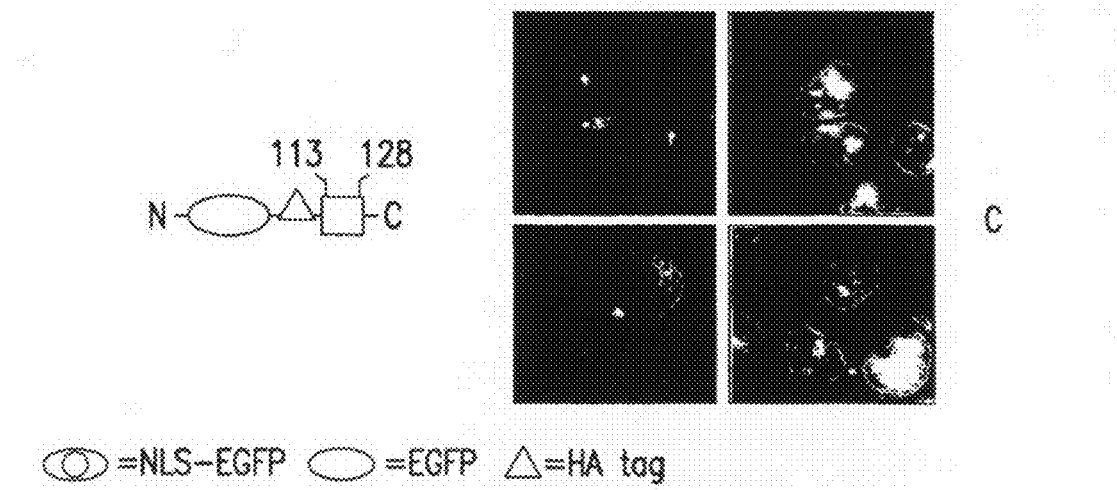
Figure 23C:
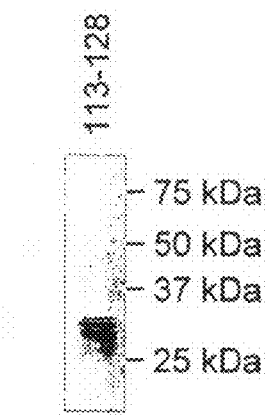

The hA3G-CRS is Autonomously Capable of Cytoplasmic Retention of Reporters. The ability of the region including the predicted β4 (a.a. 113-128) was tested to act autonomously as a CRS when attached to the C-terminus of either, NLS-EGFP or EGFP. This motif alone was only partially dominant over the SV40 NLS and these chimeric proteins displayed both cytoplasmic and nuclear localization (FIG. 23A) compared to robust nuclear retention with NLS-EGFP alone (FIG. 23B). On the other hand, this motif was sufficient for robust cytoplasmic retention of EGFP (FIG. 23B) compared to EGFP alone. As with the constructs in FIGS. 19 and 21 a western blot with anti-GFP confirmed that the EGFP reporter constructs had the expected size (FIG. 23C). The fact that this small region retained EGFP in the cytoplasm reveals that indeed the CRS motif was responsible for cytoplasmic retention and not the relative size of the chimeric proteins above, because larger constructs lacking this motif were capable of diffusing to the nucleus (FIGS. 22D and E). These data demonstrated that the region containing residues KVTLTIFVARLYYFWD was a novel CRS motif that functions to restrict hA3G to the cytoplasm.

TABLE 4

Pairwise amino acid sequence relatedness of APOBEC3 paralogs.

| paralogs | % identity | % similarity | pI | CRS motif | SEQ ID NO: |
|---|---|---|---|---|---|
| †hA3G-NT | 100 | 100 | 9.4 | $^{113}$KVTLTIFVARLYYFWD$^{128}$ | 9 |
| hA3F-NT | 61.9 | 77.3 | 8.9 | $^{112}$N***SA***Y*E$^{127}$ | 10 |

TABLE 4-continued

Pairwise amino acid sequence relatedness of APOBEC3 paralogs.

| paralogs | % identity | % similarity | pI | CRS motif | SEQ ID NO: |
|---|---|---|---|---|---|
| hA3B-NT | 49.7 | 71.1 | 7.5 | $^{113}$N***SA****Y*E$^{128}$ | 10 |
| hA3C | 43.1 | 67.5 | 6.8 | $^{113}$N*N**T****QY$^{128}$ | 11 |
| hA3A | 34.6 | 64.4 | 6.3 | $^{119}$H*R*RAI*DYDP$^{134}$ | 12 |
| hA3G-CT | 33.2 | 62.8 | 5.9 | $^{304}$H*S*CTI*DDQG$^{319}$ | 13 |
| hA3F-CT | 42.6 | 63.8 | 5.5 | $^{296}$N*N**T*******$^{311}$ | 14 |
| hA3B-CT | 35.7 | 62.4 | 5.1 | $^{302}$H*R*RAI*DYDP$^{317}$ | 15 |

†The amino acid sequence of the N-terminus of hA3G (hA3G-NT, a.a. 1-194) was used as a reference to compare to the homologous region of other APOBEC3 paralogs with known localizations for percent amino acid identity and similarity. Theoretical isoelectric point (pI) of these regions were calculated by ProtParam (76) and grouped according to relative pIs as basic (white), neutral (light gray), or acidic (dark gray). APOBEC3G, -3F, and -3B contain two ZDD moitifs and halves of each were compared to hA3G-NT (hA3G-CT, hA3F-NT, hA3F-CT, hA3B-NT, hA3B-CT) and APOBEC3A and -3C contain only one ZDD thus the full-length proteins were compared to hA3G-NT (hA3C and hA3A). The sequences of the regions that are homologous to the 16 amino acid CRS motif of hA3G are listed with (*) for identical residues and differing amino acids are listed for hA3G paralogs.

Discussion

Whether hA3G is actively retained in the cytoplasm through its own cytoplasmic retention signal (CRS) was tested by evaluating the subcellular distribution of hA3G domains expressed as EGFP and NLS-EGFP chimeric reporters. It was demonstrated that the sequence KVTLTIFVARLYYFWD (a.a. 113-128, SEQ ID NO: 9) within the N-terminal portion of hA3G is a novel CRS that restricts hA3G to the cytoplasm and is capable of autonomous function within the context of chimeric reporters. An important consideration in the experimental design was that regions of hA3G were selected for evaluation based on secondary structure domain boundaries predicted from the known crystal structure of APOBEC-2 and other cytidine deaminases as well as the solution structure of APOBEC3G. In the absence of an atomic resolution structure for hA3G, this is a directed approach for deletion mapping that has reasonable expectations for maintaining functional domain integrity such that folded, soluble regions of hA3G can be expressed. An additional strength in the experimental design lies in the ability to evaluate the subcellular distribution determinants of hA3G in living cells through the use of an EGFP fluorescent reporter. When expressed alone, EGFP is uniformly and diffusely distributed in the nucleus and cytoplasm as it lacks a subcellular localization determinant. The addition of a strong nuclear localization signal from the SV40 large T antigen resulted in quantitative retention of NLS-EGFP in the nucleus. Our initial analyses showed that hA3G and APOBEC-1 acted dominantly over the SV40 NLS. It was also shown that unlike APOBEC-1 or AID, hA3G does not traffic between the cytoplasm and nucleus. This enabled a simple experimental design wherein chimeric NLS-EGFP reporters containing domains of hA3G with CRS activity can be positively identified by their ability to induce cytoplasmic localization of an otherwise nuclear restricted NLS-EGFP reporter.

The data showed that a stretch of 16 amino acids was a powerful cytoplasmic determinant capable of excluding reporters lacking an NLS entirely from the nucleus, and markedly reducing the ability of NLS-EGFP to be retained in the nucleus. The data also showed that within the native sequence context of the N-terminus of hA3G, the CRS activity was dominant over the SV40 NLS. This characteristic showed that elements surrounding the CRS, such as secondary structure or charge, promoted or enhanced the function of the CRS.

The N-terminal half of hA3G has a distinctly basic sequence with a theoretical isoelectric point (pI) of 9.4 (Table 4). APOBEC3F (hA3F) also is localized exclusively in the cytoplasm and the homologous CRS region in the N-terminus pI lies within a basic sequence (pI=8.9) (Table 4). The other APOBEC3 paralogs hA3B, hA3C and hA3A all have predominantly nuclear localizations in transfected cells and have close to neutral theoretical pI in their homologous regions. Also, the C-terminal half of the two ZDD containing family members (hA3G, hA3F, and hA3B) are all distinctly acidic (Table 4). This shows that in the native context the hA3G-CRS is most effective in a basic environment.

The CRS residues KVTLTIFVARLYYFWD (SEQ ID NO: 9) are highly conserved among non-human primate APOBEC3Gs. The motif in chimpanzees is identical to humans and only the difference in African green monkeys and maquaces is D128K, which has been shown by multiple labs to be an essential amino acid for HIV-1 or SIV Vif interaction. Moreover, there is a considerable amount of conservation of the motif in other APOBEC3 paralogs with the major differences being at residues K113, T115, and V120 (Table 4). Possible reasons for nuclear localization of some APOBEC3 family members could be that they are lacking key residues for cytoplasmic retention, the motif is buried and not surface exposed or the charge environment around the motif (Table 4) prohibits its ability to function as a CRS. On the other hand, the fact that this region has been shown to contain important residues for both HIV-1 Gag (a.a. 124-127) and Vif (D128) interactions suggests that this motif is surface exposed in hA3G. The hA3G molecular envelope restoration demonstrated that it dimerized through interactions within the C-terminus and has an elongated conformation wherein the CRS is predicted to be exposed to solvent.

Identification of the hA3G CRS is significant because the well studied anti-viral activity of hA3G is a cytoplasmic phenomenon. The block to HIV-1 reverse transcription, hypermutation of ssDNA replicating HIV-1 proviral DNA and assembly with HIV-1 virions all occur in the cytoplasm. In fact, the ability of hA3G to sequester endogenous retroelement RNAs in the cytoplasm has been proposed as a mechanism to inhibit their reverse transcription and genomic re-integration of retrotransposable intermediates. HIV-1 Vif interacts with hA3G in the cytoplasm to induce its ubiquitination and degradation. In fact, Wichroski et al. showed that Vif and a degradation-deficient mutant thereof (C114S) were predominantly nuclear in the absence of hA3G, but when co-expressed with hA3G were re-distributed to the cytoplasm providing further evidence for dominance of the CRS within hA3G.

APOBEC family members such as APOBEC-1 and AID exert their activities in the cell nucleus but their entry into the nucleus is regulated through tissue-specific and temporal expression and through interactions with cytoplasmic proteins as molecular chaperones. Given that dysregulation of APOBEC-1 and AID results in promiscuous editing activity that leads to cancer, the presence of CRS in hA3G that lacks an NLS may have been selected because this combination in hA3G (and perhaps hA3F) ensures that sufficient protein to saturate binding to retroviral/retroelement RNAs can be expressed while ensuring that the hA3G cannot diffuse into the nucleus and induce genomic hypermutations.

The identification of the hA3G-CRS has important implications for the development of anti-HIV-1 therapeutics that target the interaction of Vif and hA3G. The regions of hA3G that are involved in Vif binding and Gag binding overlap with the CRS. Viral encapsidation is central to the anti-viral mechanism of action for hA3G and therefore therapeutics must be selected that block the interaction of Vif and hA3G, while maintaining hA3G CRS function and Gag binding.

Methods

Plasmid Construction. Full-length hA3G, and deletion mutants (a.a. 1-208, 1-194, 1-156, 1-143, 1-128, 1-111, 1-60, 60-384, 113-384, 130-384, 144-384, 209-384, and 113-128) were PCR amplified and cloned with restriction sites EcoRV and No1 into the pIRES-P vector with N-terminal reporter constructs of either EGFP-HA or NLS-EGFP-HA. Amino acids PKKKRKV (SEQ ID NO: 16) (NLS from SV40 large T-antigen) were added to the N-terminus of EGFP to create NLS-EGFP.

Transfections, Live Cell Imaging and Western Blotting. 293T cells obtained from ATCC (Manassas, Va.) were transfected using FuGENE® 6 according to the manufacture's protocol (Roche). Twenty-four hours after 293T cells were transfected 10 μM final concentration of hoechst 33342 (Anaspec Inc., San Jose, Calif.) was added to the cell media and cells were imaged by a QICIM-IR fast 12 bit mono chrome camera viewed by Q capture software (Q-Imaging) through a 40× Olympus objective with an Olympus IX 70 inverted fluorescence microscope and label specific chrome filters. After imaging, cells were harvested in Reporter Lysis Buffer (Promega). Cell extracts were run on a 10.5% SDS-PAGE and transferred to nitrocellulose where proteins were detected by western blotting with antibodies: anti-HA (Convance) or anti-GFP (Roche) and a goat anti-mouse secondary (eBioscience).

G. References

Alce, T. M. & Popik, W. APOBEC3G is incorporated into virus-like particles by a direct interaction with HIV-1 Gag nucleocapsid protein. *J Biol Chem* 279, 34083-6 (2004).

Babbage, G., Ottensmeier, C. H., Blaydes, J., Stevenson, F. K. & Sahota, S. S. *Cancer Res* 66, 3996-4000 (2006).

Barreto, V., Reina-San-Martin, B., Ramiro, A. R., McBride, K. M. and Nussenzweig, M. C. *Mol Cell* 12, 501-508 (2003).

Bennett, R. P. et al. APOBEC-1 and AID are nucleo-cytoplasmic trafficking proteins but APOBEC3G cannot traffic. *Biochem Biophys Res Commun* 350, 214-9 (2006).

Betts, L., Xiang, S., Short, S. A., Wolfenden, R., and Carter, C. W., Jr. *J Mol Biol* 235, 635-656 (1994).

Bishop, K. N., Holmes, R. K. & Malim, M. H. Antiviral potency of APOBEC proteins does not correlate with cytidine deamination. *J Virol* 80, 8450-8 (2006).

Bishop, K. N., Holmes, R. K., Sheehy, A. M., Davidson, N. O., Cho, S. J. & Malim, M. H. *Curr Biol* 14, 1392-6 (2004).

Bogerd, H. P., Wiegand, H. L., Doehle, B. P., Lueders, K. K. & Cullen, B. R. *Nucleic Acids Res* 34, 89-95 (2006).

Bransteitter, R., Pham, P., Scharff, M. D. & Goodman, M. F. Activation-induced cytidine deaminase deaminates deoxycytidine on single-stranded DNA but requires the action of RNase. *Proc Natl Acad Sci USA* 100, 4102-7 (2003).

Brar, S. S., Watson, M. & Diaz, M. *J Biol Chem* 279, 26395-401 (2004).

Burnett, A. & Spearman, P. APOBEC3G multimers are recruited to the plasma membrane for packaging into human immunodeficiency virus type 1 virus-like particles in an RNA-dependent process requiring the NC basic linker. *J Virol* 81, 5000-13 (2007).

Cen, S. et al. The interaction between HIV-1 Gag and APOBEC3G. *J Biol Chem* 279, 33177-84 (2004).

Chacon, P., and Wriggers, W. *J Mol Biol* 317, 375-384 (2002).

Chaudhuri, J., Khuong, C. & Alt, F. W. *Nature* 430, 992-8 (2004).

Chelico, L., Pham, P., Calabrese, P. & Goodman, M. F. APOBEC3G DNA deaminase acts processively 3'-->5' on single-stranded DNA. *Nat Struct Mol Biol* 13, 392-9 (2006).

Chen, K., Huang, J., Zhang, C., Huang, S., Nunnari, G., Wang, F. X., Tong, X., Gao, L., Nikisher, K., and Zhang, H. *J Virol* 80, 7645-7657 (2006).

Chen, S. H., Habib, G., Yang, C. Y., Gu, Z. W., Lee, B. R., Weng, S. A., Silberman, S. R., Cai, S. J., Deslypere, J. P., Rosseneu, M. & et al. *Science* 238, 363-6 (1987).

Chesebro, B., Wehrly, K., Nishio, J. & Perryman, S. Macrophage-tropic human immunodeficiency virus isolates from different patients exhibit unusual V3 envelope sequence homogeneity in comparison with T-cell-tropic isolates: definition of critical amino acids involved in cell tropism. *J Virol* 66, 6547-54 (1992).

Chester, A., Somasekaram, A., Tzimina, M., Jarmuz, A., Gisbourne, J., O'Keefe, R., Scott, J. & Navaratnam, N.) *Embo J* 22, 3971-82 (2003).

Chiu, Y. L. et al. High-molecular-mass APOBEC3G complexes restrict Alu retrotransposition. *Proc Natl Acad Sci USA* 103, 15588-93 (2006).

Chiu, Y. L. et al. Cellular APOBEC3G restricts HIV-1 infection in resting CD4+T cells. *Nature* 435, 108-14 (2005).

Chung, S. J., Fromme, J. C., and Verdine, G. L. *J Med Chem* 48, 658-660 (2005).

Delano, W. L. DeLano Scientific, San Carlos (2002).

Duquette, M. L., Pham, P., Goodman, M. F. & Maizels, N. *Oncogene* 24, 5791-8 (2005).

Esnault, C., Heidmann, O., Delebecque, F., Dewannieux, M., Ribet, D., Hance, A. J., Heidmann, T. & Schwartz, O. *Nature* 433, 430-3 (2005).

Feigin, L. A., and Svergun, D. I. *Structure Analysis by Small Angle X-ray and Neutron Scattering*, 1 Ed., Plenum Press, New York (1987).

Gallois-Montbrun, S. et al. Antiviral protein APOBEC3G localizes to ribonucleoprotein complexes found in P bodies and stress granules. *J Virol* 81, 2165-78 (2007).

Gasteiger, E., Hoogland, C., Gattiker, A., Duvaud, S., Wilkins, M. R., Appel, R. D. & Bairoch, A. in *The Proteomics Protocols Handbook*, eds Walker, J. M. (Humana Press, Totowa, N.J.), pp 571-607 (2005).

Glatter, O. *J. Appl. Cryst.* 10, 415-421 (1977).

Gill, S. C., and von Hippel, P. H. *Anal Biochem* 182, 319-326 (1989).

Guinier, A., and Fournet, G. *Small Angle Scattering of X-rays*, John-Wiley & Sons, New York (1955).

Guo, F., Cen, S., Niu, M., Saadatmand, J. & Kleiman, L. Inhibition of formula-primed reverse transcription by human APOBEC3G during human immunodeficiency virus type 1 replication. *J Virol* 80, 11710-22 (2006).

Hammel, M., Fierobe, H. P., Czjzek, M., Kurkal, V., Smith, J. C., Bayer, E. A., Finet, S., and Receveur-Brechot, V. *J Biol Chem* 280, 38562-38568 (2005).

Harris, R. S., Bishop, K. N., Sheehy, A. M., Craig, H. M., Petersen-Mahrt, S. K., Watt, I. N., Neuberger, M. S., and Malim, M. H. *Cell* 113, 803-809 (2003).

Harris, R. S., Petersen-Mahrt, S. K. & Neuberger, M. S. *Mol Cell* 10, 1247-53 (2002).

Heiney, P. 2.07 Ed., University of Pennsylvania (2006).

Hobbs, S., Jitrapakdee, S. & Wallace, J. C. Development of a bicistronic vector driven by the human polypeptide chain elongation factor 1alpha promoter for creation of stable mammalian cell lines that express very high levels of recombinant proteins. *Biochem Biophys Res Commun* 252, 368-72 (1998).

Honjo, T., Muramatsu, M. & Fagarasan, S. *Immunity* 20, 659-68 (2004).

Huang, J., Liang, Z., Yang, B., Tian, H., Ma, J. & Zhang, H. *J Biol Chem*. (2007).

Huguchi, K., K., Kitagawa, K., Kogishi and T. Takeda, *J. Lipid Res.* 33, 1753-1764 (1992).

Huthoff, H. & Malim, M. H. *J Virol* 81, 3807-15 (2007).

Huthoff, H., and Malim, M. H. *Virology* 334, 147-153 (2005).

Ito, S., Nagaoka, H., Shinkura, R., Begum, N., Muramatsu, M., Nakata, M. & Honjo, T. *Proc Natl Acad Sci USA* 101, 1975-80 (2004).

Iwatani, Y., Takeuchi, H., Strebel, K., and Levin, J. G. *J Virol* 80, 5992-6002 (2006).

Jarmuz, A., Chester, A., Bayliss, J., Gisbourne, J., Dunham, I., Scott, J., and Navaratnam, N. *Genomics* 79, 285-296 (2002).

Johansson, E., Mejlhede, N., Neuhard, J., and Larsen, S. *Biochemistry* 41, 2563-2570 (2002).

Johs, A., Hammel, M., Waldner, I., May, R. P., Laggner, P., and Prassl, R. *J Biol Chem* 281, 19732-19739 (2006).

Kalderon, D., Roberts, B. L., Richardson, W. D. & Smith, A. E. *Cell* 39, 499-509. (1984).

Khan, M. A. et al. Viral RNA is required for the association of APOBEC3G with human immunodeficiency virus type 1 nucleoprotein complexes. *J Virol* 79, 5870-4 (2005).

Kinomoto, M. et al. All APOBEC3 family proteins differentially inhibit LINE-1 retrotransposition. *Nucleic Acids Res* 35, 2955-64 (2007).

Kozak, S. L., Marin, M., Rose, K. M., Bystrom, C. & Kabat, D. The anti-HIV-1 editing enzyme APOBEC3G binds HIV-1 RNA and messenger RNAs that shuttle between polysomes and stress granules. *J Biol Chem* 281, 29105-19 (2006).

Kozin, M. B., and Svergun, D. I. *J. Appl. Cryst.* 34, 33-41 (2001).

Kreisberg, J. F., Yonemoto, W., and Greene, W. C. *J Exp Med* 203, 865-870 (2006).

Lau, P. P., Zhu, H. J., Baldini, A., Chamsangavej, C. & Chan, L. Dimeric structure of a human apolipoprotein B mRNA editing protein and cloning and chromosomal localization of its gene. *Proc Natl Acad Sci USA* 91, 8522-6 (1994).

Lau, P. P., Xiong, W. J., Zhu, H. J., Chen, S. H. & Chan, L. *J Biol Chem* 266, 20550-4 (1991).

Lecossier, D., Bouchonnet, F., Clavel, F., and Hance, A. J. *Science* 300, 1112 (2003).

Luo, K. et al. Amino-terminal region of the human immunodeficiency virus type 1 nucleocapsid is required for human APOBEC3G packaging. *J Virol* 78, 11841-52 (2004).

MacElrevey, C. & Wedekind, J. E. in *RNA and DNA Editing: Molecular Mechanisms and Their Integration into Biolgcial Systems*, eds Smith, H. C. (Wiley, New York), chapter 16 in press (2008).

Mangeat, B., Turelli, P., Liao, S. & Trono, D. *J Biol Chem* 279, 14481-3 (2004).

Mangeat, B. et al. Broad antiretroviral defence by human APOBEC3G through lethal editing of nascent reverse transcripts. *Nature* 424, 99-103 (2003).

Mariani, R., Chen, D., Schrofelbauer, B., Navarro, F., Konig, R., Bollman, B., Munk, C., Nymark-McMahon, H., and Landau, N. R. *Cell* 114, 21-31 (2003).

Mehle, A., Goncalves, J., Santa-Marta, M., McPike, M. & Gabuzda, D. *Genes Dev* 18, 2861-6 (2004).

Muckenfuss, H., Hamdorf, M., Held, U., Perkovic, M., Lower, J., Cichutek, K., Flory, E., Schumann, G. G. & Munk, C *J Biol Chem* 281, 22161-72. (2006).

Muramatsu, M., Kinoshita, K., Fagarasan, S., Yamada, S., Shinkai, Y. & Honjo, T. *Cell* 102, 553-63 (2000).

Muramatsu, M., Sankaranand, V. S., Anant, S., Sugai, M., Kinoshita, K., Davidson, N. O. & Honjo, T. *J Biol Chem* 274, 18470-6 (1999).

Nambu, Y., Sugai, M., Gonda, H., Lee, C. G., Katakai, T., Agata, Y., Yokota, Y. & Shimizu, A. *Science* 302, 2137-40 (2003).

Navaratnam, N., Fujino, T., Bayliss, J., Jarmuz, A., How, A., Richardson, N., Somasekaram, A., Bhattacharya, S., Carter, C., and Scott, J. *J Mol Biol* 275, 695-714 (1998).

Navarro, F., Bollman, B., Chen, H., Konig, R., Yu, Q., Chiles, K., and Landau, N. R. Complementary function of the two catalytic domains of APOBEC3G. *Virology* 333, 374-86 (2005).

Newman, E. N. et al. Antiviral function of APOBEC3G can be dissociated from cytidine deaminase activity. Curr Biol 15, 166-70 (2005).

Nguyen, D. H., Gummuluru, S. & Hu, J. *J Virol* 81, 4465-72 (2007).

Okazaki, I. M., Hiai, H., Kakazu, N., Yamada, S., Muramatsu, M., Kinoshita, K. & Honjo, T *J Exp Med* 197, 1173-81 (2003).

Opi, S. et al. Human immunodeficiency virus type 1 Vif inhibits packaging and antiviral activity of a degradation-resistant APOBEC3G variant. *J Virol* 81, 8236-46 (2007).

Opi, S. et al. Monomeric APOBEC3G is catalytically active and has antiviral activity. *J Virol* 80, 4673-82 (2006).

Oppezzo, P., Vuillier, F., Vasconcelos, Y., Dumas, G., Magnac, C., Payelle-Brogard, B., Pritsch, O. & Dighiero, G. Blood 101, 4029-32 (2003).

Papavasiliou, F. N. & Schatz, D. G. Nature 408, 216-21 (2000).

Petoukhov, M. V., Monie, T. P., Allain, F. H., Matthews, S., Curry, S., and Svergun, D. I. *Structure* 14, 1021-1027 (2006).

Platt, E. J., Wehrly, K., Kuhmann, S. E., Chesebro, B. & Kabat, D. Effects of CCR5 and CD4 cell surface concentrations on infections by macrophagetropic isolates of human immunodeficiency virus type 1. *J Virol* 72, 2855-64 (1998).

Powell, L. M., Wallis, S. C., Pease, R. J., Edwards, Y. H., Knott, T. J. & Scott, *J. Cell* 50, 831-40 (1987).

Prochnow, C., Bransteitter, R., Klein, M. G., Goodman, M. F. & Chen, X. S. The APOBEC-2 crystal structure and functional implications for the deaminase Nature 445, 447-51 (2007).

Rucci, F., Cattaneo, L., Marrella, V., Sacco, M. G., Sobacchi, C., Lucchini, F., Nicola, S., Della Bella, S., Villa, M. L., Imberti, L., Gentili, F., Montagna, C., Tiveron, C., Tatangelo, L., Facchetti, F., Vezzoni, P. & Villa, A. *Gene* 377, 150-8 (2006).

Schafer, A., Bogerd, H. P. & Cullen, B. R. Specific packaging of APOBEC3G into HIV-1 virions is mediated by the nucleocapsid domain of the gag polyprotein precursor. *Virology* 328, 163-8 (2004).

Schrofelbauer, B., Senger, T., Manning, G. & Landau, N. R. *J Virol* 80, 5984-91 (2006).

Schrofelbauer, B., Chen, D. & Landau, N. R. *Proc Natl Acad Sci USA* 101, 3927-32 (2004).

Sheehy, A. M., Gaddis, N. C., Choi, J. D., and Malim, M. H. *Nature* 418, 646-650 (2002).

Simon, J. H., Southerling, T. E., Peterson, J. C., Meyer, B. E. & Malim, M. H. Complementation of vif-defective human immunodeficiency virus type 1 by primate, but not nonprimate, lentivirus vif genes. *J Virol* 69, 4166-72 (1995).

Skuse, G. R., Cappione, A. J., Sowden, M., Metheny, L. J. & Smith, H. C. *Nucleic Acids Res* 24, 478-85 (1996).

Smith, H. C., Wedekind, J. E., Xie, K., and Sowden, M. P. in *Mammalian C to U Editing. Topics in Current Genetics* (H., G., ed), pp. 1610-2096, Springer-Verlag, Berlin (2005).

Smith, H. C. Analysis of protein complexes assembled on apolipoprotein B mRNA for mooring sequence-dependent RNA editing. Methods 15, 27-39 (1998).

Soros, V. B., Yonemoto, W. & Greene, W. C. Newly synthesized APOBEC3G is incorporated into HIV virions, inhibited by HIV RNA, and subsequently activated by RNase H. *PLoS Pathog* 3, e15 (2007).

Sowden, M. P., Ballatori, N., Jensen, K. L., Reed, L. H., and Smith, H. C. *J Cell Sci* 115, 1027-1039 (2002).

Sowden, M., Hamm, J. K. & Smith, H. C. *J Biol Chem* 271, 3011-7 (1996).

Sreerama, N., and Woody, R. W. Anal Biochem 287, 252-260 (2000).

Stopak, K., de Noronha, C., Yonemoto, W., and Greene, W. C. Mol Cell 12, 591-601 (2003).

Svarovskaia, E. S., Xu, H., Mbisa, J. L., Barr, R., Gorelick, R. J., Ono, A., Freed, E. O., Hu, W. S. & Pathak, V. K. *J Biol Chem* 279, 35822-8 (2004).

Svergun, D. I. *Biophys J* 76, 2879-2886 (1999).

Svergun, D. I. *J. Appl. Cryst.* 25, 495-495-493 (1992).

Ta, V. T., Nagaoka, H., Catalan, N., Durandy, A., Fischer, A., Imai, K., Nonoyama, S., Tashiro, J., Ikegawa, M., Ito, S., Kinoshita, K., Muramatsu, M. & Honjo, T. *Nat Immunol* 4, 843-8 (2003).

Tinoco, I. J., Sauer, K., Wang, J. C., and Puglisi, J. D. Physical Chemistry: Principles and Applications in Biological Sciences, 4 Ed., Prentice-Hall, Inc., Upper Saddle River, N.J. (2002).

Volkov, V. V., and Svergun, D. I. *J. Appl. Cryst.* 36, 860-864 (2003).

von Wronski, M. A., Hirano, K. I., Cagen, L. M., Wilcox, H. G., Raghow, R., Thorngate, F. E., Heimberg, M., Davidson, N. O. & Elam, M. B. *Metabolism* 47, 869-73 (1998).

Wang, J. et al. Identification of a specific domain required for dimerization of activation-induced cytidine deaminase. *J Biol Chem* 281, 19115-23 (2006).

Wedekind, J. E. et al. Nanostructures of APOBEC3G support a hierarchical assembly model of high molecular mass ribonucleoprotein particles from dimeric subunits. *J Biol Chem* 281, 38122-6 (2006).

Wedekind, J. E., Dance, G. S., Sowden, M. P., and Smith, H. C. *Trends Genet.* 19, 207-216 (2003).

Wichroski, M. J., Robb, G. B. & Rana, T. M. Human Retroviral Host Restriction Factors APOBEC3G and APOBEC3F Localize to mRNA Processing Bodies. PLoS Pathog 2, e41 (2006).

Wichroski, M. J., Ichiyama, K. & Rana, T. M. Analysis of HIV-1 viral infectivity factor-mediated proteasome-dependent depletion of APOBEC3G: correlating function and subcellular localization. *J Biol Chem* 280, 8387-96 (2005).

Wriggers, W., and Chacon, P. *Structure* 9, 779-788 (2005) (2001).

Xie, K. et al. The structure of a yeast RNA-editing deaminase provides insight into the fold and function of activation-induced deaminase and APOBEC-1. *Proc Natl Acad Sci USA* 101, 8114-9 (2004).

Yamanaka, S., Poksay, K. S., Arnold, K. S. & Innerarity, T. L. *Genes Dev* 11, 321-33 (1997).

Yamanaka, S., K. S. Poksay, D. M. Driscoll, Innerarity, T. L. *J. Biol. Chem.* 271, 11506-11510 (1996).

Yamanaka, S., M. Balestra, L. Ferrell, J. Fan, K. S. Arnold, S. Taylor, J. M. Taylor, Innerarity, T. L. *Proc. Natl. Acad. Sci. USA* 92, 8483-8487 (1995).

Yang, Y. & Smith, H. C. *Proc Natl Acad Sci USA* 94, 13075-80 (1997).

Yang, Y., Kovalski, K. & Smith, H. C. *J Biol Chem* 272, 27700-6 (1997).

Yu, Q. et al. Single-strand specificity of APOBEC3G accounts for minus-strand deamination of the HIV genome. Nat Struct Mol Biol 11, 435-42 (2004).

Yu, X. et al. Induction of APOBEC3G ubiquitination and degradation by an HIV-1 Vif-Cul5-SCF complex. Science 302, 1056-60 (2003).

Zennou, V., Perez-Caballero, D., Gottlinger, H. & Bieniasz, P. D. APOBEC3G incorporation into human immunodeficiency virus type 1 particles. *J Virol* 78, 12058-61 (2004).

Zennou, V., Perez-Caballero, D., Gottlinger, H. & Bieniasz, P. D. *J Virol* 78, 12058-61 (2004).

Zhang, H. et al. The cytidine deaminase CEM15 induces hypermutation in newly synthesized HIV-1 DNA. *Nature* 424, 94-8 (2003).

What is claimed is:

1. A method of inhibiting viral infectivity in a cell comprising administering an inhibitor of the interaction between low molecular mass APOBEC3 G (LMM) dimers and high molecular mass APOBEC3G (HMM) conversion molecules to the cell, wherein the inhibitor stabilizes the LMM dimer, thereby inhibiting viral infectivity in the cell, wherein the inhibitor is selected from the group consisting of a small molecule, a peptide, a nucleic acid molecule, an antibody, and any combinations thereof, and wherein the inhibitor binds to at least one domain selected from the group consisting of the N-terminal pseudocatalytic domain and C-terminal pseudocatalytic domain of LMM.

2. The method of claim 1, wherein the cell is in a subject.

3. The method of claim 2, wherein the subject has a viral infection.

4. The method of claim 3, wherein the viral infection is Human immunodeficiency virus (HIV).

5. A method of inhibiting viral infectivity in a cell comprising administering an inhibitor of the interaction between the N-terminal catalytic domain of low molecular mass APOBEC3G (LMM) and high molecular mass APOBEC3 G (HMM) conversion molecules to the cell, thereby inhibiting viral infectivity in the cell, wherein the inhibitor is selected from the group consisting of a small molecule, a peptide, a nucleic acid molecule, an antibody, and any Combinations thereof, and wherein the inhibitor binds to the N-terminal catalytic domain of LMM.

6. The method of claim 5, wherein HMM conversion molecules comprise an RNA molecule, and wherein the inhibitor inhibits the interaction between the N-terminal catalytic domain of LMM and the RNA molecule.

* * * * *

SEQUENCE LISTING

```
<160> NUMBER OF SEQ ID NOS: 16

<210> SEQ ID NO 1
<211> LENGTH: 42
<212> TYPE: DNA
<213> ORGANISM: Artificial Sequence
<220> FEATURE:
<223> OTHER INFORMATION: synthetic construct

<400> SEQUENCE: 1
attattatta ttattcccaa ttatttattt atttatttat tt            42

<210> SEQ ID NO 2
<211> LENGTH: 42
<212> TYPE: DNA
<213> ORGANISM: Artificial Sequence
<220> FEATURE:
<223> OTHER INFORMATION: synthetic construct

<400> SEQUENCE: 2
attattatta ttattagaaa ttatttattt atttatttat tt            42

<210> SEQ ID NO 3
<211> LENGTH: 40
<212> TYPE: DNA
<213> ORGANISM: Artificial Sequence
<220> FEATURE:
<223> OTHER INFORMATION: synthetic construct

<400> SEQUENCE: 3
ctcgaattca gggatgaaac ctcacttcag aaacacagtg               40

<210> SEQ ID NO 4
<211> LENGTH: 18
<212> TYPE: DNA
<213> ORGANISM: Artificial Sequence
<220> FEATURE:
<223> OTHER INFORMATION: synthetic construct

<400> SEQUENCE: 4
ctggagaatg gcccgcag                                       18

<210> SEQ ID NO 5
<211> LENGTH: 22
<212> TYPE: DNA
<213> ORGANISM: Artificial Sequence
<220> FEATURE:
<223> OTHER INFORMATION: synthetic construct

<400> SEQUENCE: 5
gataactgtg gtaattctag ag                                  22
```

-continued

<210> SEQ ID NO 6
<211> LENGTH: 19
<212> TYPE: DNA
<213> ORGANISM: Artificial Sequence
<220> FEATURE:
<223> OTHER INFORMATION: synthetic construct

<400> SEQUENCE: 6
gtaatttgcg cgcctgctg                                                19

<210> SEQ ID NO 7
<211> LENGTH: 18
<212> TYPE: DNA
<213> ORGANISM: Artificial Sequence
<220> FEATURE:
<223> OTHER INFORMATION: synthetic construct

<400> SEQUENCE: 7
gagcccagcg ccgaatcc                                                 18

<210> SEQ ID NO 8
<211> LENGTH: 22
<212> TYPE: DNA
<213> ORGANISM: Artificial Sequence
<220> FEATURE:
<223> OTHER INFORMATION: synthetic construct

<400> SEQUENCE: 8
ctcttgaact ctctcttcaa ag                                            22

<210> SEQ ID NO 9
<211> LENGTH: 16
<212> TYPE: PRT
<213> ORGANISM: Artificial Sequence
<220> FEATURE:
<223> OTHER INFORMATION: synthetic construct

<400> SEQUENCE: 9

Lys Val Thr Leu Thr Ile Phe Val Ala Arg Leu Tyr Tyr Phe Trp Asp
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(6)
<223> OTHER INFORMATION: Xaa = Any Amino Acid
<220> FEATURE:
<221> NAME/KEY: VARIANT
<222> LOCATION: (9)..(13)
<223> OTHER INFORMATION: Xaa = Any Amino Acid
<220> FEATURE:
<221> NAME/KEY: VARIANT
<222> LOCATION: (15)..(15)
<223> OTHER INFORMATION: Xaa = Any Amino Acid

<400> SEQUENCE: 10

Asn Xaa Xaa Xaa Xaa Xaa Ser Ala Xaa Xaa Xaa Xaa Xaa Tyr Xaa Gln
1               5                   10                  15

<210> SEQ ID NO 11
<211> LENGTH: 16
<212> TYPE: PRT

```
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa = Any Amino Acid
<220> FEATURE:
<221> NAME/KEY: VARIANT
<222> LOCATION: (4)..(7)
<223> OTHER INFORMATION: Xaa = Any Amino Acid
<220> FEATURE:
<221> NAME/KEY: VARIANT
<222> LOCATION: (9)..(14)
<223> OTHER INFORMATION: Xaa = Any Amino Acid

<400> SEQUENCE: 11

Asn Xaa Asn Xaa Xaa Xaa Xaa Thr Xaa Xaa Xaa Xaa Xaa Xaa Gly Tyr
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa = Any Amino Acid
<220> FEATURE:
<221> NAME/KEY: VARIANT
<222> LOCATION: (4)..(4)
<223> OTHER INFORMATION: Xaa = Any Amino Acid
<220> FEATURE:
<221> NAME/KEY: VARIANT
<222> LOCATION: (6)..(7)
<223> OTHER INFORMATION: Xaa = Any Amino Acid
<220> FEATURE:
<221> NAME/KEY: VARIANT
<222> LOCATION: (9)..(10)
<223> OTHER INFORMATION: Xaa = Any Amino Acid
<220> FEATURE:
<221> NAME/KEY: VARIANT
<222> LOCATION: (12)..(12)
<223> OTHER INFORMATION: Xaa = Any Amino Acid

<400> SEQUENCE: 12

His Xaa Arg Xaa Arg Xaa Xaa Ala Xaa Xaa Ile Xaa Asp Tyr Asp Pro
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa = Any Amino Acid
<220> FEATURE:
<221> NAME/KEY: VARIANT
<222> LOCATION: (4)..(4)
<223> OTHER INFORMATION: Xaa = Any Amino Acid
<220> FEATURE:
<221> NAME/KEY: VARIANT
<222> LOCATION: (6)..(7)
<223> OTHER INFORMATION: Xaa = Any Amino Acid
<220> FEATURE:
<221> NAME/KEY: VARIANT
<222> LOCATION: (9)..(10)
<223> OTHER INFORMATION: Xaa = Any Amino Acid
<220> FEATURE:
<221> NAME/KEY: VARIANT
```

```
<222> LOCATION: (12)..(12)
<223> OTHER INFORMATION: Xaa = Any Amino Acid

<400> SEQUENCE: 13

His Xaa Ser Xaa Cys Xaa Xaa Thr Xaa Xaa Ile Xaa Asp Asp Gln Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(7)
<223> OTHER INFORMATION: Xaa = Any Amino Acid
<220> FEATURE:
<221> NAME/KEY: VARIANT
<222> LOCATION: (9)..(16)
<223> OTHER INFORMATION: Xaa = Any Amino Acid

<400> SEQUENCE: 14

Asn Xaa Asn Xaa Xaa Xaa Xaa Thr Xaa Xaa Xaa Xaa Xaa Xaa Xaa Xaa
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa = Any Amino Acid
<220> FEATURE:
<221> NAME/KEY: VARIANT
<222> LOCATION: (4)..(4)
<223> OTHER INFORMATION: Xaa = Any Amino Acid
<220> FEATURE:
<221> NAME/KEY: VARIANT
<222> LOCATION: (6)..(7)
<223> OTHER INFORMATION: Xaa = Any Amino Acid
<220> FEATURE:
<221> NAME/KEY: VARIANT
<222> LOCATION: (9)..(10)
<223> OTHER INFORMATION: Xaa = Any Amino Acid
<220> FEATURE:
<221> NAME/KEY: VARIANT
<222> LOCATION: (12)..(12)
<223> OTHER INFORMATION: Xaa = Any Amino Acid

<400> SEQUENCE: 15

His Xaa Arg Xaa Arg Xaa Xaa Ala Xaa Xaa Ile Xaa Asp Tyr Asp Pro
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: synthetic sequence

<400> SEQUENCE: 16

Pro Lys Lys Lys Arg Lys Val
1               5
```